(12) United States Patent
Shelton, IV et al.

(10) Patent No.: US 12,029,508 B2
(45) Date of Patent: Jul. 9, 2024

(54) ADJUSTABLE POWER TRANSMISSION MECHANISM FOR POWERED SURGICAL STAPLER

(71) Applicant: Cilag GmbH International, Zug (CH)

(72) Inventors: Frederick E. Shelton, IV, Hillsboro, OH (US); Kevin M. Fiebig, Cincinnati, OH (US); Shane R. Adams, Lebanon, OH (US); Adam D. Hensel, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 165 days.

(21) Appl. No.: 17/402,744

(22) Filed: Aug. 16, 2021

(65) Prior Publication Data
US 2023/0051938 A1    Feb. 16, 2023

(51) Int. Cl.
| A61B 17/068 | (2006.01) |
| A61B 17/072 | (2006.01) |
| A61B 34/30 | (2016.01) |
| A61B 17/00 | (2006.01) |

(52) U.S. Cl.
CPC .......... *A61B 34/30* (2016.02); *A61B 17/0686* (2013.01); *A61B 17/072* (2013.01); *A61B 2017/00367* (2013.01); *A61B 2017/07257* (2013.01); *A61B 2017/07271* (2013.01); *A61B 2017/07285* (2013.01); *A61B 2034/301* (2016.02)

(58) Field of Classification Search
CPC .............. A61B 17/0686; A61B 17/072; A61B 17/07207; A61B 2017/00367; A61B 2017/00477; A61B 2017/07257; A61B 2017/07271; A61B 2017/07285

USPC ............ 227/176.1, 175.1, 178.1; 606/1, 219
See application file for complete search history.

(56) References Cited

U.S. PATENT DOCUMENTS

| 5,129,570 A | 7/1992 | Schulze et al. |
| 7,404,508 B2 | 7/2008 | Smith et al. |
| 7,434,715 B2 | 10/2008 | Shelton, IV et al. |

(Continued)

FOREIGN PATENT DOCUMENTS

| WO | WO 2015/153642 A1 | 10/2015 |
| WO | WO 2017/083125 A1 | 5/2017 |

(Continued)

OTHER PUBLICATIONS

"Mechanical advantage", by University of Calgary, retrieved from URL https://energyeducation.ca/encyclopedia/Mechanical_advantage#:~:text=Mechanical%20advantage%20is%20a%20measure,equal%20to%20the%20input%20energy. on Sep. 21, 2023 (Year: 2023).*

(Continued)

*Primary Examiner* — Valentin Neacsu
(74) *Attorney, Agent, or Firm* — Frost Brown Todd LLP

(57) ABSTRACT

A surgical instrument includes a body, a shaft assembly, an end effector, a stapling assembly, and a drive system. The shaft assembly extends distally from the body. The end effector is disposed on a distal end of the shaft assembly and includes a first jaw and a second jaw. The stapling assembly is supported by one of the first jaw or the second jaw of the end effector. The drive system includes a shift mechanism configured to selectively modify a mechanical advantage of a drive input driven by a motor and used to power one or more functions associated with operation of the end effector.

20 Claims, 26 Drawing Sheets

(56) References Cited

U.S. PATENT DOCUMENTS

| | | | |
|---|---|---|---|
| 7,721,930 B2 | 5/2010 | McKenna et al. | |
| 7,810,692 B2 | 10/2010 | Hall et al. | |
| 7,832,408 B2 | 11/2010 | Shelton, IV et al. | |
| 7,845,537 B2 | 12/2010 | Shelton, IV et al. | |
| 8,083,120 B2 | 12/2011 | Shelton, IV et al. | |
| 8,210,411 B2 | 7/2012 | Yates et al. | |
| 8,408,439 B2 | 4/2013 | Huang et al. | |
| 8,453,914 B2 | 6/2013 | Laurent et al. | |
| 8,708,213 B2 | 4/2014 | Shelton, IV et al. | |
| 9,060,770 B2 | 6/2015 | Shelton, IV et al. | |
| 9,186,142 B2 | 11/2015 | Fanelli et al. | |
| 9,517,065 B2 | 12/2016 | Simms et al. | |
| 9,622,746 B2 | 4/2017 | Simms et al. | |
| 9,717,497 B2 | 8/2017 | Zerkle et al. | |
| 9,795,379 B2 | 10/2017 | Leimbach et al. | |
| 9,808,248 B2 | 11/2017 | Hoffman | |
| 9,839,487 B2 | 12/2017 | Dachs, II | |
| 10,011,018 B2 | 7/2018 | McGrogan et al. | |
| 10,092,292 B2 | 10/2018 | Boudreaux et al. | |
| 10,307,170 B2 | 6/2019 | Parfett et al. | |
| 10,485,621 B2 | 11/2019 | Morrissette et al. | |
| 10,537,400 B2 | 1/2020 | Dachs, II et al. | |
| 10,610,313 B2 | 4/2020 | Bailey et al. | |
| 10,667,809 B2 | 6/2020 | Bakos et al. | |
| 10,806,530 B2 | 10/2020 | Liao et al. | |
| 10,863,988 B2 | 12/2020 | Patel et al. | |
| 11,020,138 B2 | 6/2021 | Ragosta | |
| 11,026,755 B2 | 6/2021 | Weir et al. | |
| 11,076,926 B2 | 8/2021 | Ragosta et al. | |
| 11,147,552 B2 | 10/2021 | Burbank et al. | |
| 11,166,773 B2 | 11/2021 | Ragosta et al. | |
| 11,234,700 B2 | 2/2022 | Ragosta et al. | |
| 11,259,884 B2 | 3/2022 | Burbank | |
| 2006/0185682 A1 | 8/2006 | Marczyk | |
| 2012/0209314 A1 | 8/2012 | Weir et al. | |
| 2014/0249557 A1* | 9/2014 | Koch, Jr. | A61B 34/74 606/170 |
| 2015/0297228 A1 | 10/2015 | Huitema et al. | |
| 2016/0361126 A1 | 12/2016 | Schena et al. | |
| 2017/0020617 A1 | 1/2017 | Weir et al. | |
| 2017/0265865 A1 | 9/2017 | Burbank | |
| 2017/0265954 A1 | 9/2017 | Burbank et al. | |
| 2017/0333037 A1 | 11/2017 | Wellman et al. | |
| 2018/0116741 A1* | 5/2018 | Garcia Kilroy | G01L 3/1428 |
| 2018/0168756 A1 | 6/2018 | Liao et al. | |
| 2018/0271608 A1 | 9/2018 | Ragosta et al. | |
| 2018/0310935 A1 | 11/2018 | Wixey | |
| 2018/0325606 A1 | 11/2018 | Weir et al. | |
| 2018/0344419 A1 | 12/2018 | Dachs, II et al. | |
| 2019/0038371 A1 | 2/2019 | Wixey et al. | |
| 2019/0076142 A1 | 3/2019 | Wixey | |
| 2019/0076143 A1 | 3/2019 | Smith | |
| 2019/0167266 A1 | 6/2019 | Patel et al. | |
| 2019/0200989 A1 | 7/2019 | Burbank et al. | |
| 2019/0201136 A1* | 7/2019 | Shelton, IV | G16H 50/20 |
| 2019/0239967 A1 | 8/2019 | Ragosta et al. | |
| 2019/0262088 A1 | 8/2019 | Burbank | |
| 2020/0138529 A1 | 5/2020 | Ragosta et al. | |
| 2020/0397430 A1 | 12/2020 | Patel et al. | |
| 2020/0405301 A1 | 12/2020 | Shelton, IV et al. | |
| 2020/0405403 A1* | 12/2020 | Shelton, IV | A61B 46/10 |
| 2021/0059777 A1* | 3/2021 | Overmyer | A61B 34/71 |
| 2021/0393340 A1 | 12/2021 | Beckman et al. | |
| 2021/0401433 A1 | 12/2021 | Freidel et al. | |
| 2023/0051938 A1* | 2/2023 | Shelton, IV | A61B 34/37 |

FOREIGN PATENT DOCUMENTS

| | | |
|---|---|---|
| WO | WO 2017/083129 A1 | 5/2017 |
| WO | WO 2018/049198 A1 | 3/2018 |
| WO | WO 2018/049206 A1 | 3/2018 |
| WO | WO 2018/049211 A1 | 3/2018 |
| WO | WO 2018/049217 A1 | 3/2018 |
| WO | WO 2018/052806 A1 | 3/2018 |
| WO | WO 2018/052810 A1 | 3/2018 |
| WO | WO 2018/071497 A1 | 4/2018 |
| WO | WO 2018/071763 A1 | 4/2018 |
| WO | WO 2018/085529 A2 | 5/2018 |
| WO | WO 2018/175467 A1 | 9/2018 |
| WO | WO 2019/165403 A1 | 8/2019 |
| WO | WO 2020/131290 A1 | 6/2020 |

OTHER PUBLICATIONS

"Simple Machines" by HyperPhysics at Georgia State University, retrieved from URL http://hyperphysics.phy-astr.gsu.edu/hbase/Mechanics/simmac.html on Sep. 21, 2023 (Year: 2023).*
U.S. Appl. No. 17/402,679.
U.S. Appl. No. 17/088,941, entitled "Surgical Stapler End Effector Sled Having Cartridge Wall Support Feature," filed Nov. 4, 2020.
U.S. Appl. No. 17/402,674, entitled "Methods of Operating a Robotic Surgical Stapler," filed Aug. 16, 2021.
U.S. Appl. No. 17/402,675, entitled "Multi-Threshold Motor Control Algorithm for Powered Surgical Stapler," filed Aug. 16, 2021.
U.S. Appl. No. 17/402,677, entitled "Variable Response Motor Control Algorithm for Powered Surgical Stapler," filed Aug. 16, 2021.
U.S. Appl. No. 17/402,679, entitled "Powered Surgical Stapler Having Independently Operable Closure and Firing Systems," filed Aug. 16, 2021.
U.S. Appl. No. 17/402,695, entitled "Firing System Features for Surgical Stapler," filed Aug. 16, 2021.
U.S. Appl. No. 17/402,701, entitled "Multiple-Sensor Firing Lockout Mechanism for Powered Surgical Stapler," filed Aug. 16, 2021.
U.S. Appl. No. 17/402,703, entitled "Proximally Located Firing Lockout Mechanism for Surgical Stapler," filed Aug. 16, 2021.
U.S. Appl. No. 17/402,720, entitled "Cartridge-Based Firing Lockout Mechanism for Surgical Stapler," filed Aug. 16, 2021.
U.S. Appl. No. 17/402,732, entitled "Multi-Position Restraining Member for Sled Movement," filed Aug. 16, 2021.
U.S. Appl. No. 17/402,738, entitled "Firing Member Tracking Feature for Surgical Stapler," filed Aug. 16, 2021.
U.S. Appl. No. 17/402,749, entitled "Firing Bailout System for Powered Surgical Stapler," filed Aug. 16, 2021.
U.S. Appl. No. 17/402,759, entitled "Deflectable Firing Member for Surgical Stapler," filed Aug. 16, 2021.
U.S. Appl. No. 17/402,674.
U.S. Appl. No. 17/402,675.
U.S. Appl. No. 17/402,677.
U.S. Appl. No. 17/402,695.
U.S. Appl. No. 17/402,701.
U.S. Appl. No. 17/402,703.
U.S. Appl. No. 17/402,720.
U.S. Appl. No. 17/402,732.
U.S. Appl. No. 17/402,738.
U.S. Appl. No. 17/402,749.
U.S. Appl. No. 17/402,759.
U.S. Pat. No. 11,779,332.
International Search Report and Written Opinion dated Dec. 7, 2022 for Application No. PCT/IB2022/057615, 11 pgs.

* cited by examiner

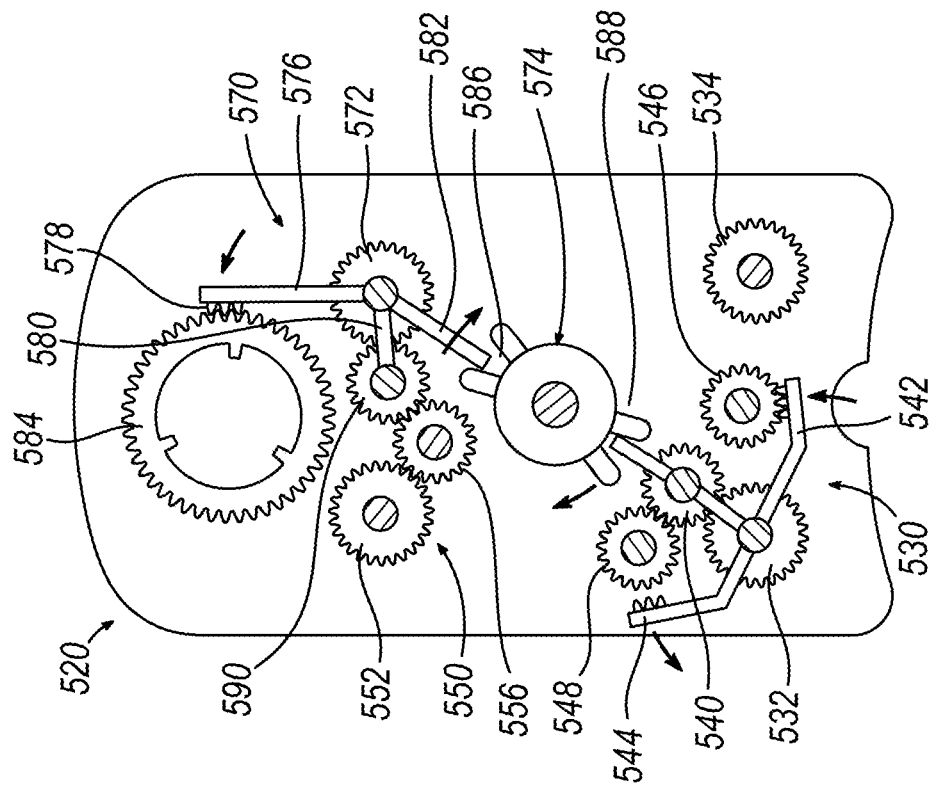
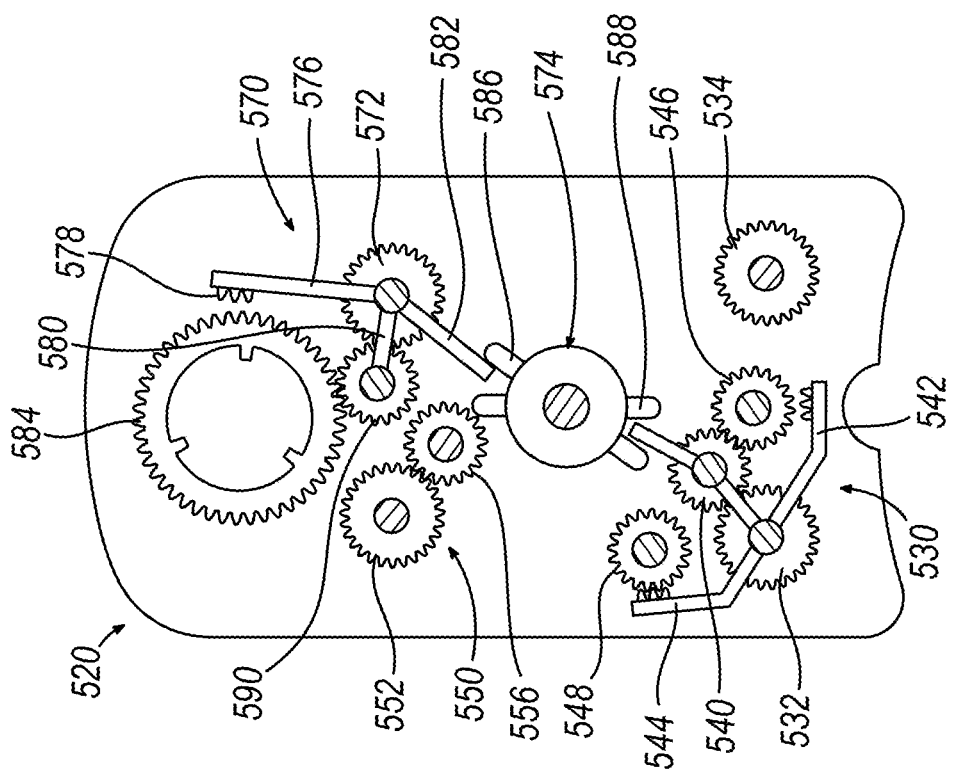

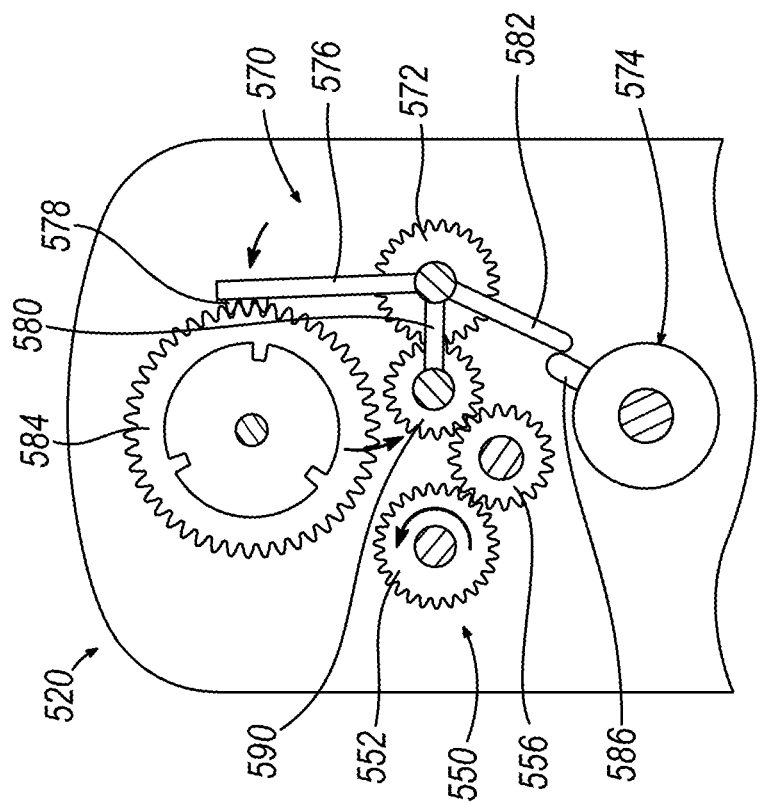
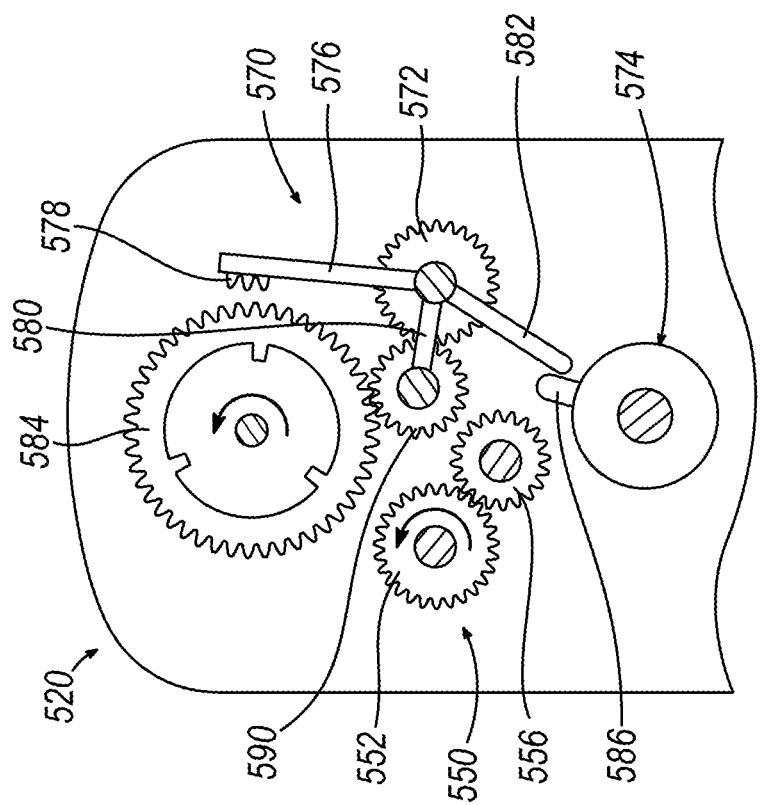

ADJUSTABLE POWER TRANSMISSION MECHANISM FOR POWERED SURGICAL STAPLER

BACKGROUND

A variety of surgical instruments include an end effector for use in conventional medical treatments and procedures conducted by a medical professional operator, as well as applications in robotically assisted surgeries. Such surgical instruments may be directly gripped and manipulated by a surgeon or incorporated into robotically surgical systems. In the case of robotically assisted surgery, the surgeon may operate a master controller to remotely control the motion of such surgical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may include one or more hand input devices (such as joysticks, exoskeletal gloves, master manipulators, or the like), which are coupled by a servo mechanism to the surgical instrument. In one example, a servo motor moves a manipulator supporting the surgical instrument based on the surgeon's manipulation of the hand input devices. During the surgery, the surgeon may employ, via a robotic surgical system, a variety of surgical instruments including an ultrasonic blade, a surgical stapler, a tissue grasper, a needle driver, an electrosurgical cautery probe, etc. Each of these structures performs functions for the surgeon, for example, cutting tissue, coagulating tissue, holding or driving a needle, grasping a blood vessel, dissecting tissue, or cauterizing tissue.

Examples of surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Examples of surgical staplers and associated features are disclosed in U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; U.S. Pat. No. 8,453,914, entitled "Motor-Driven Surgical Cutting Instrument with Electric Actuator Directional Control Assembly," issued Jun. 4, 2013; U.S. Pat. No. 9,186,142, entitled "Surgical Instrument End Effector Articulation Drive with Pinion and Opposing Racks," issued on Nov. 17, 2015; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 10,092,292, entitled "Staple Forming Features for Surgical Stapling Instrument," issued Oct. 9, 2018; U.S. Pat. No. 9,717,497, entitled "Lockout Feature for Movable Cutting Member of Surgical Instrument," issued Aug. 1, 2017; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; and U.S. Pat. No. 8,210,411, entitled "Motor-Driven Surgical Instrument," issued Jul. 3, 2012. The disclosure of each of the above-cited U.S. Patents is incorporated by reference herein in its entirety.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 15A depicts a top plan view of another exemplary alternative drive system that may be used with the surgical instrument of FIG. 4, the drive system in a first drive configuration;

FIG. 15B depicts another top plan view of the drive system of FIG. 15A, the drive system in a second drive configuration;

FIG. 16A depicts a detailed top plan view of the drive system of FIG. 15A, the drive system in the first drive configuration;

FIG. 16B depicts another detailed top plan view of the drive system of FIG. 15A, the drive system in the second drive configuration;

Figure 1:
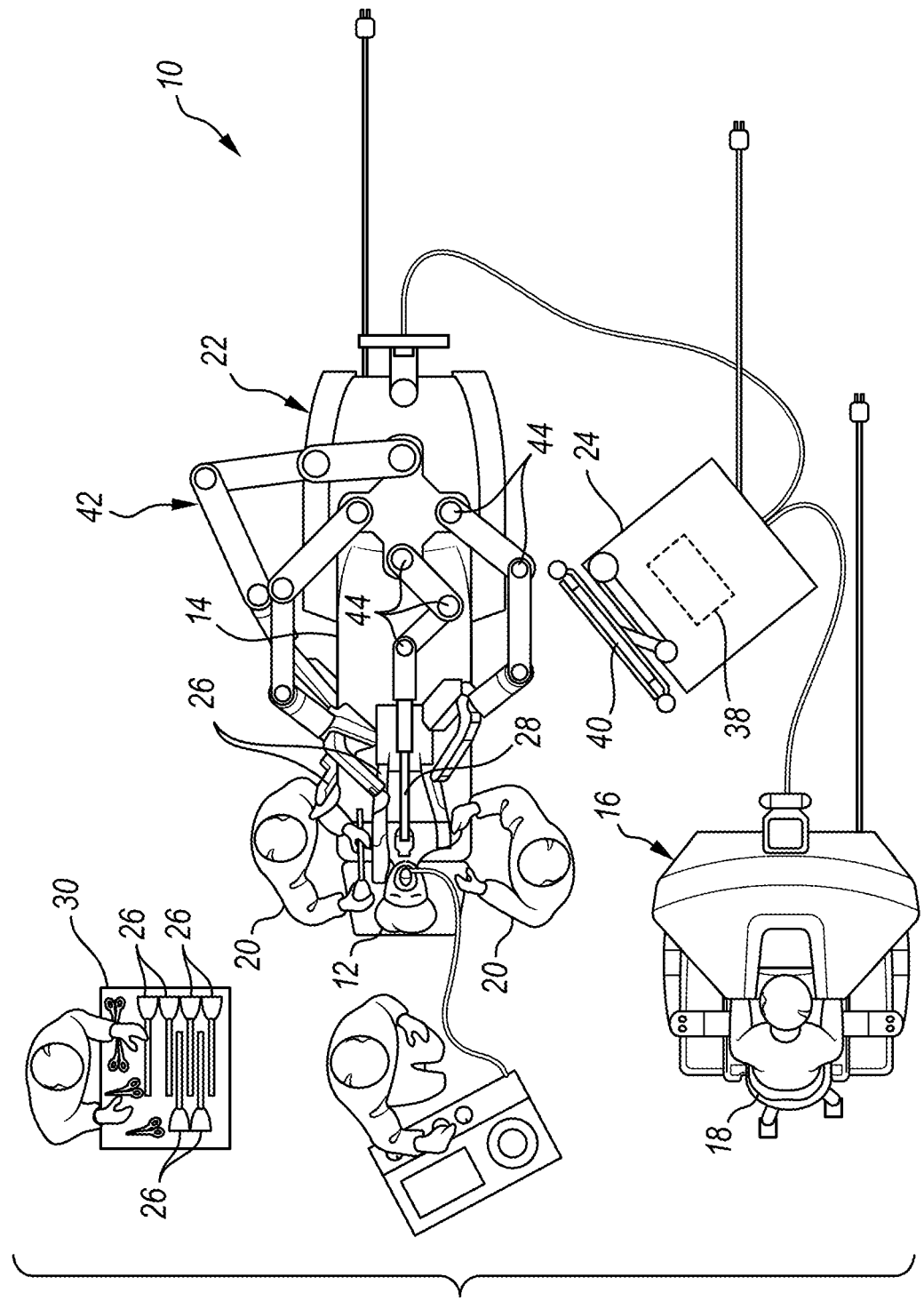
FIG. 1 depicts a top plan view of a robotic surgical system being used to perform a surgical procedure.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that, for convenience and clarity, spatial terms such as "clockwise," "counterclockwise," "inner," "outer," "upper," "lower," "lateral" and the like also are used herein for reference to relative positions and directions. Such terms are used below with reference to views as illustrated for clarity and are not intended to limit the invention described herein.

Aspects of the present examples described herein may be integrated into a robotically-enabled medical system, including as a robotic surgical system, capable of performing a variety of medical procedures, including both minimally invasive, such as laparoscopy, and non-invasive, such as endoscopy, procedures. Among endoscopy procedures, the robotically-enabled medical system may be capable of performing bronchoscopy, ureteroscopy, gastroscopy, etc.

I. Exemplary Robotic Surgical System

A. Overview

FIG. 1 shows a top plan view of an exemplary robotic surgical system (10) that may be used for performing a diagnostic or surgical procedure on a patient (12) who is lying down on an operating table (14). Robotic surgical system (10) may be constructed and operable in accordance with at least some of the teachings of U.S. Pat. No. 9,839,487, entitled "Backup Latch Release for Surgical Instrument," issued Dec. 12, 2017; U.S. Pat. No. 10,485,621, entitled "Sterile Barrier Between Surgical Instrument and Teleoperated Actuator," issued Nov. 26, 2019; U.S. Pat. No. 10,806,530, entitled "System and Method for Patient-Side Instrument Control," issued Oct. 20, 2020; U.S. Pat. No. 10,537,400, entitled "Detection Pins to Determine Presence of Surgical Instrument and Adapter on Manipulator," issued Jan. 21, 2020; U.S. Pat. No. 10,863,988, entitled "Surgical Instrument with Lockout Mechanism," published Dec. 15, 2020; U.S. Pat. No. 10,610,313, entitled "Surgical Instrument with Shiftable Transmission," issued Apr. 7, 2020; U.S. Pub. No. 2018/0271608, entitled "Manual Release for Medical Device Drive System," published Sep. 27, 2018; U.S. Pub. No. 2018/0325606, entitled "Systems and Methods for Operating an End Effector," published Nov. 15, 2018; U.S. Pub. No. 2019/0200989, entitled "Stapler Reload Detection and Identification," published Jul. 4, 2019; U.S. Pub. No. 2019/0239967, entitled "Stapler Beam Architecture," published Aug. 8, 2019; U.S. Pub. No. 2019/0262088, entitled "Robotic Surgical Stapler Assembly Configured to Use Stapler Reload," published Aug. 29, 2019; U.S. Pub. No. 2019/0239877, entitled "Wrist Architecture," published Aug. 8, 2019; U.S. Pub. No. 2019/0201150, entitled "Push-Pull Surgical Instrument End Effector Actuation Using Flexible Tension Member," published Jul. 4, 2019; U.S. Pub. No. 2019/0282233, entitled "Stapler Cartridge With an Integral Knife," published Sep. 19, 2019; U.S. Pub. No. 2019/0262088, entitled "Robotic Surgical Stapler Assembly Configured to Use Stapler Reload," published Aug. 29, 2019; U.S. Pub. No. 2020/0138529, entitled "Locking System for Medical Device Drive System," published May 7, 2020; and/or U.S. Pub. No. 2020/0397430, entitled "Surgical Instrument With Lockout Mechanism," published Dec. 24, 2020. The disclosure of each of the above-cited U.S. Patents and U.S. Patent Publications is incorporated by reference herein in its entirety.

Robotic surgical system (10) may include a surgeon's console (16) for use by a surgeon (18) during a surgical procedure. One or more assistants (20) may also participate in the procedure. Robotic surgical system (10) may include a patient side cart (22) (i.e., a surgical robot) and an electronics cart (24). Patient side cart (22) may manipulate at least one surgical instrument (26) (also referred to as a "tool assembly" or "tool") through an incision in the body of patient (12) while surgeon (18) views the surgical site through surgeon's console (16). As will be described in greater detail below, surgical instrument(s) (26) and an imaging device (shown as an endoscope (28)) may be removably coupled with patient side cart (22). Electronics cart (24) may be used to process the images of the surgical site for subsequent display to the surgeon (18) through surgeon's console (16). Electronics cart (24) may be coupled with endoscope (28) and may include a processor (38) (shown schematically) to process captured images for subsequent display, such as to surgeon (18) on the surgeon's console (16), on a display (40) of electronics cart (24), or another suitable display located locally and/or remotely. The images may also be processed by a combination of electronics cart (24) and processor (38), which may be coupled together to process the captured images jointly, sequentially, and/or combinations thereof. Electronics cart (24) may overlay the captured images with a virtual control interface prior to displaying combined images to the surgeon (18) via surgeon's console (16).

Figure 2:
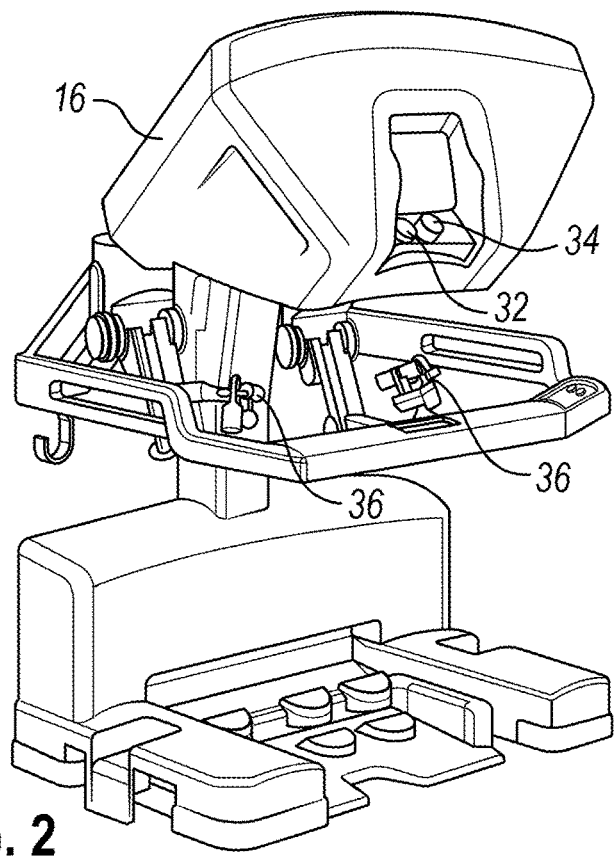
FIG. 2 depicts a perspective view of a surgeon's control console of the robotic surgical system of FIG. 1.

FIG. 2 shows a perspective view of surgeon's console (16). Surgeon's console (16) includes a left eye display (32) and a right eye display (34) for presenting surgeon (18) with a coordinated stereo view of the surgical site that enables depth perception. Surgeon's console (16) includes one or more input control devices (36) causing patient side cart (22) (shown in FIG. 1) to manipulate one or more surgical instruments (26). Input control devices (36) may provide the same degrees of freedom as their associated surgical instruments (26) (shown in FIG. 1) to provide surgeon (18) with telepresence, or the perception that the input control devices (36) are integral with surgical instruments (26). To this end, position, force, and tactile feedback sensors (not shown) may be employed to transmit position, force, and tactile sensations from surgical instruments (26) back to the surgeon's hands through input control devices (36). In some instances, surgeon's console (16) may be located in the same room as the patient so that surgeon (18) may directly monitor the procedure, be physically present if necessary, and speak to an assistant directly rather than over the telephone or other communication medium. Alternatively, surgeon (18) may be located in a different room, a completely different building, or other remote location from the patient allowing for remote surgical procedures.

Figure 3:
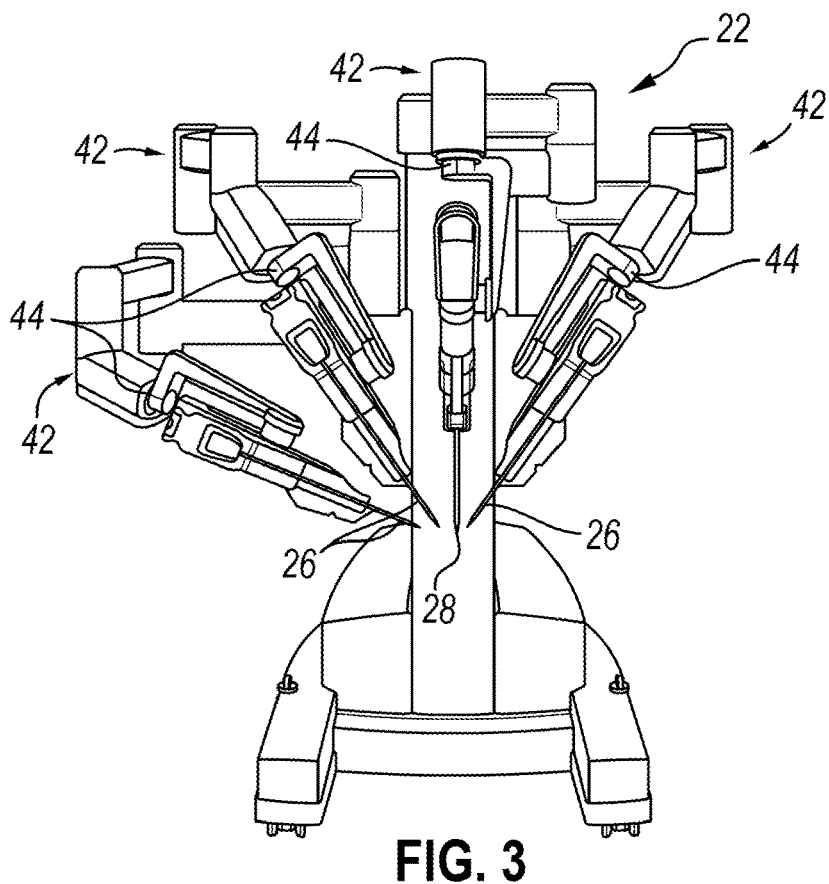
FIG. 3 depicts a front elevation view of a patient side cart of the robotic surgical system of FIG. 1.

FIG. 3 shows patient side cart (22) that manipulates surgical instruments (26). An image of the surgical site may be obtained by endoscope (28), which may include a stereoscopic endoscope. Manipulation is provided by robotic mechanisms, shown as robotic arms (42) that include at least one robotic joint (44) and an output coupler (not shown) that is configured to removable secure surgical instrument (26) with robotic arm (42). Endoscope (28) and surgical tools (26) may be positioned and manipulated through incisions in the patient so that a kinematic remote center is maintained at the incision to minimize the size of the incision. Images of the surgical site may include images of the distal ends of the surgical instruments (26) when they are positioned within the field-of-view of the endoscope (28). Patient side cart (22) may output the captured images for processing outside electronics cart (24). The number of surgical instruments (26) used at one time will generally depend on the diagnostic or surgical procedure and the space constraints within the operating room, among other factors. To change one or more of surgical instruments (26) being used during a procedure, assistant(s) (20) may remove surgical instrument (26) from patient side cart (22) and replace surgical instrument (26) with another surgical instrument (26) from a tray (30) (shown in FIG. 1) in the operating room.

B. Exemplary Surgical Instrument

Figure 4:
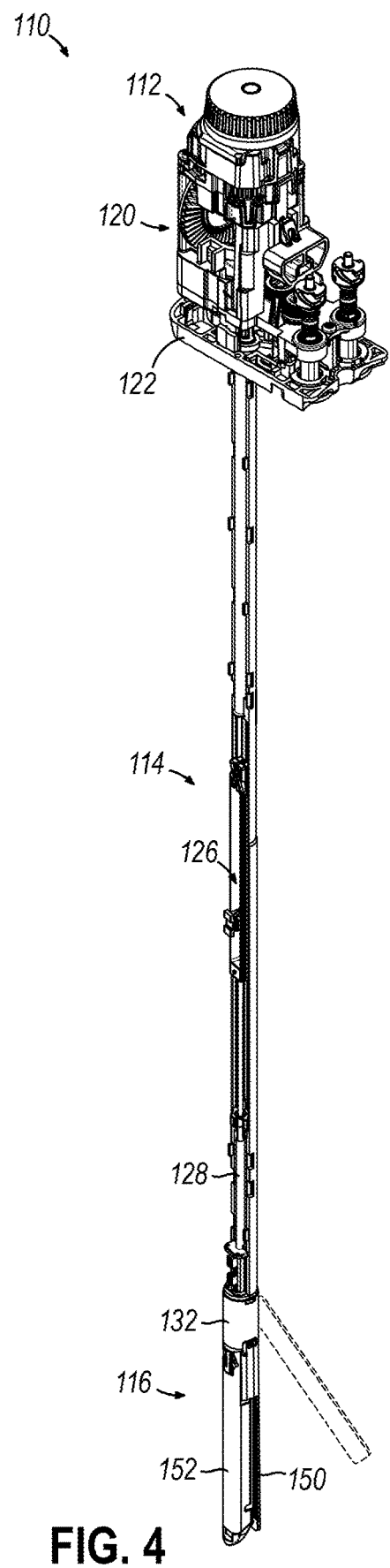
FIG. 4 depicts a perspective view of an exemplary surgical instrument that may be used with the robotic surgical system of FIG. 1, where the surgical instrument includes an instrument base, an elongate shaft, and an end effector, with select portions of the surgical instrument omitted to reveal internal features.
Figure 5:
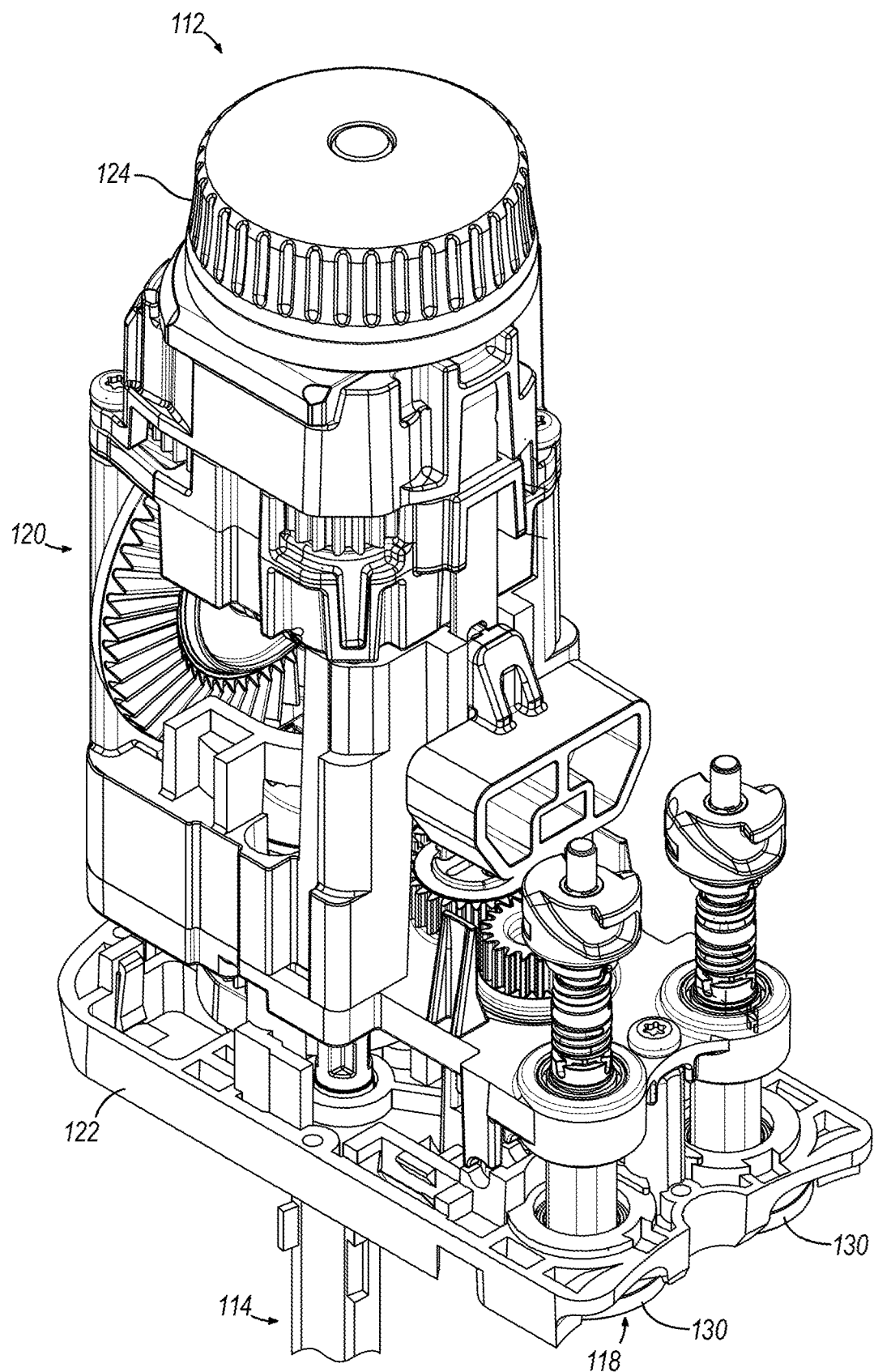
FIG. 5 depicts an enlarged perspective view of the instrument base of the surgical instrument of FIG. 4, with an outer housing omitted to reveal internal features.

FIGS. 4-5 show an exemplary surgical instrument (110) that may be mounted on and used with patient side cart (22) shown in FIG. 3. Surgical instrument (110) can have any of a variety of configurations capable of performing one or more surgical functions. As shown, surgical instrument (110) includes an instrument base (112), a shaft assembly (114) extending distally from instrument base (112), and an end effector (116) at a distal end of shaft assembly (114).

Instrument base (112) includes an attachment interface (118) that includes input couplers (130) that are configured to interface with and be driven by corresponding output couplers (not shown) of robotic arm (42) of patient side cart (22).

FIG. 5 shows an enlarged perspective view of instrument base (112) of surgical instrument (110). Instrument base (112) includes a drive system (120) mounted on a chassis (122) and having one or more actuators for actuating end effector (116) to clamp, staple, and cut tissue, and for articulating end effector (116) relative to a longitudinal axis defined by shaft assembly (114). Drive system (120) may include a manual actuator (124), which is shown in the form of a knob configured to be manually rotated. Manual actuator (124) may engage other components of surgical instrument (110) to serve as a "bailout" mechanism to obtain a desired movement in end effector (116) without powered actuation of drive system (120). Shaft assembly (114) may include additional drive components, such as portions of a drive train (126), that may couple instrument base (112) to a moveable feature (128) of shaft assembly (114) that may be coupled to end effector (116). Shaft assembly (114) may be configured for use with a variety of interchangeable end effectors (116), such as a cutter, grasper, a cautery tool, a camera, a light, or a surgical stapler, for example.

C. First Exemplary End Effector

Figure 6:
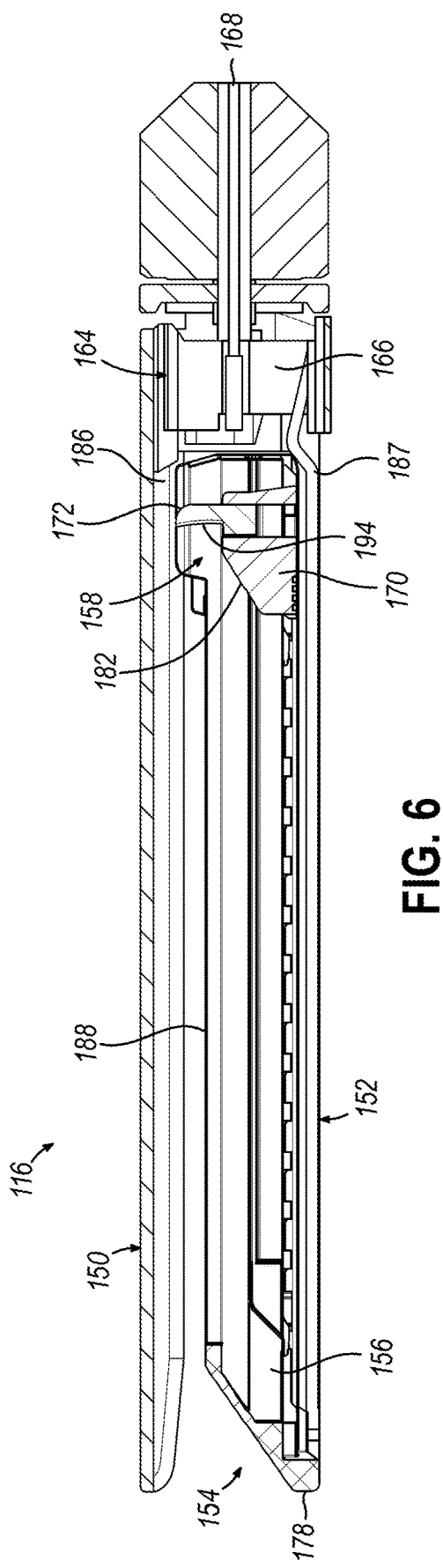
FIG. 6 depicts a side cross-sectional view of the end effector of FIG. 4, where the end effector includes a staple cartridge.

FIG. 6 shows a cross-sectional side view of end effector (116) of surgical instrument (110). End effector (116) extends distally from a distal end of shaft assembly (114). In the present example, end effector (116) comprises a surgical stapler, which may also be referred to herein as an "endocutter," configured to clamp, cut, and staple tissue. As illustrated, end effector (116) includes opposing upper and lower jaws (150, 152) configured to move relative to one another between open and closed positions for clamping and releasing tissue.

One or both of upper and lower jaws (150, 152) may be configured to pivot and thereby actuate end effector (116) between open and closed positions. Lower jaw (152) includes a removable staple cartridge (154). In the illustrated example, lower jaw (152) is pivotable relative to upper jaw (150) to move between an open, unclamped position and a closed, clamped position. In other examples, upper jaw (150) may move relative to lower jaw (152) (e.g., similar to end effector (210) of FIGS. 9-10). In still other examples, both and upper and lower jaws (150, 152) may move to actuate end effector (116) between open and closed positions. In the present example, lower jaw (152) is referred to as a "cartridge jaw" or "channel jaw," and upper jaw (150) is referred to as an "anvil jaw."

Figure 8:
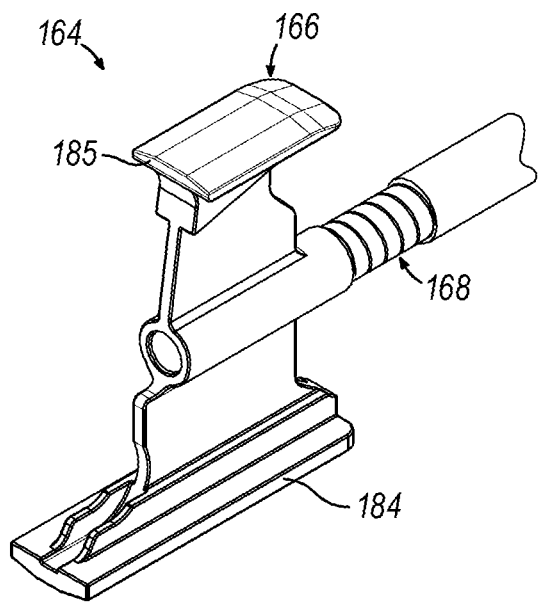
FIG. 8 depicts a driving assembly configured for use with the staple cartridge of FIG. 7.
Figure 9:
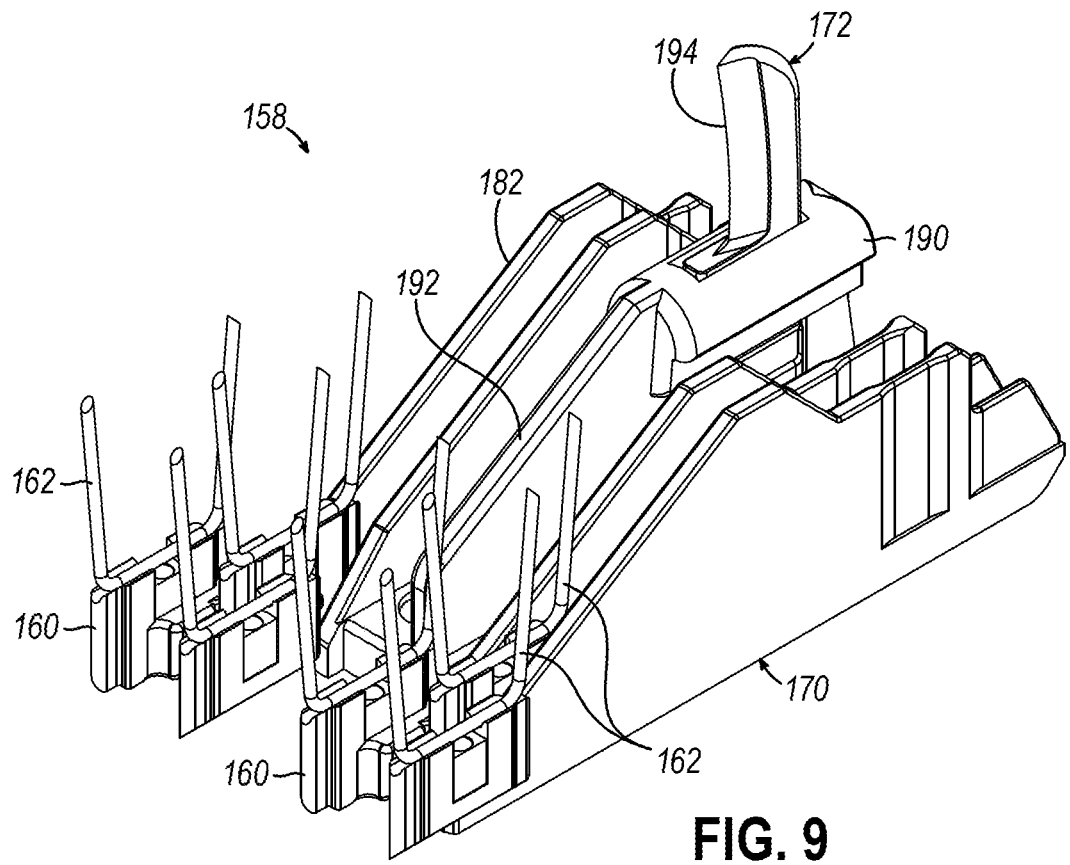
FIG. 9 depicts a firing assembly, staple drivers, and staples configured for use with the staple cartridge of FIG. 7.

Upper jaw (150) defines a surface that has a plurality of pockets (not shown) and operates as an anvil to deform staples ejected from staple cartridge (154) during operation. Staple cartridge (154) is replaceable, for example, by removing a used staple cartridge (154) from end effector (116) and inserting a new staple cartridge (154) into lower jaw (152). Staple cartridge (154) includes a staple cartridge body (156) that houses a firing assembly (158), a plurality of staple drivers (160) (also referred to as staple pushers), and a plurality of staples (162). As shown in FIGS. 6 and 8, end effector (116) includes a driving assembly (164) that includes a pusher member (166) that is operatively coupled with an actuation mechanism via a push rod (168). As shown in FIG. 6 and FIG. 9, firing assembly (158) includes a wedge sled (170) (also referred to as a staple pushing shuttle), and a knife member (172).

Figure 7:
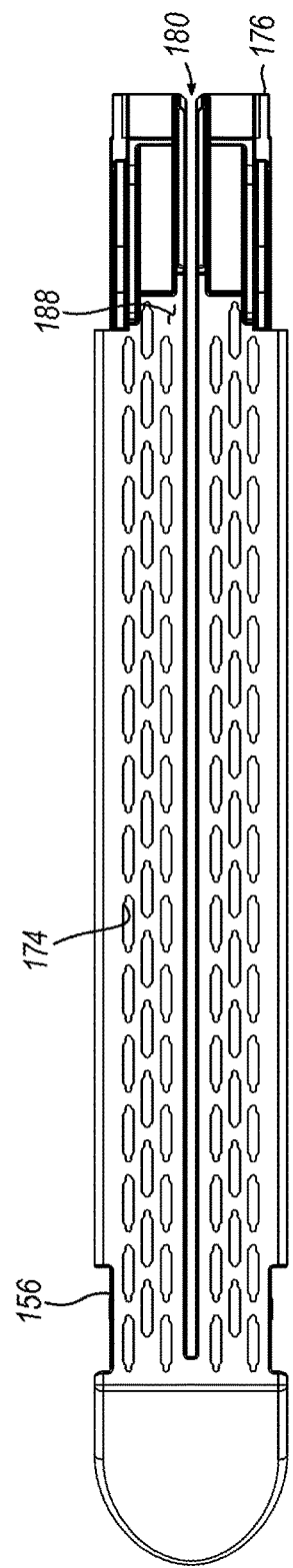
FIG. 7 depicts a top view of a deck of the staple cartridge of FIG. 6.

FIG. 7 shows a top view of staple cartridge body (156). Staple cartridge body (156) includes an array of staple accommodating apertures (174) (also known as openings) extending through an upper deck (188) of staple cartridge body (156). Each aperture (174) slidably houses a respective staple (162) in an unformed state and a free end of a corresponding staple driver (160) positioned beneath the unformed staple (162). Staple cartridge (154) includes proximal and distal ends (176, 178). In operation, staples (162) are sequentially deployed from apertures (174) by staple drivers (160) starting at proximal end (176) and advancing toward distal end (178). A vertical slot (180), configured to accommodate knife member (172), extends through part of staple cartridge (154).

FIG. 8 shows pusher member (166) as including first and second flanges (184, 185). First flange (184) is configured to be received in a longitudinal slot (186) (shown in FIG. 6) of upper jaw (150) and second flange (185) is configured to be received in a longitudinal slot (187) (shown in FIG. 6) of staple cartridge body (156) of lower jaw (152). First and second flanges (184, 185) move along longitudinal slots (186, 187) during actuation of pusher member (166). In some versions, pusher member (166) may include a single flange (e.g., omitting first flange (184)). As shown, longitudinal slot (186) is generally enclosed and longitudinal slot (187) opens to an exterior surface of lower jaw (152).

FIG. 9 shows a perspective view of firing assembly (158), which is configured to be slidably received within the proximal end of staple cartridge body (156) in a longitudinal direction prior to engaging staple drivers (160) and staples (162). Wedge sled (170) of firing assembly (158) slidingly interfaces with staple cartridge body (156). More specifically, wedge sled (170) advances distally along staple cartridge body (156) such that ramp portions (182) of wedge sled contact staple drivers (160). Staple drivers (160) push staples (162) out of apertures (174) of staple cartridge body (156) to penetrate through and staple tissue clamped between staple cartridge body (156) and upper jaw (150). An initial distal actuation of pusher member (166) may move pusher member (166) into contact with wedge sled (170), with further actuation pushing staples (162) transversely out of staple cartridge body (156).

At an initial proximal position of wedge sled (170), knife member (172) is housed within staple cartridge body (156). The position of knife member (172) is controlled during a first portion of the movement of wedge sled (170) from proximal end (176) of staple cartridge body (156) to distal end (178) of staple cartridge (154), so that a cutting edge (194) of knife member (172) extends through vertical slot (180). Vertical slot (180) accommodates cutting edge (194) of knife member (172) as firing assembly (158) is moved toward distal end (178) of staple cartridge (154). Wedge sled (170) includes a guide member (190) that provides a bearing surface that cooperates with a similarly shaped surface of staple cartridge body (156) to guide wedge sled (170). Guide member (190) extends from a vertical rib member (192) of wedge sled (170), which forms a central portion of wedge sled (170). In some versions, knife member (172), or at least cutting edge (194), may be retracted below upper deck (188) of staple cartridge body (156) prior to firing assembly (158) reaching its distal most position adjacent to distal end (178) of staple cartridge (154).

D. Second Exemplary End Effector

Figure 10:
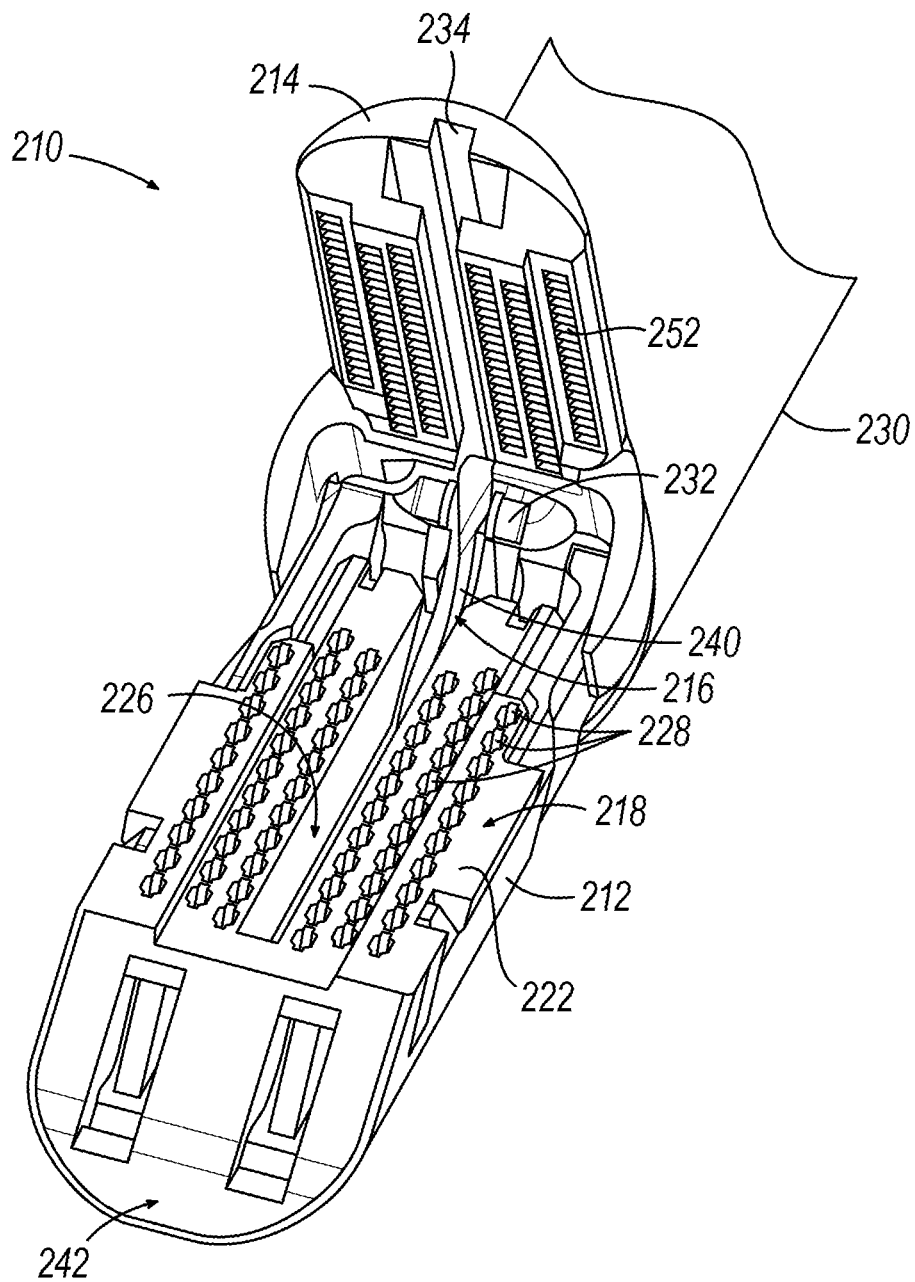
FIG. 10 depicts a second exemplary end effector that may be configured for use with the robotic surgical system of FIG. 1.
Figure 11:
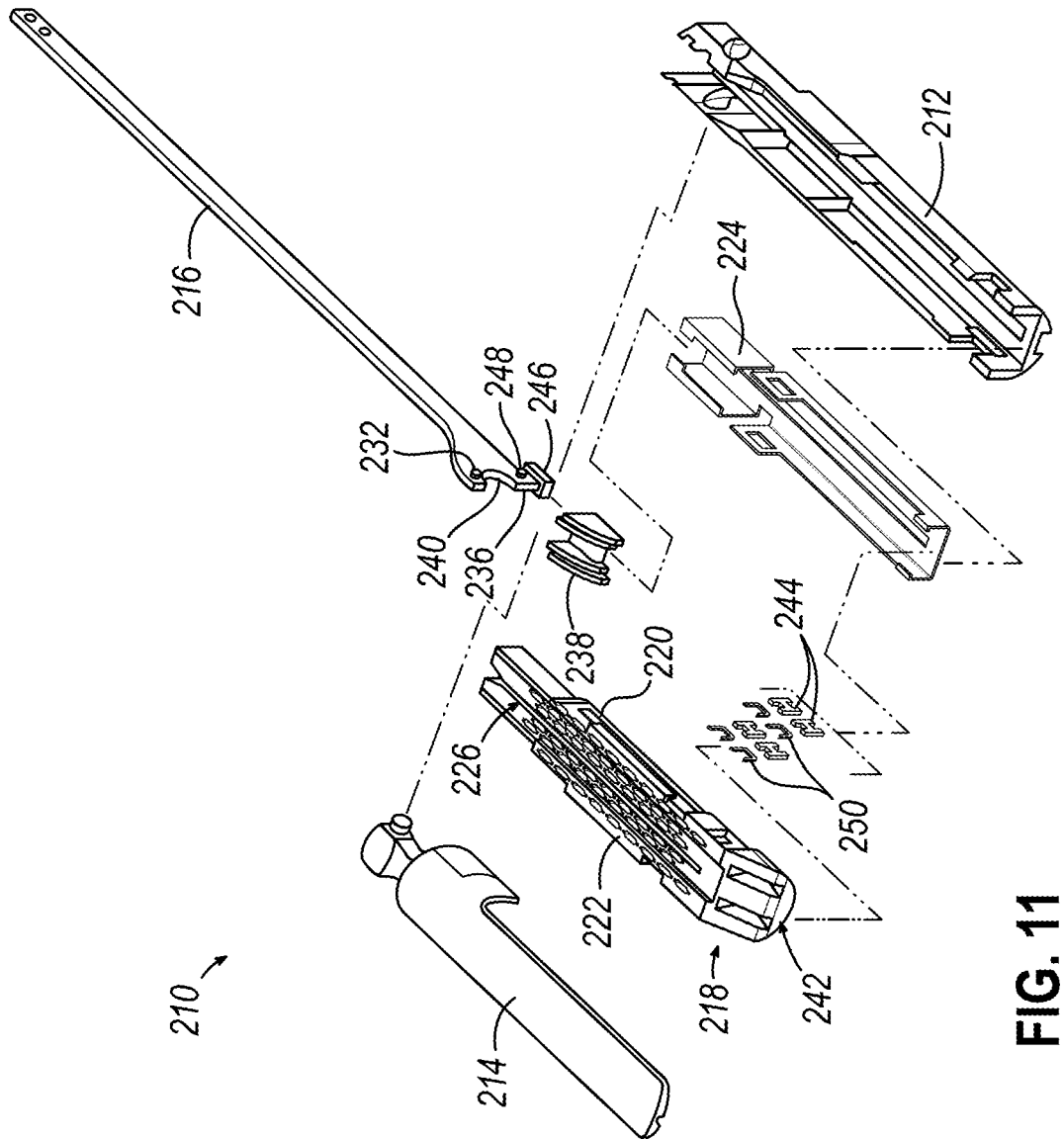
FIG. 11 depicts an exploded view of the end effector of FIG. 10.

FIGS. 10-11 show a second exemplary end effector (210), in an open position, that is configured to compress, cut, and staple tissue. End effector (210) may be configured for use with surgical instrument (110) of FIG. 4, or with surgical instruments of alternative constructions. End effector (210) may be constructed and operable in accordance with at least some of the teachings of U.S. patent application Ser. No. 16/916,295, entitled "Surgical Stapler Cartridge Retainer with Ejector Feature," filed Aug. 3, 2020, issued as U.S. Pat. No. 11,497,494 on Nov. 15, 2022, the disclosure of which is incorporated by reference herein in its entirety. End effector (210) of the present example includes a lower jaw (212) and an upper jaw in the form of a pivotable anvil (214). Lower jaw (212) may be constructed and operable in accordance with at least some of the teachings of U.S. Pat. No. 9,808,248, entitled "Installation Features for Surgical Instrument End Effector Cartridge," issued Nov. 7, 2017, the disclosure of which is incorporated by reference herein in its entirety. Anvil (214) may be constructed and operable in accordance with at least some of the teachings of U.S. Pat. No. 10,092,292, entitled "Staple Forming Features for Surgical Stapling Instrument," issued Oct. 9, 2018, the disclosure of which is incorporated by reference herein in its entirety.

FIG. 10 shows end effector (210), where anvil (214) is pivoted to an open position and a firing beam (216) is proximally positioned, allowing an unspent staple cartridge (218) to be removably installed into a channel of lower jaw (212). Staple cartridge (218) includes a cartridge body (220), which presents an upper deck (222) and is coupled with a lower cartridge tray (224). A vertical slot (226) is formed through part of staple cartridge (218) and opens upwardly through upper deck (222). One or more rows of staple apertures (228) are formed through upper deck (222) on one side of vertical slot (226), with one or more rows of staple apertures (228) being formed through upper deck (222) on the other side of vertical slot (226). End effector (210) is closed by distally advancing a closure tube (not shown) and a closure ring (230). Firing beam (216) is then advanced distally so that an upper pin of firing beam (216) enters longitudinal anvil slot (234). Simultaneously, a pusher block (236) located at the distal end of firing beam (216) engages a wedge sled (238) housed within cartridge body (220), such that wedge sled (238) is pushed distally by pusher block (236) as firing beam (216) is advanced distally through staple cartridge (218) and anvil (214).

During firing, cutting edge (240) of firing beam (216) enters vertical slot (226) toward distal end (242) of staple cartridge (218), severing tissue clamped between staple cartridge (218) and anvil (214). As best seen in FIG. 11, wedge sled (238) presents inclined cam surfaces that urge staple drivers (244) upwardly as wedge sled (238) is driven distally through staple cartridge (218). A firing beam cap (246) slidably engages a lower surface of lower jaw (212). Wedge sled (238) is movable longitudinally within staple cartridge (218), while staple drivers (244) are movable vertically within staple cartridge (218). A middle pin (248) and pusher block (236) of firing beam (216) together actuate staple cartridge (218) by entering into vertical slot (226) within staple cartridge (218), driving wedge sled (238) distally into upward camming contact with staple drivers (244) that in turn drive staples (250) out through staple apertures (228) and into forming contact with staple forming pockets (252) on the inner surface of anvil (214). Additional examples of alternative surgical instruments and/or associated features are described in U.S. patent application Ser. No. 16/946,363, entitled "Articulation Mechanisms for Robotic Surgical Tools," filed on Jun. 18, 2020, issued as U.S. Pat. No. 11,896,202 on Feb. 13, 2024, the disclosure of which is hereby incorporated by reference herein in its entirety.

It will be appreciated that any one or more of the teachings described below may be combined with any one or more of the teachings described above in connection with FIGS. 1-11.

II. Exemplary Drive Systems for Surgical Instrument

A. Exemplary Drive System

Figure 12:
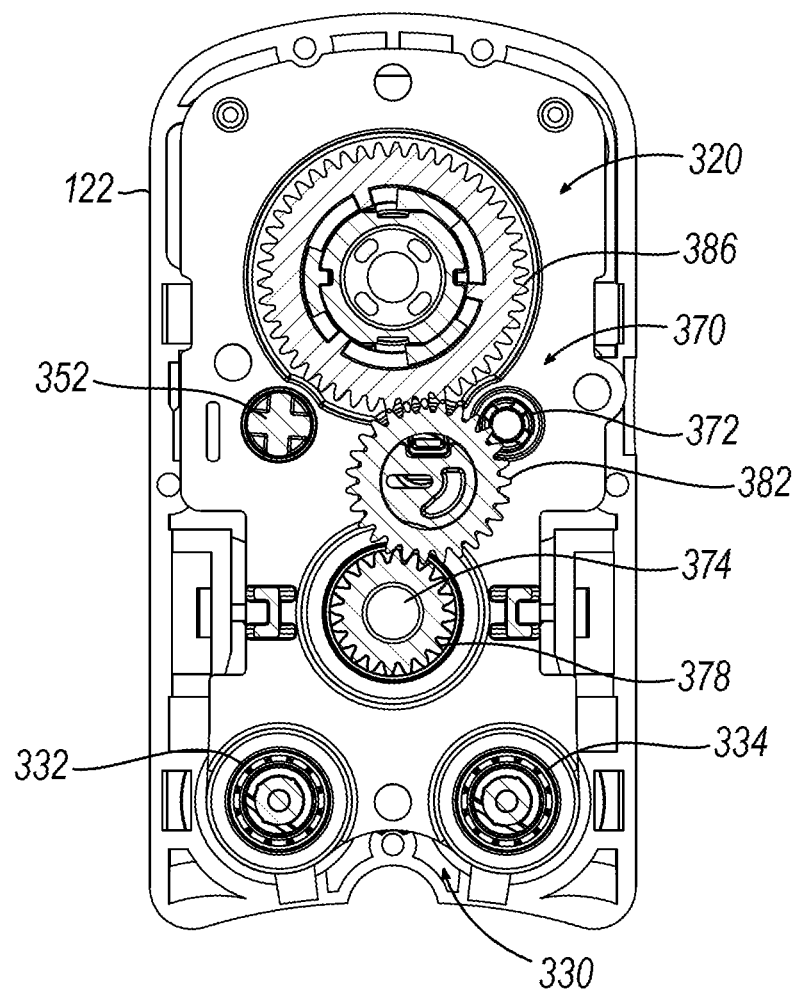
FIG. 12 depicts a top plan view of an exemplary drive system that may be used with the surgical instrument of FIG. 4.
Figure 13:
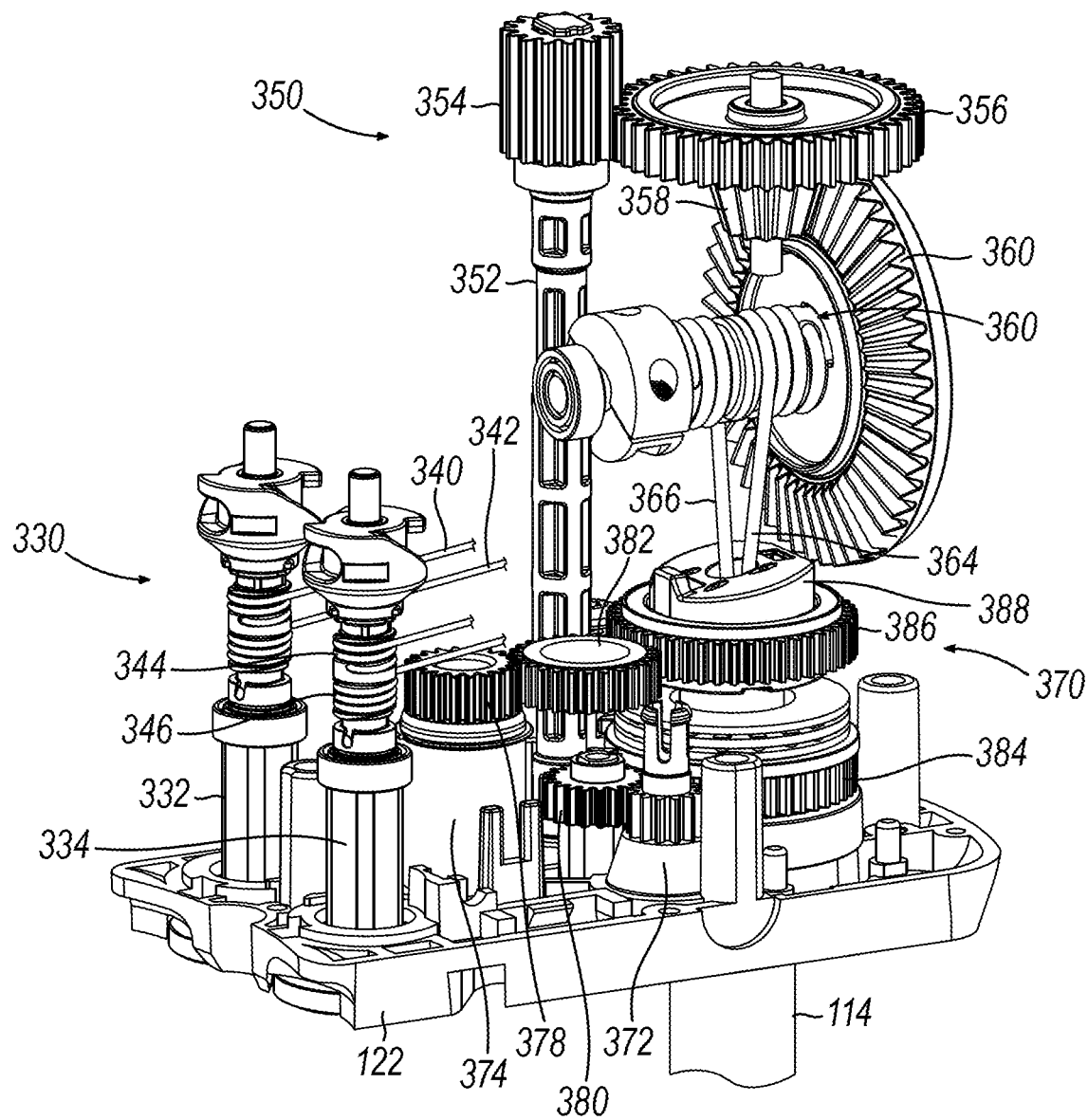
FIG. 13 depicts a perspective view of the drive system of FIG. 12.

FIGS. 12 and 13 show an exemplary drive system (320) that may be readily incorporated into surgical instrument (110) described above in lieu of drive system (120). As with drive system (120) described above, drive system (320) of the present example is mounted to chassis (122) of instrument base (112). Similarly, drive system (320) includes one or more actuators for actuating end effector (116) to clamp, staple, and cut tissue, for rotating end effector (116) and/or shaft assembly (114), and for articulating end effector (116) relative to a longitudinal axis defined by shaft assembly (114). Drive system (320) may also include a manual actuator (not shown) similar to manual actuator (124) described above, which may be in the form of a knob configured to be manually rotated.

As best seen in FIG. 12, drive system (320) of the present example includes a plurality of drive inputs (332, 334, 352, 372, 374), which may extend through chassis (122) and into the interior of surgical instrument (110). Although not shown, it should be understood that each drive input (332, 334, 352, 372, 374) is configured to communicate with a corresponding drive output (not shown) of robotic arm (42) to transmit rotary input from robotic arm (42) to other portions of surgical instrument (110). Each drive input (332, 334, 352, 372, 374) of the present example is associated with one or more drive modules (330, 350, 370) to control various functions of surgical instrument (110) as will be described in greater detail below.

Drive system (320) of the present example includes an articulation drive module (330), an actuation drive module (350), and a rotation drive module (370). Drive modules (330, 350, 370) are together configured to drive movement of one or more of end effector (116) and or shaft assembly (114), as will be described in greater detail below. For instance, articulation drive module (330) is generally configured to drive articulation of end effector (116) relative to a longitudinal axis defined by shaft assembly (114). Actuation drive module (350) is generally configured to drive actuation of end effector (116) to clamp, staple, and cut tissue. Rotation drive module (370) is generally configured to rotate one or more components of shaft assembly (114) and/or components associated therewith.

Articulation module (350) includes a first articulation drive input (332) and a second articulation drive input (334). Each of first articulation drive input (332) and second articulation drive input (334) define a shaft extending proximally from chassis (122) and into the interior of surgical instrument (110). Although not shown, it should be understood each of first articulation drive input (332) and second articulation drive input (334) may be configured to engage a drive output (not shown) of robotic arm (42) to rotate via one or more motors associated with robotic arm (42). As will be understood, such rotation may be desirable to manipulate one or more articulation cables (340, 342, 344, 346) to control articulation of end effector (116) relative to shaft assembly (114) using articulation drive inputs (332, 334).

A first articulation capstan (336) and a second articulation capstan (338) are disposed proximate a proximal end of first articulation drive input (332) and second articulation drive input (334), respectively. Articulation capstans (336, 338) are generally configured to simultaneously tension and release a respective set of articulation cables (340, 342, 344, 346) to control articulation of end effector (116) relative to shaft assembly (114). As such each of articulation capstans (336, 338) are configured as dual-capstans to permit each respective articulation cable (340, 342, 344, 346) to be opposingly threaded relative to another articulation cable (340, 342, 344, 346). Although not shown, it should be understood that articulation cables (340, 342, 344, 346) may extend from each articulation capstan (336, 338) and through shaft assembly (114) to communicate with various features configured to drive articulation of end effector (116) relative to shaft assembly (114).

Actuation drive module (350) includes an actuation drive input (352). Actuation drive input (352) defines an elongate shaft extending proximally from chassis (122) and into the interior of surgical instrument (110). Although not shown, it should be understood that actuation drive input (352) may be configured to engage a drive output (not shown) of robotic arm (42) to rotate via one or more motors associated with robotic arm (42). As will be understood, such rotation may be desirable to manipulate one or more actuation cables (364, 366) to control actuation of end effector (116) and other components associated with end effector (116) to clamp, staple, and cut tissue using actuation drive input (352).

A proximal end of actuation drive input (352) includes an actuation drive gear (354). Actuation drive gear (354) is configured to rotate with actuation drive input (352) to move other components of actuation drive module (350). In particular, actuation drive gear (354) is configured to mesh with an idler gear (356), which is configured to mesh with a capstan gear (360) to drive movement of an actuation capstan (362). Idler gear (356) further includes a bevel gear (358) that is configured to directly mesh with capstan gear (360), thereby permitting a different orientation of capstan gear (360) relative to idler gear (356).

Actuation capstan (362) is generally configured to simultaneously tension and release a set of actuation cables (364, 366) to control movement of end effector (116) and other components associated with end effector (116) to clamp, staple, and cut tissue. In particular, actuation drive module (350) further includes a first actuation cable (364) and a second actuation cable (366). First actuation cable (364) and second actuation cable (366) are wrapped in opposing directions around actuation capstan (362) such that rotation of actuation capstan (362) may cause one actuation cable (364, 366) to tension and the other actuation cable (366, 364) to release, depending on the direction of rotation of actuation capstan (362). Actuation cables (364, 366) extend distally from actuation capstan (362) into shaft assembly (114). Although not shown, it should be understood that actuation cables (364, 366) may couple to other components within shaft assembly (114) to control movement of end effector (116) and other components associated with end effector (116) to clamp, staple, and cut tissue via rotation of actuation drive input (352).

Rotation drive module (370) includes a primary rotation drive input (372) and a secondary rotation drive input (374). Primary rotation drive input (372) and secondary rotation drive input (374) each define a shaft extending proximally from chassis (122) and into the interior of surgical instrument (110). The particular length of extension for primary rotation drive input (372) is different from secondary rotation drive input (374) to promote driving of different elements of rotation drive module (370) via primary rotation drive input (372) or secondary rotation drive input (374). In the present example, the length of extension for secondary rotation drive input (374) is longer than the length of extension of primary rotation drive input (372). Although not shown, it should be understood that each of primary rotation drive input (372) and secondary rotation drive input (374) may be configured to engage a respective drive output (not shown) of robotic arm (42) to rotate via one or more motors associated with robotic arm (42). As will be understood, such rotation may be desirable to manipulate one or more components associated with shaft assembly (114) to rotate shaft assembly (114) and/or components associated therewith using primary rotation drive input (372) and secondary rotation drive input (374).

A proximal end of each rotation drive input (372, 374) includes a respective rotation drive gear (376, 378) configured to communicate rotary motion of a respective rotation drive input (372, 374) to other components of rotation drive module (370). For instance, primary rotation drive input (372) includes a primary rotation drive gear (376). Primary rotation drive gear (376) is in communication with a primary idler gear (380), which is in communication with a primary rotation input (384). Primary rotation input (384) is coupled to shaft assembly (114) such that rotation of primary rotation input (384) is configured to drive rotation of shaft assembly (114). Thus, it should be understood that primary rotation drive input (372) is configured to rotate shaft assembly (114) by rotating primary rotation drive gear (376), which rotates primary idler gear (380), which rotates primary rotation input (384) to ultimately rotate shaft assembly (114).

Secondary rotation drive input (374) includes a secondary rotation drive gear (378). Secondary rotation drive gear (378) is in communication with a secondary idler gear (382), which is in communication with a secondary rotation input (386). Secondary rotation input (386) is secured or otherwise in communication with a cable manipulator (388). Cable manipulator (388) includes one or more openings configured to direct and/or manipulate any one or more of cables (340, 342, 344, 346, 364, 366) described above. Thus, cable manipulator (388) is generally configured to rotate with shaft assembly (114) to maintain separation and alignment of cables (340, 342, 344, 346, 364, 366) or otherwise avoid entanglement of cables (340, 342, 344, 346, 364, 366). Accordingly, secondary rotation drive input (374) is generally configured to control the position of cables (340, 342, 344, 346, 364, 366) during rotation of shaft assembly (114) by rotating cable manipulator (388) using secondary rotation drive gear (374), secondary idler gear (382), and secondary rotation input (386).

In use, drive inputs (332, 334, 352, 372, 374) may be rotated in various sequences by one or more motors within robotic arm (42) to control various functions of surgical instrument (110). For instance, in one merely exemplary use, first articulation drive input (332) and second articulation drive input (334) may be rotated together or independently to articulate end effector (116) relative to a longitudinal axis defined by shaft assembly (114). Such movement may be used to manipulate end effector (116) into a predetermined position relative to a patient. In some examples, articulation may include both pitch and yaw articulation with one articulation drive input (332, 334) controlling pitch, and another articulation drive input (334, 332) controlling yaw.

While positioning end effector (116), it may also be desirable to rotate shaft assembly (114) to provide further control of the position of end effector (116) relative to a patient. Such rotation of shaft assembly (114) may be controlled by rotation drive module (370) by rotating primary rotation drive input (372) and/or secondary rotation drive input (374) either together or independently. For instance, rotation of primary rotation drive input (372) may be used to rotate shaft assembly (114) itself. Meanwhile, rotation of secondary rotation drive input (374) may be used to control rotation of cable manipulator (388) to maintain cables (340, 342, 344, 346, 364, 366) in a desired arrangement or position relative to each other during rotation of shaft assembly (114).

Once end effector (116) is in a desired position relative to a patient, it may be desirable to use end effector (116) for the purpose of clamping, stapling, and/or cutting tissue. At this stage, end effector (116) may be further manipulated using articulation drive inputs (332, 334) and/or rotation drive inputs (372, 374) as described above to position end effector (116) relative to tissue of interest. Simultaneously or independently of such manipulation of the position of end effector (116), jaws (150, 152), wedge sled (170), and/or other components of end effector (116) may be actuated using actuation drive module (350) to clamp, staple, and/or cut the tissue of interest. Specifically, actuation drive input (352) may be rotated to manipulate actuation assembly, also referred to as driving assembly (164) of end effector (116) via actuation cables (364, 366). Such manipulation of actuation assembly (164) may then cause, for example, opening and/or closing of jaws (150, 152) for tissue clamping, translation of wedge sled (170) for tissue stapling, and/or translation of knife member (172) for tissue cutting.

B. Exemplary Alternative Drive System with Adjustable Tension Bands

In some examples, it may be desirable to incorporate a drive system similar to drive system (310) described above into surgical instrument (110) with various features to improve operation of surgical instrument (110), improve the efficiency of surgical instrument (110), and/or improve the simplicity or adaptability of surgical instrument (110). For instance, in some examples, it may be desirable to control multiple functions of surgical instrument (110) using a single drive input. In addition, or in the alternative, it may be desirable to control multiple aspects of the same function of surgical instrument (110) using a single drive input. Configurations of such drive systems controlling multiple functions and/or multiple aspects of the same function of surgical instrument (110) may be desirable to reduce the number of motors used to drive surgical instrument (110) such as those in robotic arm (42). Thus such configurations may improve the efficiency of surgical instrument (110), may make surgical instrument (110) more adaptable, and/or may generally simplify surgical instrument (110).

Further in addition, or in the alternative, it may be desirable to incorporate features into such drive mechanisms to provide control over the mechanical advantage communicated to one or more functions of surgical instrument (110) from such drive systems. For instance, during use of some functions, it may be desirable to actuate surgical instrument (110) with a preference for either speed or power. Thus, features to provide selectability between either speed or power for actuation may be desirable to improve overall operation of surgical instrument (110) or to improve the efficiency of surgical instrument (110). While a variety of suitable drive mechanisms are described below as including such features in specific configurations, it should be understood that in other examples such features may be combined in different configurations without departing from the various concepts described herein.

Figure 14B:
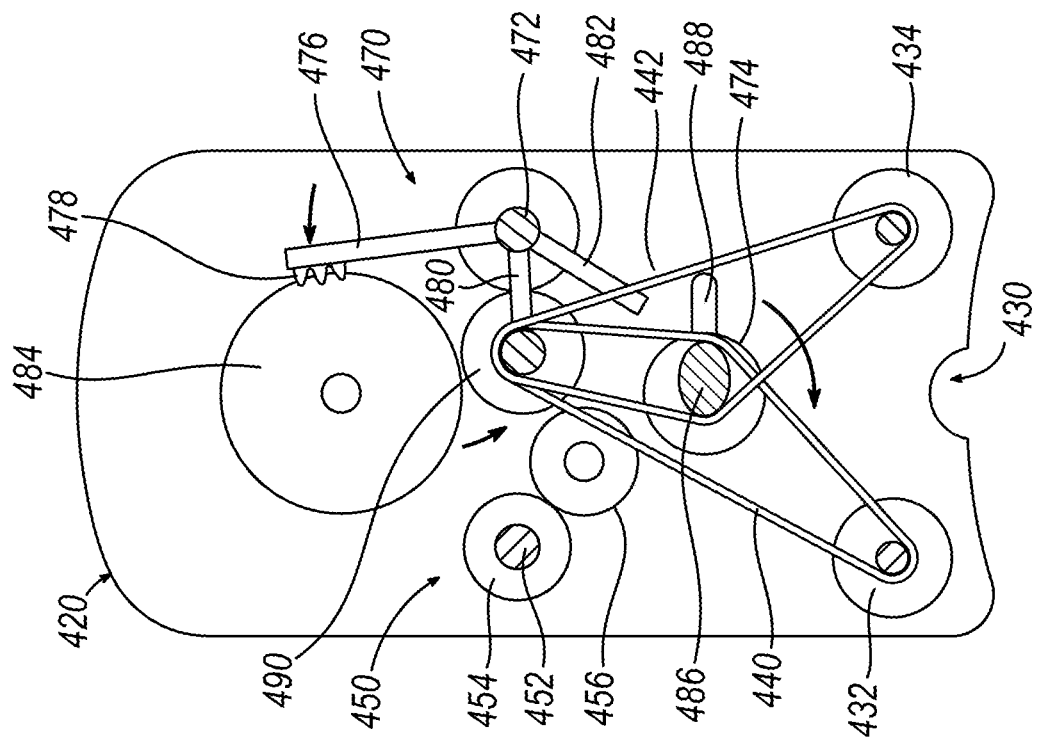
FIG. 14B depicts another top plan view of the drive system of FIG. 14A, the drive system in a first multiple drive configuration.
Figure 14A:
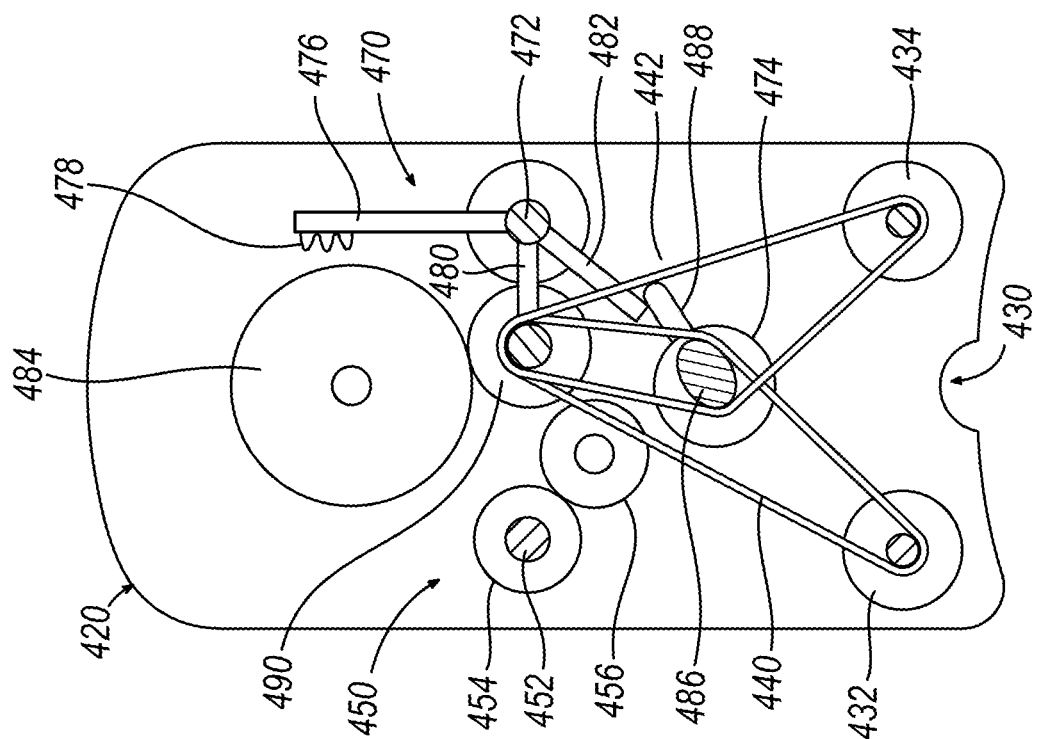
FIG. 14A depicts a top plan view of an exemplary alternative drive system that may be used with the surgical instrument of FIG. 4, the drive system in a single drive configuration.

FIG. 14A shows an exemplary alternative drive system (420) that may be readily incorporated into surgical instrument described above. Drive system (420) of the present example is similar to drive system (320) described above in that drive system (420) of the present example is generally configured to receive external rotary inputs to drive one or more actuators for actuating end effector (116) to clamp, staple, and cut tissue, for rotating end effector (116) and/or shaft assembly (114), and for articulating end effector (116) relative to a longitudinal axis defined by shaft assembly (114). Drive system (420) may also include a manual actuator (not shown) similar to manual actuator (124) described above, which may be in the form of a knob configured to be manually rotated.

Like drive system (320) described above, drive system (420) of the present example includes one or more drive modules (430, 450, 470) configured to drive various functions of surgical instrument (110). Unlike drive modules (330, 350, 370) described above, which were described as being operable independently of each other, drive modules (430, 450, 470) of the present example are interconnected with each other. As will be described in greater detail below, this configuration may be generally desirable to selectively permit multiple motors to drive a single function of surgical instrument (110) and thereby increase the mechanical advantage provided to a given function of surgical instrument (110).

Drive system (420) includes an articulation drive module (430), an actuation drive module (450), and a rotation drive module (470). Articulation drive module (430) is similar to articulation drive module (330) described above in that articulation drive module (430) includes a first articulation drive input (432) and a second articulation drive input (434). Although not shown, it should be understood that drive inputs (432, 434) may likewise each include a respective articulation capstan (not shown) similar to articulation capstans (336, 338) described above. Like articulation capstans (336, 338), such articulation capstans in the present example may be configured to selectively tension one or more respective articulation cables similar to articulation cables (340, 342, 344, 346) described above to ultimately control movement of end effector (116) relative to a longitudinal axis defined by shaft assembly (114).

Unlike articulation drive module (330) described above, articulation drive module (430) of the present example includes one or more drive bands (440, 442) extending from articulation drive module (430) to one or more other drive modules (450, 470). Drive bands (440, 442) are generally configured to communicate power from one or more of drive inputs (432, 434) to one or more other drive modules (450, 470) or receive power from one or more other drive modules (450, 470). Thus, drive bands (440, 442) may be generally configured to shift power between drive modules (430, 450, 470) to selectively increase the mechanical advantage of a given function of surgical instrument (110). In addition, or in the alternative, drive bands (440, 442) may be generally configured to shift power between drive modules (430, 450, 470) to power multiple functions of surgical instrument (110) to eliminate one or more drive inputs and instead use only drive inputs (432, 434) or drive inputs (432, 434) in combination with other drive inputs described below.

Actuation drive module (450) of the present example is similar to actuation drive module (350) described above in that actuation drive module (450) includes an actuation drive input (452) configured to engage a drive output of robotic arm (42) to control actuation of end effector (116) and other components associated with end effector (116) to clamp, staple and cut tissue. To promote such functionality, actuation drive input (452) includes an actuation drive gear (454), which is configured to mesh with an idler gear (456). Although not shown, it should be understood that idler gear (456) may mesh or otherwise communicate with one or more structures similar to bevel gear (358), capstan gear (360), actuation capstan (362). As similarly described above, such structures may permit actuation drive input (452) to rotate an actuation capstan (not shown) to selectively tension/release one or more actuation drive cables (not shown) similar to actuation drive cables (364, 366) described above. The actuation drive cables may then communicate with structures associated with end effector (116) to clamp, staple and cut tissue.

Unlike actuation drive module (350) described above, actuation drive module (450) of the present example is generally configured to selectively communicate with articulation drive module (430) and/or rotation drive module (470). As will be described in greater detail below, this feature may be desirable to permit actuation drive module (450) of the present example to selectively actuate end effector (116) with increased mechanical advantage. In some examples, this may be facilitated by, for example, communicating power from first articulation drive input (432) and/or second articulation drive input (434) to actuation drive gear (452) via meshing between idler gear (456) and one or more structures associated with rotation drive module (470).

Rotation drive module (470) of the present example is similar to rotation drive module (370) described above in that rotation drive module (470) is configured to drive rotation of shaft assembly (114) of surgical instrument (110) and other components associated therewith. However, unlike rotation drive module (370) described above, rotation drive module (470) of the present example is configured to selectively divert rotary power from articulation drive inputs (432, 434) of articulation drive module (430) to other portions of either articulation drive module (430) and/or actuation drive module (450).

Rotation drive module (470) of the present example omits structures similar to primary rotation drive input (372) and secondary rotation drive input (374). Instead, rotation drive module (470) includes a drive pivot (472) and a shifting drive input (474). Drive pivot (472) is positioned similarly to primary rotation drive input (372) described above. However, instead of being configured to receive rotary input, drive pivot (472) is configured to be manipulated by other structures of rotation drive module (470) to drive either rotation of shaft assembly (114) or other functions of surgical instrument (110).

Drive pivot (472) is coupled to a lock arm (476), a pivot arm (480) and a selector arm (482). Drive pivot (472) is generally configured to permit pivoting of lock arm (476), pivot arm (480) and selector arm (482) about an axis defined by drive pivot (472). Although drive pivot (472) itself is not configured to directly provide movement of lock arm (476), pivot arm (480) and selector arm (482), it should be understood that in some examples, drive pivot (472) may be configured to manipulate such movement by providing a ratcheting action and/or biasing lock arm (476), pivot arm (480) and selector arm (482) toward one or more predetermined positions. It still other examples, drive pivot (472) may be configured to drive movement of lock arm (476), pivot arm (480), and selector arm (482) directly via rotation from one or more motors.

Drive pivot (472) is further configured as a drive input to communicate rotary motion from one or more motors in robotic arm (42) to other components of rotation drive module (470). Although drive pivot (472) is shown schematically in the present example, it should be understood that in practice at least a portion of drive pivot (472) may be configured as a gear or other feature configured to mesh or communicate rotary motion from drive pivot (472) to other portions of rotation drive module (470). As will be described in greater detail below, such communication may be used to drive rotation of shaft assembly (114) via drive pivot (472).

Lock arm (476), pivot arm (480), selector arm (482) extend outwardly from drive pivot (472). Additionally, lock arm (476), pivot arm (480) and selector arm (482) each extend at a fixed angle relative to each other. In other words, lock arm (476), pivot arm (480), and selector arm (482) are configured to pivot about drive pivot (472) while maintaining a fixed position relative to each other. Lock arm (476) includes a plurality of lock teeth (478) disposed on an outer end of lock arm (476) opposite of drive pivot (472). As will be described in greater detail below, lock teeth (478) are configured to engage primary rotation input (484) to selectively lock rotation of shaft assembly (114).

Pivot arm (480) is disposed between lock arm (476) and selector arm (482). Pivot arm includes an output gear (490) disposed on an outer end of pivot arm (480) opposite of drive pivot (472). Output gear (490) is rotatably coupled to pivot arm (480) and is in communication with first drive band (440) and second drive band (442) to rotate via drive bands (440, 442). Output gear (490) is further configured to mesh with a gear portion of drive pivot (472) to also be rotated directly by drive pivot (472). As will be described in greater detail below, pivot arm (480) is configured to pivot about drive pivot (472) to move output gear (490) into communication with primary rotation input (484) or idler gear (456) of actuation drive module (450).

Selector arm (482) extends outwardly from pivot arm (480) and terminates at an outer end opposite of drive pivot (472). Selector arm (482) is generally configured to engage with one or more portions of shifting drive input (474) as will be described in greater detail below to pivot lock arm (476) and pivot arm (480) about drive pivot (472). Thus, selector arm (482) is configured to shift rotation drive module (470) into various drive configurations to control rotation of shaft assembly (114) and/or a portion of the actuation associated with actuation drive module (450).

Shifting drive input (474) is generally configured to be driven by one or more motors to shift rotation drive module (470) into various drive configurations. Shifting drive input (474) includes a band tensioner (486) and a shifting arm (488). Band tensioner (486) is generally configured to rotate via shifting drive input (474) to selectively adjust a tension on drive bands (440, 442). Specifically, band tensioner (486) defines an oval shaped or oblong cross-section. Band tensioner (486) is further disposed in an off-center position relative to the rotation axis of shifting drive input (474). Together, these features permit band tensioner (486) to manipulate drive bands (440, 442), which are threaded around band tensioner (486) upon rotation of band tensioner (486). As will be described in greater detail below, such manipulation may include applying greater tension to one drive band (440, 442) over another drive band (442, 440) by band tensioner (486) moving into a position that engages one drive band (440, 442) over the other drive band (442, 440).

Shifting arm (488) extends outwardly from the rotation axis of shifting drive input (474), protruding from an outer perimeter of shifting drive input (474) and/or band tensioner (486). Shifting arm (488) is generally configured to manipulate selector arm (482) to selectively pivot lock arm (476) and pivot arm (480) using rotation of shifting drive input (474). Shifting arm (488) may be further used to hold lock arm (476) and pivot arm (480) in a predetermined position, as will be described in greater detail below.

An exemplary use of drive system (420) is shown in FIGS. 14A through 14D. As can be seen, drive bands (440, 442) extend from articulation drive module (430) to rotation drive module (470). In use, drive bands (440, 442) may be used to transfer power from first articulation drive input (432), second articulation drive input (434) or both to power rotation of shaft assembly (114) or actuation of end effector (116) with power from first articulation drive input (432), second articulation drive input (434) or both. Such power may be controlled using tension on drive bands (440, 442). For instance, as best seen in FIG. 14A, drive system (420) may be initially operated in a single drive configuration. In this configuration, each drive module (430, 450, 470) may be driven by the particular drive input (432, 434, 452) or drive pivot (472) associated with a given drive module (430, 450, 470). In other words, the particular function (e.g., rotation of shaft assembly (114), actuation of end effector (116), pitch articulation of end effector (116), and yaw articulation of end effector (116)) associated with each drive module (430, 450, 470) may be driven by only a single motor input.

In the single drive configuration, shifting drive input (474) of rotation drive module (470) may be rotated to position band tensioner (486) in an approximately 2 o'clock position as shown in FIG. 14A. It should be understood that clock positions referred to herein are relative to the position of shifting drive input (474) as shown in FIGS. 14A through 14D. Thus, in other contexts, different clock positions may be used. In the 2 o'clock position, the longitudinal axis of band tensioner (486) is generally oriented in a proximal direction with a slight lateral skew. In this position, band tensioner (486) engages drive bands (440, 442) with a relatively low tension. With such a low tension on drive bands (440, 442), friction between drive bands (440, 442) and output gear (490) is sufficiently low such that drive bands (440, 442) may not communicate rotary motion to output gear (490).

Also in the single drive configuration, shifting drive input (474) may be rotated to position shifting arm (488) also in the 2 o'clock position. In this position, a counterclockwise rotational force may be applied to shifting drive input (474) to push selector arm (482) in a clockwise direction. This may cause pivoting of pivot arm (480) also in the clockwise direction to promote engagement between output gear (490) and primary rotation input (484).

With shifting drive input (474) positioned as described above, drive inputs (432, 434, 452) and drive pivot (472) may be used to independently drive their respective functions. Specifically, primary rotation input (484) may be used to rotate shaft assembly (114) via output gear (490) and drive pivot (472). Similarly, actuation drive input (452) may be used to actuate end effector (116) clamp, staple and cut tissue via idler gear (456). First articulation drive input (432) may likewise drive one aspect of articulation (e.g., pitch, yaw, etc.) of end effector (116) by driving one or more articulation capstans (not shown) associated with first articulation drive input (432). Second articulation drive input (434) may drive another aspect of articulation (e.g., pitch, yaw, etc.) of end effector (116) by driving one or more articulation capstans (not shown) associated with second articulation drive input (434).

During use, it may be desirable to drive a given function of surgical instrument (110) with an additional motor for increased mechanical advantage for the given function. For instance, as shown in FIG. 14B, drive system (420) may be transitioned to a first multiple drive configuration. In the first multiple drive configuration, drive system (420) is generally configured to provide additional power to first articulation drive input (432) to effectively double the power used for one aspect of articulation (e.g., pitch, yaw, etc.) of end effector (116).

To transition drive system (420) to the first multiple drive configuration, shifting drive input (474) is rotated to move band tensioner (486) and shifting arm (488) to about a 3 o'clock position. In this position, band tensioner (486) is laterally offset relative to the rotation axis of shifting drive input (474) toward second drive band (442). This laterally offset position permits band tensioner (486) to apply additional tension to first drive band (440), thereby increasing the friction on first drive band (440) and output gear (490). With this added friction, first drive band (440) may be used to communicate power from drive pivot (472) to first articulation drive input (432) via first drive band (440) and output gear (490).

As noted above, shifting arm (488) is also moved to about the 3 o'clock position. As can be seen in FIG. 14B, this move disengages shifting arm (488) from selector arm (482), which permits pivot arm (480) to pivot in a counterclockwise direction moving output gear (490) out of engagement with primary rotation input (484), thereby diverting power from primary rotation input (484) to first articulation drive input (432). Lock arm (476) is similarly pivoted in a counterclockwise direction, which moves lock teeth (478) into engagement with primary rotation input (484). Thus, rotation of shaft assembly (114) may be locked in the first multiple drive configuration via lock teeth (478).

With shifting drive input (474) positioned as described above, some drive inputs (432, 434, 452) may still be used independently to drive their respective functions, while drive pivot (472) may be used to provide supplementary power to articulation drive module (430). Specifically, drive pivot (472) may be used in combination with first articulation drive input (432) to drive one aspect of articulation (e.g., pitch, yaw, etc.) of end effector (116) by driving one or more articulation capstans (not shown) associated with first articulation drive input (432). Meanwhile, actuation drive input (452) may be used to actuate end effector (116) clamp, staple and cut tissue via idler gear (456). Second articulation drive input (434) may likewise drive another aspect of articulation (e.g., pitch, yaw, etc.) of end effector (116) by driving one or more articulation capstans (not shown) associated with second articulation drive input (434).

Figure 14D:
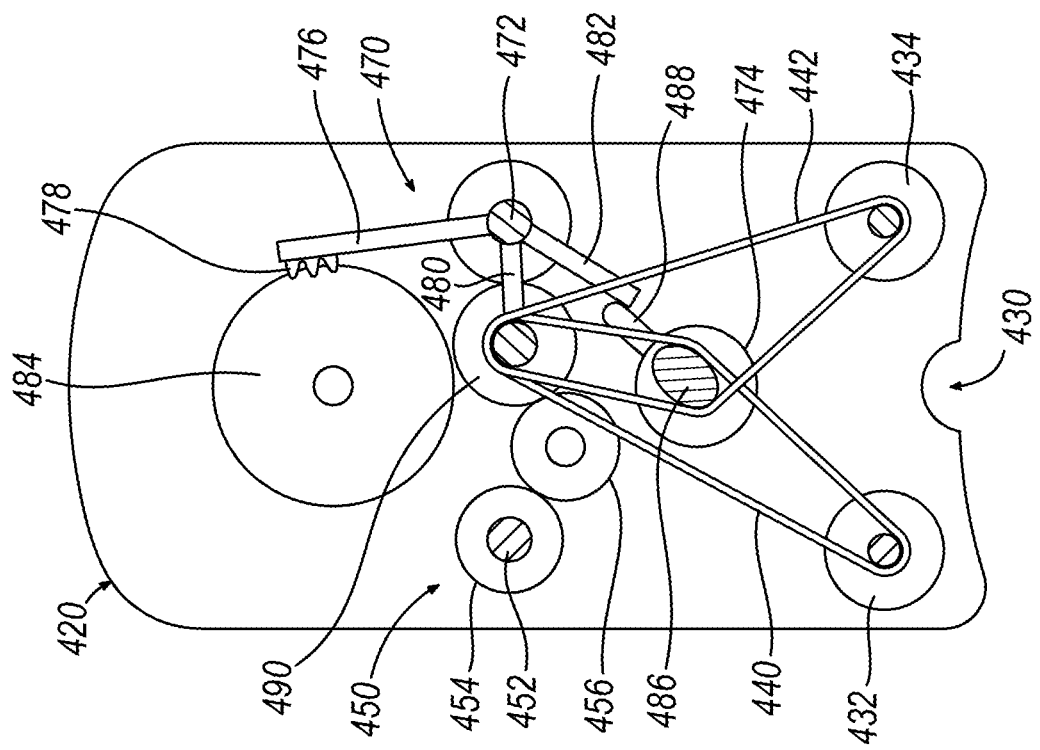
FIG. 14D depicts still another top plan view of the drive system of FIG. 14A, the drive system in a third multiple drive configuration.
Figure 14C:
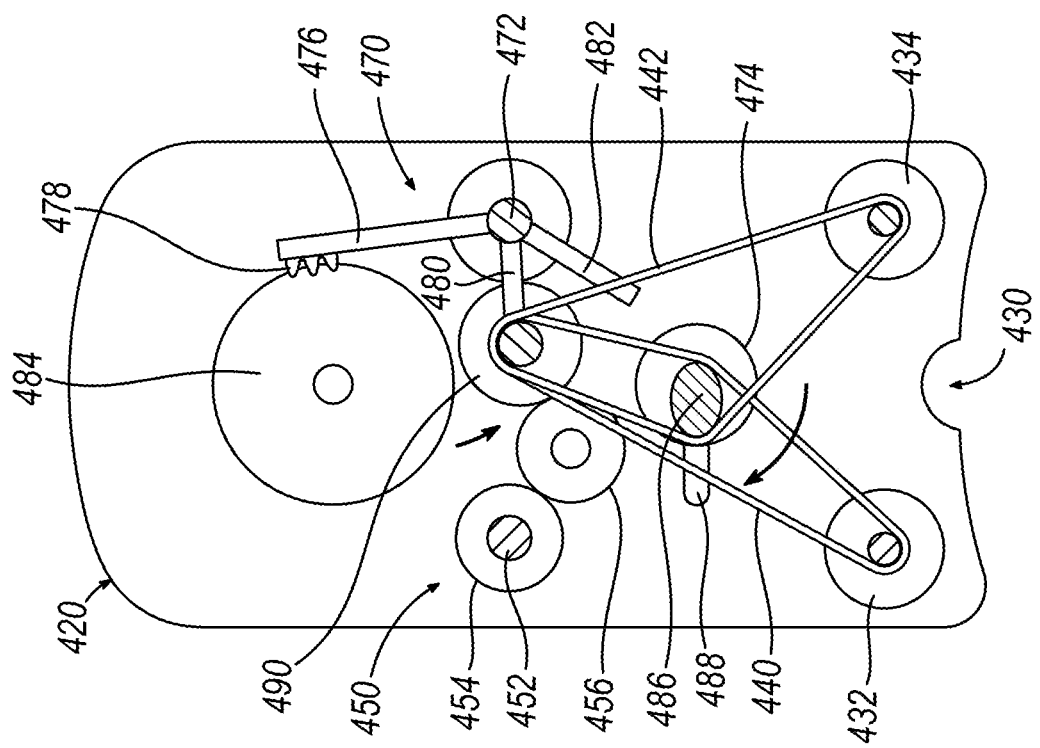
FIG. 14C depicts yet another top plan view of the drive system of FIG. 14A, the drive system in a second multiple drive configuration.

During use, it may be desirable to alternatively drive another given function of surgical instrument (110) with an additional motor for increased mechanical advantage for the given function. For instance, as shown in FIG. 14C, drive system (420) may be transitioned to a second multiple drive configuration. In the second multiple drive configuration, drive system (420) is generally configured to provide additional power to second articulation drive input (434) to effectively double the power used for one aspect of articulation (e.g., pitch, yaw, etc.) of end effector (116).

To transition drive system (420) to the second multiple drive configuration, shifting drive input (474) is rotated to move band tensioner (486) and shifting arm (488) to about a 9 o'clock position. In this position, band tensioner (486) is laterally offset relative to the rotation axis of shifting drive input (474) toward first drive band (440). This laterally offset position permits band tensioner (486) to apply additional tension to second drive band (442), thereby increasing the friction of second drive band (442) and output gear (490). With this added friction, second drive band (442) may be used to communicate power from drive pivot (472) to second articulation drive input (434) via second drive band (442) and output gear (490).

As noted above, shifting arm (488) is also moved to about the 9 o'clock position. As can be seen in FIG. 14C, this move continues the disengagement of shifting arm (488) from selector arm (482), which maintains pivot arm (480) in a position with output gear (490) out of engagement with primary rotation input (484), thereby diverting power from primary rotation input (484) to second articulation drive input (434). Lock arm (476) also maintains a position with lock teeth (478) engaged with primary rotation input (484). Thus, rotation of shaft assembly (114) may be locked in the second multiple drive configuration via lock teeth (478).

With shifting drive input (474) positioned as described above, some drive inputs (432, 434, 452) may still be used independently to drive their respective functions, while drive pivot (472) may be used to provide supplementary power to articulation drive module (430). Specifically, drive pivot (472) may be used in combination with second articulation drive input (434) to drive one aspect of articulation (e.g., pitch, yaw, etc.) of end effector (116) by driving one or more articulation capstans (not shown) associated with second articulation drive input (434). Meanwhile, actuation drive input (452) may be used to actuate end effector (116) to clamp, staple and cut tissue via idler gear (456). First articulation drive input (432) may likewise drive another aspect of articulation (e.g., pitch, yaw, etc.) of end effector (116) by driving one or more articulation capstans (not shown) associated with second articulation drive input (434).

During use, it may be desirable to alternatively drive still another given function of surgical instrument (110) with an additional motor for increased mechanical advantage for the given function. For instance, as shown in FIG. 14D, drive system (420) may be transitioned to a third multiple drive configuration. In the third multiple drive configuration, drive system (420) is generally configured to provide additional power to actuation drive module (450) to effectively double the power used for actuation of end effector (116).

To transition drive system (420) to the third multiple drive configuration, shifting drive input (474) is rotated to move band tensioner (486) and shifting arm (488) to about a 1 o'clock position. In this position, band tensioner (486) is approximately oriented vertically or proximally. This proximal position permits band tensioner (486) to release tension from both first drive band (440) and second drive band (442). With the tension released, first drive band (440) and second drive band (442) may be configured to not transmit power between output gear (490), first articulation drive input (432), and second articulation drive input (434).

As noted above, shifting arm (488) is also moved to about the 1 o'clock position.

As can be seen in FIG. 14D, this move reengages shifting arm (488) with selector arm (482), but from an opposite side of selector arm (482) in comparison to the single drive configuration described above. This engagement may cause shifting arm (488) to pivot selector arm (482) in a counterclockwise direction. As a result, pivot arm (480) may likewise pivot in a counterclockwise direction, which may move output gear (490) into communication with idler gear (456) of actuation drive module (450). Once output gear (490) and idler gear (456) are engaged, drive pivot (472) may rotate idler gear (456) via output gear (490).

With shifting drive input (474) positioned as described above, some drive inputs (432, 434, 452) may still be used independently to drive their respective functions, while drive pivot (472) may be used to provide supplementary power to actuation drive module (450). Specifically, drive pivot (472) may be used in combination with actuation drive input (452) to actuate end effector (116) to clamp, staple and cut tissue via idler gear (456). First articulation drive input (432) may be used to drive one aspect of articulation (e.g., pitch, yaw, etc.) of end effector (116) by driving one or more articulation capstans (not shown) associated with first articulation drive input (432). Meanwhile, second articulation drive input (434) may be used to drive another aspect of articulation (e.g., pitch, yaw, etc.) of end effector (116) by driving one or more articulation capstans (not shown) associated with second articulation drive input (434).

C. Exemplary Alternative Drive System with Movable Gears

FIG. 15A shows an exemplary alternative drive system (520) that may be readily incorporated into surgical instrument described above. Drive system (520) of the present example is similar to drive system (320) described above in that drive system (520) of the present example is generally configured to receive external rotary inputs to drive one or more actuators for actuating end effector (116) to clamp, staple, and cut tissue, for rotating end effector (116) and/or shaft assembly (114), and for articulating end effector (116) relative to a longitudinal axis defined by shaft assembly (114). Drive system (520) may also include a manual actuator (not shown) similar to manual actuator (124) described above, which may be in the form of a knob configured to be manually rotated.

Like drive system (320) described above, drive system (520) of the present example includes one or more drive modules (530, 550, 570) configured to drive various functions of surgical instrument (110). Unlike drive modules (330, 350, 370) described above, which were described as being operable independently of each other, one or more of drive modules (530, 550, 570) of the present example may be configured to communicate with another drive module (530, 550, 570). As will be described in greater detail below, this configuration may be generally desirable to selectively permit multiple motors to drive a single function of surgical instrument (110) and thereby increase the mechanical advantage provided to a given function of surgical instrument (110). In addition, or in the alternative, this configuration may be generally desirable to selectively permit a single motor to drive multiple functions of surgical instrument (110).

Drive system (520) includes an articulation drive module (530), an actuation drive module (550), and a rotation drive module (570). Articulation drive module (530) is similar to articulation drive module (330) described above in that articulation drive module (530) includes a first articulation drive input (532) and a second articulation drive input (534). Although not shown, it should be understood that drive inputs (532, 534) may likewise each include a respective articulation capstan (not shown) similar to articulation capstans (336, 338) described above. Like articulation capstans (336, 338), such articulation capstans in the present example may be configured to selectively tension one or more respective articulation cables similar to articulation cables (340, 342, 344, 346) described above to ultimately control movement of end effector (116) relative to a longitudinal axis defined by shaft assembly (114).

Unlike articulation drive module (330) described above, articulation drive module (530) of the present example includes an articulation shift arm (536) configured to control the function of first articulation drive input (532). Specifically, articulation shift arm (536) extends outwardly from a central axis of first articulation drive input (532) and terminates at an engagement portion (538). An articulation idler gear (540) is disposed on articulation shift arm (536) between first articulation drive input (532) and engagement portion (538). Articulation shift arm (536) is generally configured to move articulation idler gear (540) relative to first articulation drive input (532). As will be described in greater detail below, actuation shift arm (536) is configured to pivot about first articulation drive input (532) to selectively control communication rotary motion from first articulation drive input (532) to other components of articulation drive module (530) via articulation idler gear (540).

Articulation shift arm (536) is associated with an articulation lock arm (542) and a tensioning lock arm (544). Articulation shift arm (536), articulation lock arm (542) and tensioning lock arm (544) are coupled to each other at the central axis of first articulation drive input (532). Thus, articulation shift arm (536), articulation lock arm (542) and tensioning lock arm (544) are generally configured to pivot together.

Articulation lock arm (542) and tensioning lock arm (544) each include a plurality of teeth. As will be described in greater detail below, articulation lock arm (542) and tensioning lock arm (544) are each configured to mesh or otherwise engage with other components of articulation drive module (530) via the plurality of teeth to lock certain functions of surgical instrument (110).

Articulation drive module (530) further includes an articulation gear (546) and a tensioning gear (548) associated with first articulation drive input (532). Articulation gear (546) is generally configured to mesh with articulation idler gear (540) to selectively receive rotary motion from first articulation drive input (532). Although not shown, it should be understood that such rotary motion of articulatio gear (546) may be used to drive one or more structures of articulation drive module (530) to control an aspect of articulation of end effector (116) relative to shaft assembly (114). For instance, in some examples a capstan (not shown) similar to capstans (336, 338) described above may be in communication with articulation gear (546) rather than being directly in communication with first articulatio drive input (532). Such a capstan may be configured to selectively tension and/or release one or more articulation cables (not shown) similar to articulation cables (340, 342, 344, 346) described above, which may be used to control an aspect of articulation of end effector (116) (e.g., pitch, yaw, etc.).

Tensioning gear (548) is generally configured to mesh with articulation idler gear (540) to selectively receive rotary motion from first articulation drive input (532). Although not shown, it should be understood that such rotary motion of tensioning gear (548) may be used to drive one or more structures of articulation drive module (530). For instance, in some examples, tensioning gear (548) may be configured to communicate with gears, sheaves, belts, cams, and/or etc. to apply tension to one or more articulation cables (not shown) similar to articulation cables (340, 342, 344, 346). Such a tensioning feature may be desirable during use of surgical instrument (110) to add rigidity to shaft assembly (114) at the point of articulatio for end effector (116).

Actuation drive module (550) of the present example is similar to actuation drive module (350) described above in that actuation drive module (550) includes an actuation drive input (552) configured to engage a drive output of robotic arm (42) to control actuation of end effector (116) and other components associated with end effector (116) to clamp, staple and cut tissue. To promote such functionality, actuation drive input (552) includes gear teeth such that actuation drive input (552) is configured to mesh with an idler gear (556). Although not shown, it should be understood that idler gear (556) may mesh or otherwise communicate with one or more structures similar to bevel gear (358), capstan gear (360), actuation capstan (362). As similarly described above, such structures may permit actuation drive input (452) to rotate an actuation capstan (not shown) to selectively tension/release one or more actuation drive cables (not shown) similar to actuation drive cables (364, 366) described above. The actuation drive cables may then communicate with structures associated with end effector (116) to clamp, staple and cut tissue.

Unlike actuation drive module (350) described above, actuation drive module (550) of the present example is generally configured to selectively communicate with rotation drive module (570). As will be described in greater detail below, this feature may be desirable to permit actuation drive module (550) of the present example to selectively actuate end effector (116) with increased mechanical advantage. In some examples, this may be facilitated by, for example, communicating power from rotation drive module (570) to actuation drive module (550) via idler gear (556).

Rotation drive module (570) of the present example is similar to rotation drive module (370) described above in that rotation drive module (570) is configured to drive rotation of shaft assembly (114) of surgical instrument (110) and other components associated therewith. However, unlike rotation drive module (370) described above, rotation drive module (570) of the present example is configured to selectively communicate rotary power from rotation drive module (570) to actuation drive module (550).

Rotation drive module (570) of the present example omits structures similar to primary rotation drive input (372) and secondary rotation drive input (374). Instead, rotation drive module (570) includes a rotation drive input (572) and a shifting drive input (574). Rotation drive input (572) is positioned similarly to primary rotation drive input (372) described above. However, instead of being configured to receive rotary input for rotation of shaft assembly (114), rotation drive input (562) is configured to be manipulated by other structures of rotation drive module (570) to drive either rotation of shaft assembly (114) or other functions of surgical instrument (110).

Rotation drive input (572) is coupled to a lock arm (576), a pivot arm (580) and a selector arm (582). Rotation drive input (572) is generally configured to permit pivoting of lock arm (576), pivot arm (580) and selector arm (582) about an axis defined by drive pivot (572). Although rotation drive input (572) itself is not configured to directly provide movement of lock arm (576), pivot arm (580) and selector arm (582), it should be understood that in some examples, rotation drive input (572) may be configured to manipulate such movement by providing a ratcheting action and/or biasing lock arm (576), pivot arm (580) and selector arm (582) toward one or more predetermined positions.

Rotation drive input (572) is further configured as a drive input to communicate rotary motion from one or more motors in robotic arm (42) to other components of rotation drive module (570). This, the structure of rotation drive input (572) may be configured as a gear or other feature configured to mesh or communicate rotary motion from rotation drive input (572) to other portions of rotation drive module (570) or actuation drive module (550). As will be described in greater detail below, such communication may be used to drive rotation of shaft assembly (114) via rotation drive input (572) or to provide additional power to actuation drive module (550).

Lock arm (576), pivot arm (580), selector arm (582) extend outwardly from rotation drive input (572). Additionally, lock arm (576), pivot arm (580) and selector arm (582) each extend at a fixed angle relative to each other. In other words, lock arm (576), pivot arm (580), and selector arm (582) are configured to pivot about rotation drive input (572) while maintaining a fixed position relative to each other. Lock arm (576) includes a plurality of lock teeth (578) disposed on an outer end of lock arm (576) opposite of rotation drive input (572). As will be described in greater detail below, lock teeth (578) are configured to engage primary rotation input (584) to selectively lock rotation of shaft assembly (114).

Pivot arm (580) is disposed between lock arm (576) and selector arm (582). Pivot arm includes an output gear (590) disposed on an outer end of pivot arm (580) opposite of rotation drive input (572). Output gear (590) is rotatably coupled to pivot arm (580) and is configured to mesh with either primary rotation input (584) or idler gear (556) of actuation drive module (550) to communicate rotary motion from rotation drive input (572) to either primary rotation input (584) or idler gear (556). As will be described in greater detail below, pivot arm (580) is configured to pivot about rotation drive input (572) to move output gear (590) into communication with primary rotation input (584) or idler gear (556) of actuation drive module (550).

Selector arm (582) extends outwardly from pivot arm (580) and terminates at an outer end opposite of rotation drive input (572). Selector arm (582) is generally configured to engage with one or more portions of shifting drive input (574) to pivot lock arm (576) and pivot arm (580) about rotation drive input (572). Thus, selector arm (582) is configured to shift rotation drive module (570) into various drive configurations to control rotation of shaft assembly (114) and/or a portion of the actuation associated with actuation drive module (550).

Shifting drive input (574) is generally configured to be driven by one or more motors to shift rotation drive module (570) into various drive configurations. Shifting drive input (574) includes a pair of rotation shifting members (586) and a pair of articulation shifting members (588). Rotation shifting members (586) are generally configured to rotate via shifting drive input (574) to selectively adjust the position of lock arm (576) and pivot arm (580) via selector arm (582). Similarly, articulation shifting members (588) are generally configured to rotate via shifting drive input (574) to selectively adjust the position of articulation shift arm (536), articulation lock arm (542) and tensioning lock arm (544) of articulation drive module (530).

An exemplary use of drive system (520) is shown in FIGS. 15A through 16B. During use, drive system (520) is generally configured to shift functionality of surgical instrument (110) by adjusting the configuration of articulation drive module (530), actuation drive module (550), and/or rotation drive module (570) using rotation of shifting drive input (574). For instance, drive system (520) may initially be operated in a first drive configuration shown in FIG. 15A.

In the first drive configuration, drive system (520) may operate similarly to drive system (320) described above with each drive module (530, 550, 570) being configured to drive a respective function of surgical instrument (110). Specifically, articulation drive module (530) may be configured to drive aspects of articulation of end effector (116) relative to a longitudinal axis defined by shaft assembly (114), actuation drive module (550) may be configured to drive actuation of end effector (116) to clamp, staple and cut tissue, and rotation drive module (570) may be configured to drive rotation of shaft assembly (114).

As best seen in FIG. 15A, articulation drive module (530) is configured in the first drive configuration to use drive inputs (532, 534) for articulation of end effector (116). In this configuration, first articulation drive input (532) is configured to drive one aspect of articulation (e.g., pitch, yaw, etc.). Specifically, articulation shift arm (536) is positioned relative to first actuation drive input (532) such that articulation idler gear (540) meshes with first actuation drive input (532) and articulation gear (546). First actuation drive input (532) may thus drive one aspect of articulation by communicating rotary motion to articulation gear (546), which may be coupled to a capstan (not shown). As described above, the capstan configured to tension and/or release articulation cables similar to articulation cables (340, 342) described above to drive articulation of end effector (116). Meanwhile, second articulation drive input (534) may drive another aspect of articulation by directly or indirectly rotating another capstan (not shown) similarly configured to tension and/or release articulation cables.

Actuation drive module (550) is configured in the first drive configuration to use actuation drive input (552) to drive actuation of end effector (116) to clamp, staple, and cut tissue. In this configuration, actuation drive module (550) may operate similarly to actuation drive module (350) described above. For instance, actuation drive input (552) may communicate rotary motion to idler gear (556). Idler gear (556) may then in turn drive rotation of one or more bevel gears (not shown), one or more capstan gears (not shown), and/or other structures associated with actuation drive module (550) to ultimately rotate an actuation capstan (not shown). As similarly described above, such a capstan may be used to tension and/or release actuation cables, similar to actuation cables (364, 366), which may be used to actuate end effector (116).

Rotation drive module (570) is configured in the first drive configuration to use rotation drive input (552) to drive rotation of shaft assembly (114). In this configuration, rotation drive module (570) may operate similarly to rotation drive module (370) described above. For instance, rotation drive input (572) may communicate rotary motion to primary rotation input (584) via output gear (590). Primary rotation input (584) may then rotate shaft assembly (114) using rotary motion from rotation drive input (572).

During use it may be desirable to change the operation of drive system (520) to change one or more functions of surgical instrument (110). For instance, in some examples it may be desirable to increase the mechanical advantage of one or more functions of surgical instrument. In addition, or in the alternative, it may be desirable to divert power from one function for use with another function. To this end, FIGS. 15B through 16B show drive system (520) in a second drive configuration. In the second drive configuration, drive system (520) is generally configured to divert power from rotation drive module (570) to actuation drive module (550). Additionally, drive system (520) is also generally configured to divert power within articulation drive module (530) from one function to another.

As best seen in FIG. 15B, transitioning of drive system (520) in the present example from the first drive configuration to the second drive configuration is accomplished by rotating shifting drive input (574) of rotation drive module (570). During rotation of shifting drive input (574), rotation shifting members (586) and articulation shifting members (588) move with shifting drive input (574) to move and/or pivot selector arm (582) of rotation drive module (570) and articulation shift arm (536) of articulation drive module (530), respectively.

Movement of selector arm (582) drives corresponding movement of pivot arm (580) and lock arm (576). Movement of pivot arm (580) moves output gear (590) away from primary rotation input (584) to mesh with or otherwise engage idler gear (556) of actuation drive module (550). Meanwhile, movement of lock arm (576) moves lock teeth (578) of lock arm (576) into engagement with primary rotation input (584) to lock rotation of shaft assembly (114). In this configuration, rotation drive input (572) may communicate rotary motion to actuation drive module (550) via idler gear (556) to approximately double the power used for actuation of end effector (116).

Articulation shift arm (536) moves in an opposite direction relative to selector arm (582) to shift articulation drive module (530). Specifically, movement of articulation shift arm (536) drives corresponding movement articulation idler gear (540), which is coupled to articulation shift arm (536). This movement disengages articulation idler gear (540) from articulation gear (546) and engages articulation idler gear (540) with tensioning gear (548). In this configuration, first articulation drive input (532) may communicate rotary motion to tensioning gear (548) via articulation idler gear (540). Such motion of tensioning gear (548) may then be used to tension one or more articulation cables associated with articulation drive module (530). By way of example only, such tensioning may be used in some examples to increase the rigidity of end effector (116) where articulation occurs, limiting pitch and/or yaw articulation of end effector (116). Such a feature may be desirable in some examples to eliminate backlash from articulation of end effector (116) and/or to use end effector (116) for manipulation of tissue or other anatomical structures.

Movement of articulation shift arm (536) simultaneously drives corresponding movement of articulation lock arm (542) and tensioning lock arm (544). Specifically, in the first drive configuration, tensioning lock arm (544) engages tensioning gear (548) to prevent rotation of or otherwise lock tensioning gear (548). Similarly, in the second drive configuration, articulation lock arm (542) engages articulation gear (546) to prevent rotation of, or otherwise lock articulation gear (546).

D. Exemplary Shifting Mechanism

Figure 17A:
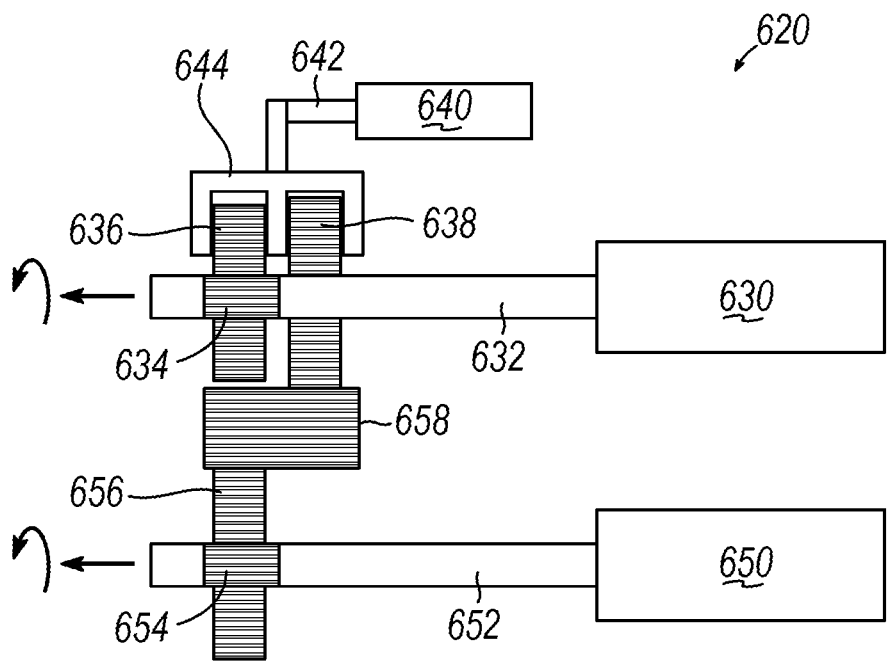
FIG. 17A depicts a side elevational view of an exemplary shifting mechanism that may be used with the surgical instrument of FIG. 4, the shifting mechanism in a single drive configuration.

FIG. 17A shows an exemplary shifting mechanism (620) that may be readily incorporated into any of drive systems (320, 420, 520) described above. Shifting mechanism (620) is generally configured to selectively transfer power from one input to input to increase the mechanical advantage provided to a selected power output. Thus, shifting mechanism (620) may be incorporated into drive systems (320, 420, 520) described above for use with one or more drive inputs (332, 334, 352, 372, 374, 432, 434, 452, 472, 532, 534, 552, 572) to selectively increase the mechanical advantage for a given function of surgical instrument (110).

Shifting mechanism (620) includes a first power source (630) and a second power source (650). Power sources (630, 650) in the present example may correspond to one or more of drive inputs (332, 334, 352, 372, 374, 432, 434, 452, 472, 532, 534, 552, 572) described above when shifting mechanism (620) is incorporated into a given drive system (320, 420, 520). Alternatively, in other applications, power sources (630, 650) may correspond to separate independent motors configured to provide a rotary output.

First power source (630) and second power source (650) include a first output shaft (632) and a second output shaft (652), respectively. As will be described in greater detail below, output shafts (632, 652) are generally configured to communicate power to one or more operational functions. For instance, in examples where shifting mechanism (620) is incorporated into drive systems (320, 420, 520), each output shaft (632, 652) may be configured to communicate power to a given function of surgical instrument (110). Regardless, output shafts (632, 652) are generally configured to communicate power independently of each other in some configurations to power separate operational functions. Meanwhile, in other configurations, output shafts (632, 652) are generally configured to combine power for a single operational function.

First output shaft (632) includes a splined portion (634) disposed proximate an end of output shaft (632) opposite first power source (630). Splined portion (634) includes a plurality of teeth or other features configured to transmit rotary motion to other portions of shifting mechanism (620). Specifically, shifting mechanism (620) includes a first drive gear (636) and a transfer gear (638) associated with first output shaft (632). Splined portion (634) is generally configured to engage a corresponding interior of either first drive gear (636) or transfer gear (638) depending on the relative position of first drive gear (636) and transfer gear (638). As will be described in greater detail below, first output shaft (632) is generally configured to rotate first drive gear (636) or transfer gear (638) via splined portion (634) depending on the position of first drive gear (636) and transfer gear (638) relative to splined portion (634).

Shifting mechanism (620) further includes an actuator (640) associated with first drive gear (636) and transfer gear (638). Actuator (640) is generally configured to selectively move first drive gear (636) and transfer gear (638) relative to splined portion (634) to control communication of rotary motion from first output shaft (632) to either first drive gear (636) or transfer gear (638). Although actuator (640) is shown schematically in the present example, it should be understood that actuator (640) may take on a variety of forms. By way of example only, suitable forms for actuator (640) may include solenoids, pneumatic or hydraulic rams, lead screw mechanisms, and/or etc.

Actuator (640) includes a drive rod (642) extend from a side of actuator (640). Drive rod (642) is coupled to a gear housing (644), which is configured to hold first drive gear (636) and transfer gear (638) while permitting rotation of first drive gear (636) and transfer gear (638) within gear housing (644). As will be described in greater detail below, actuator (640) is configured to translate gear housing (644) via drive rod (642) to move gears (636, 638) relative to splined portion (634) of first output shaft (632) to control rotation of gears (636, 638) via first output shaft (632).

Second output shaft (652) also includes a splined portion (654) disposed proximate an end of second output shaft (652) opposite second power source (650). Splined portion (654) includes a plurality of teeth or other features configured to transmit rotary motion to other portions of shifting mechanism (620). Specifically, shifting mechanism (620) includes a second drive gear (656) and an intermediate gear (658) associated with second output shaft (652). Splined portion (654) is generally configured to engage a corresponding interior of second drive gear (656). Thus, second output shaft (652) is generally configured to rotate second drive gear (656) via splined portion (634).

Intermediate gear (658) is configured as an elongate spur gear. In this configuration, intermediate gear (658) is configured to mesh with second drive gear (656) and transfer gear (638). As will be described in greater detail below, transfer gear (638) may idle in some configurations without having any impact on rotation of intermediate gear (658), second drive gear (656) and/or second output shaft (652). Yet in other configurations, transfer gear (638) may mesh with splined portion (634) of first output shaft (632) to transfer power from first output shaft (632) to second drive gear (656) via intermediate gear (658).

Figure 17B:
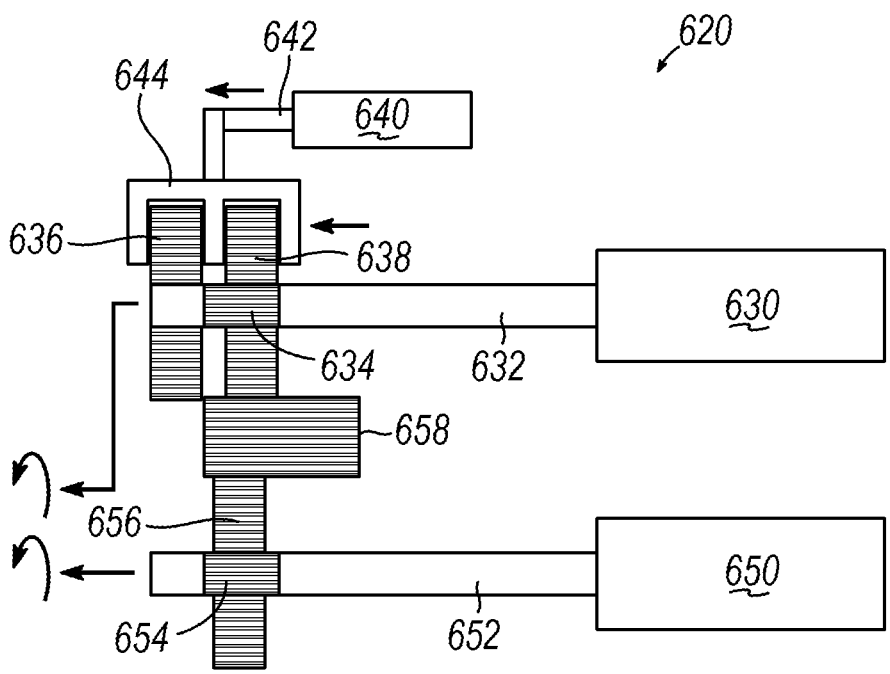
FIG. 17B depicts another side elevational view of the shifting mechanism of FIG. 17A, the shifting mechanism in a multi-drive configuration.

FIGS. 17A and 17B show an exemplary use of shifting mechanism (620). In use, shifting mechanism (620) is configured to shift from a single drive configuration for driving a different operational function with first power source (630) and second power source (650) to a multi-drive configuration for driving a single operational function using both first power source (630) and second power source (650). In use with drive systems (320, 420, 520) described above, this may include, for example, driving rotation of shaft assembly (114) and actuation of end effector (116) with shifting mechanism (620) in the single drive configuration and then driving only rotation of shaft assembly (114) or actuation of end effector (116) with increased mechanical advantage in the multi-drive configuration. It should be understood that this is merely one example and that shifting mechanism (620) may be used with other combinations of functions of surgical instrument (110) including rotation of shaft assembly (114), actuation of end effector (116), and/or various aspects of articulation of end effector (116).

As best seen in FIG. 17A, shifting mechanism (620) may initially be in the single drive configuration. As noted above, this configuration corresponds to shifting mechanism (620) providing two rotary outputs with one powered by first power source (630) and the other provided by second power source (650). In this configuration, actuator (640) retracts drive rod (642) to align first drive gear (636) with splined portion (634) of first output shaft (632). As a result, first output shaft (632) may rotate first drive gear (636) via splined portion (634). Although not shown, it should be understood that first drive gear (636) may mesh with other gears associated with a given operational function. For instance, when shifting mechanism (620) is used with drive systems (320, 420, 520), first drive gear (636) may mesh with any suitable gear associated with drive systems (320, 420, 520) to ultimately drive a given function of surgical instrument (110).

Also in the single drive configuration, second drive gear (656) is engaged with splined portion 9654) of second output shaft (652). As a result, second output shaft (652) may rotate second drive gear (656) via splined portion (654). Although not shown, it should be understood that second drive gear (656) may likewise mesh with other gears associated with a given operational function. For instance, when shifting mechanism (620) is used with drive systems (320, 420, 520), second drive gear (656) may mesh with any suitable gear associated with drive systems (320, 420, 520) to ultimately drive a given function of surgical instrument (110).

During rotation of second drive gear (656), intermediate gear (658) may rotate and idle transfer gear (638). For instance, while first drive gear (636) is engaged with splined portion (634), transfer gear (638) is disengaged from splined portion (634). Thus, transfer gear (638) may be configured to freely rotate about first output shaft (632) when shifting mechanism (620) is in the single drive configuration. First drive gear (636) is not configured to mesh with intermediate gear (658), so rotation of first output shaft (632) is generally independent of second output shaft (652) when shifting mechanism (620) is in the single drive configuration.

As best seen in FIG. 17B, shifting mechanism (620) may be transitioned to the multi-drive configuration from the single drive configuration via actuator (640). Specifically, actuator (640) may advance drive rod (642) to translate first drive gear (636) and transfer gear (638) relative to first output shaft (632). Translation of first drive gear (636) disengages first drive gear (636) from splined portion (634). Meanwhile, translation of transfer gear (638) engages transfer gear (638) with splined portion (634). First output shaft (632) may then rotate transfer gear (638) rather than first drive gear (636).

With rotation of transfer gear (638), power from first power source (630) is transferred from first output shaft (632) to second drive gear (656) via transfer gear (638) and intermediate gear (658). This configuration may increase the power provided by second drive gear (656). In some examples, this may effectively double the power provided by second drive gear (656). Meanwhile, first drive gear (636) is disengaged from splined portion (634), so any operational functions associated with first drive gear (636) may be unpowered when shifting mechanism (620) is in the multi-drive configuration.

E. Exemplary Selectable Multi-Drive Mechanism

Figure 18A:
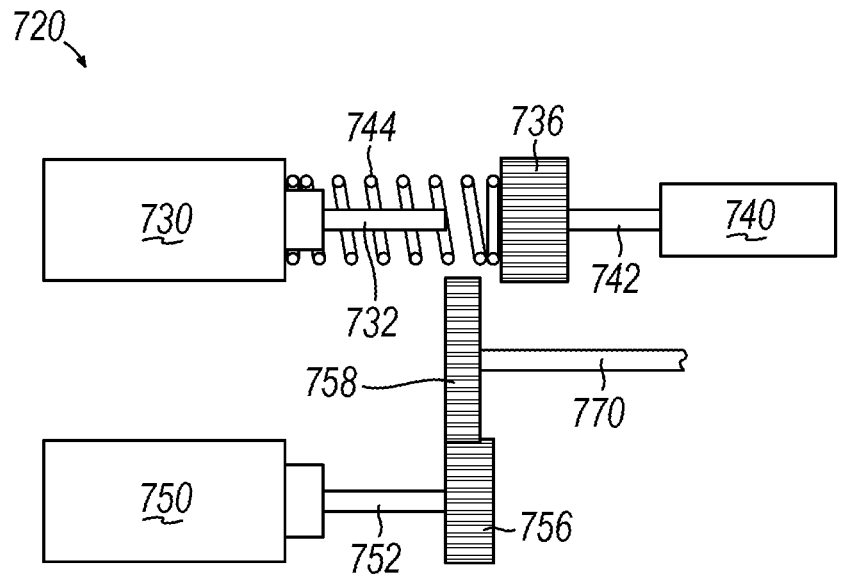
FIG. 18A depicts a side elevational view of an exemplary alternative shifting mechanism that may be used with the surgical instrument of FIG. 4, the shifting mechanism in a single drive configuration.

FIG. 18A shows an exemplary multi-drive mechanism (720) that may be readily incorporated into any of drive systems (320, 420, 520) described above. Multi-drive mechanism (720) is generally configured to selectively increase the output power of multi-drive mechanism (720) by using one or two power sources (730, 750) simultaneously to drive a single output. Thus, multi-drive mechanism (720) may be incorporated into drive systems (320, 420, 520) described above for use with one or more drive inputs (332, 334, 352, 372, 374, 432, 434, 452, 472, 532, 534, 552, 572) to selectively increase the mechanical advantage for a given function of surgical instrument (110).

Multi-drive mechanism (720) includes a first power source (730) and a second power source (750). Power sources (730, 750) in the present example may correspond to one or more of drive inputs (332, 334, 352, 372, 374, 432, 434, 452, 472, 532, 534, 552, 572) described above when multi-drive mechanism (720) is incorporated into a given drive system (320, 420, 520). Alternatively, in other applications, power sources (730, 750) may correspond to separate independent motors configured to provide a rotary output.

First power source (730) and second power source (750) include a first output shaft (732) and a second output shaft (752), respectively. As will be described in greater detail below, output shafts (732, 752) are generally configured to communicate power to a predetermined operational function associated with multi-drive mechanism (720). For instance, in examples where multi-drive mechanism (720) is incorporated into drive systems (320, 420, 520), one or both output shaft (732, 752) may be configured to communicate power to a given function of surgical instrument (110).

First power source (730) is configured to selectively couple to a first drive gear (736) via first output shaft (732). In particular, a resilient member (744) extends between first power source (730) and first drive gear (736). Resilient member (744) is generally configured to resiliently bias first drive gear (736) toward a decoupled configuration, while also permitting selective coupling of first drive gear (736) to first output shaft (732). In the present example, resilient member (744) includes a coil spring, but may include resilient bands, torsion springs, leaf springs, and/or etc.

On an opposite side of first drive gear (736), first drive gear (736) is coupled to an actuator (740) by a drive rod (742) extending between actuator (740) and first drive gear (736). Actuator (740) is generally configured to move first drive gear (736) against the resilient bias of resilient member (744) via drive rod (742) to couple first drive gear (736) to first output shaft (732). Although actuator (740) is shown schematically in the present example, it should be understood that actuator (740) may take on a variety of forms. For instance, in some examples actuator (740) may include a rotary drive element, a solenoid, a pneumatic or hydraulic piston/ram, a lead screw mechanism, and/or etc.

Second power source (750) is coupled to a second drive gear (756) via second output shaft (752). Second drive gear (756) is configured to mesh with an intermediate gear (758), which includes a drive output (770) extending from an intermediate gear (758). Although not shown, it should be understood that drive output (770) may be coupled to a predetermined operational function. Thus, second power source (750) may be configured to power a predetermined operational function via second drive gar (756) and intermediate gear (758).

Figure 18B:
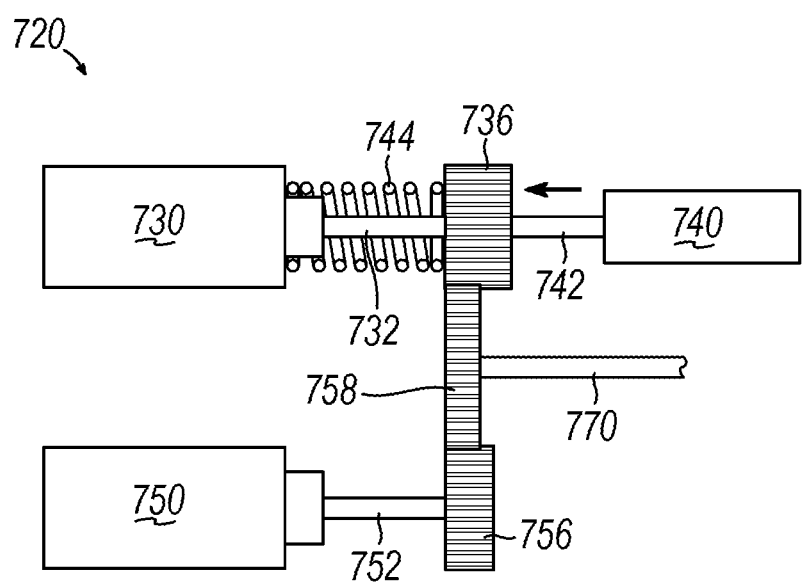
FIG. 18B depicts another side elevational view of the shifting mechanism of FIG. 18A, the shifting mechanism in a multi-drive configuration.

FIGS. 18A and 18B show an exemplary use of multi-drive mechanism (720). In use, multi-drive mechanism (720) may shift from a single drive configuration to a multi-drive configuration to drive a predetermined operational function with second power source (750) alone or in combination with first power source (730). For instance, in configurations with multi-drive mechanism (720) incorporated into drive systems (320, 420, 520), multi-drive mechanism (720) may be used to power a function of surgical instrument (110) using only second power source (750) when multi-drive mechanism (720) is in the single drive configuration. The same function of surgical instrument (110) may then be driven with both first power source (730) and second power source (750) when multi-drive mechanism (720) is in the multi-drive configuration for increased mechanical advantage of the same function.

As best seen in FIG. 18A, the single drive configuration includes first drive gear (736) disengaged from first output shaft (732) via resilient feature (744). As a result, first power source (730) is unable to communicate rotary power to first drive gear (736). Moreover, resilient feature, also referred to as resilient member (744) pushes first drive gear (736) out of alignment with intermediate gear (758) such that first drive gear (736) is unable to communicate rotary power to drive output (770) via intermediate gear (758).

Also in the single drive configuration, second drive gear (756) may be meshed with intermediate gear (758). Rotary power may thus be communicated from second power source (750) to intermediate gear (758) and drive output (770) via second output shaft (752) and second drive gear (756). Thus, in the single drive configuration, only second power source (750) is configured to provide drive to drive output (770).

As best seen in FIG. 18B, multi-drive mechanism (720) may be transitioned from the single drive configuration to the multi-drive configuration using actuator (740). Specifically, actuator (740) may advance drive rod (742), which may also advance first drive gear (736) into engagement with first output shaft (732). Once first drive gear (736) is engaged with first output shaft (732), first power source (730) may communicate rotary power to first drive gear (736) via first output shaft (732).

Advancement of first drive gear (736) also moves first drive gear (736) into alignment with intermediate gear (758). Upon alignment, first drive gear (736) and intermediate gear (758) are configured to mesh. Thus, first power source (730) is configured to communicate power to intermediate gear (758) and drive output (770) via first output shaft (732) and first drive gear (736).

Second power source (750), second output shaft (752) and second drive gear (756), meanwhile, remain in the same configuration described above with respect to the single drive configuration. Thus, in the multi-drive configuration, both first power source (730) and second power source (750) are configured to communicate power to drive output (770) via intermediate gear (758). As a result, the power output of drive output (770) may increase by the sum of the power from first power source (730) and the power from second power source (750). In some examples, this may approximately double the mechanical advantage provided by drive output (770).

III. Exemplary Shifting Mechanisms for Adjustable Mechanical Advantage

As noted above, in some examples surgical instrument (110) may be used with certain drive systems and or mechanisms similar to drive systems (320, 420, 520) described above. In some examples, suitable drive mechanisms may include drive inputs configured to communicate power from robotic arm (42) to surgical instrument (110) to drive various functions of surgical instrument (110) such as rotation of shaft assembly (114), articulation of end effector (116), and/or actuation of end effector (116). In some examples, it may be desirable to modify the mechanical advantage provided to a given function during a procedure to enhance operational utility of surgical instrument (110). By way of example only, such examples may include certain shifting mechanisms configured to adjust the mechanical advantage of a given drive. While a variety of suitable shifting mechanisms are described below as including such features in specific configurations, it should be understood that in other examples such features may be combined in different configurations without departing from the various concepts described herein.

A. Exemplary Shifting Mechanism with Continuously Variable Belt Drive

Figure 19:
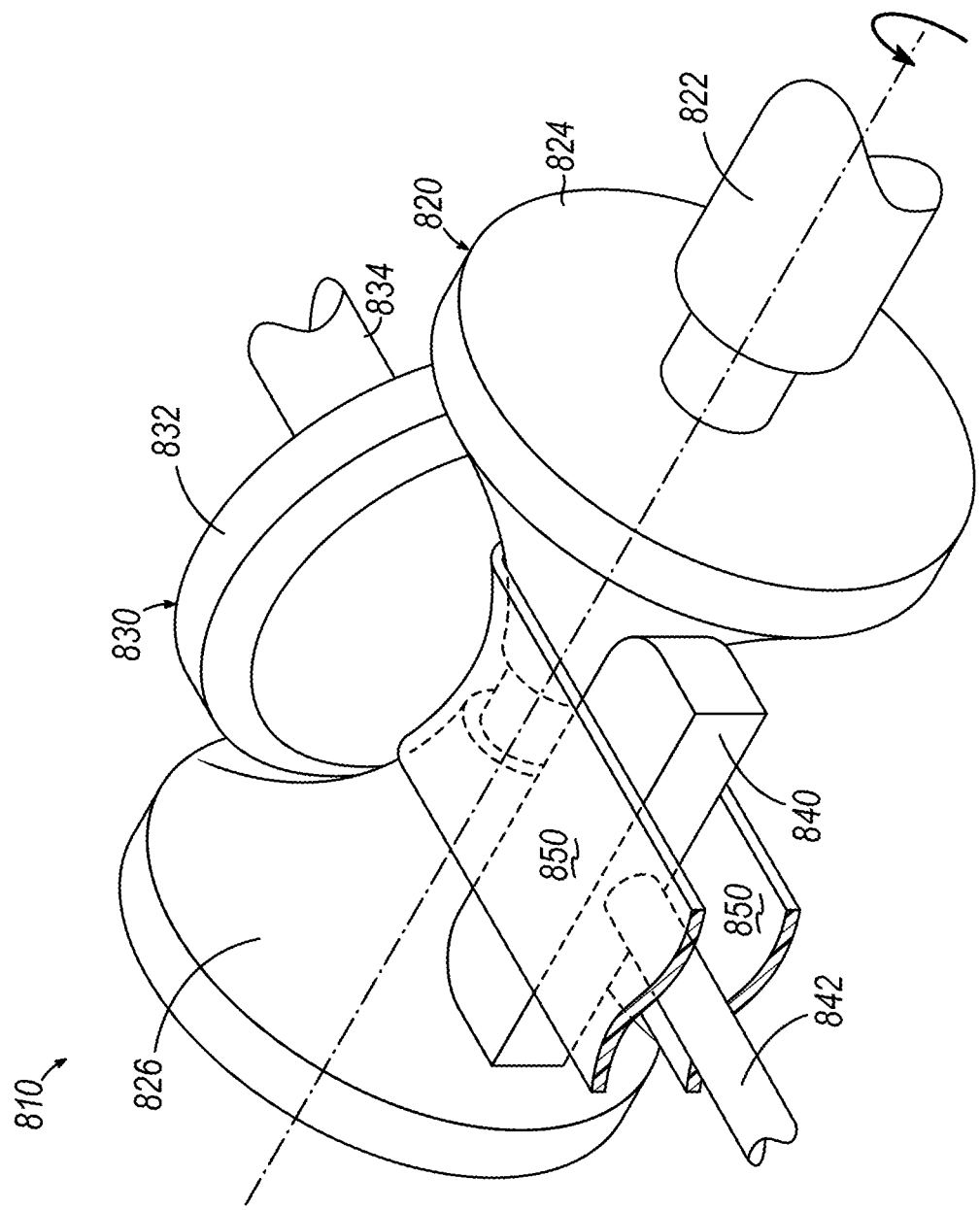
FIG. 19 depicts a perspective view of another exemplary alternative shifting mechanism that may be used with the surgical instrument of FIG. 4.

FIG. 19 shows an exemplary shifting mechanism (810) that may be readily incorporated into any one or more of drive systems (320, 420, 520) described above. Shifting mechanism (810) is generally configured to provide continuously variable adjustment of a rotary drive. For instance, in the case of incorporation with drive system (320), shifting mechanism (810) may be associated with any one or more of drive inputs (332, 334, 352, 372, 374) to adjust the rotary motion of a given drive input (332, 334, 352, 372, 374) to have a selected mechanical advantage, which may be used to ultimately drive a given function associated with the given drive input (332, 334, 352, 372, 374).

Figure 20:
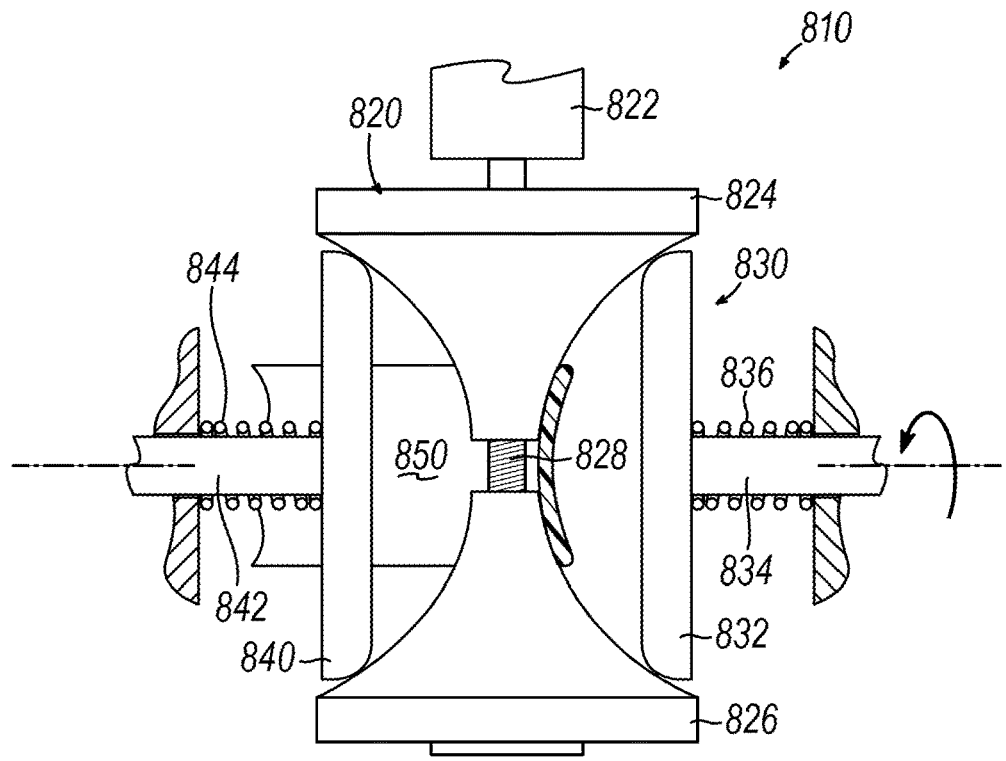
FIG. 20 depicts a top plan view of the shifting mechanism of FIG. 19, the shifting mechanism in a first configuration.

As best seen in FIGS. 19 and 20, shifting mechanism (810) includes a rotary drive assembly (820), an adjustment assembly (830) and a belt (850). Rotary drive assembly (820) includes an input shaft (822), a first rotary drive element (824) and a second rotary drive element (826). Input shaft (822) is coupled to first rotary drive element (824) and/or second rotary drive element (826) such that input shaft (822) is configured to rotate both first rotary drive element (824) and second rotary drive element (826). Although not shown, it should be understood that input shaft (822) may extend through first rotary drive element (824) to second rotary drive element (826) to communicate rotation of input shaft (822) to second rotary drive element (826).

Furthermore, input shaft (822) may include one or more keys, splines, or other features configured to communicate rotary motion from input shaft (822) to first rotary drive element (824) and second rotary drive element (826).

First rotary drive element (824) and second rotary drive element (826) each define a generally conical shape. Optionally, in some examples, the conical shape of first rotary drive element (824) and second rotary drive element (826) may include a curvature such as the one shown in FIGS. 19 and 20. First rotary drive element (824) is generally facing second rotary drive element (826) such that the smaller diameter associated with each of first rotary drive element (824) and second rotary drive element (826) are proximate each other. Thus, first rotary drive element (824) and second rotary drive element (826) together may define a generally V-shaped or U-shaped cross-section.

Rotary drive assembly (820) further includes a resilient feature (828) disposed between first rotary drive element (824) and second rotary drive element (826). Resilient feature (828) is generally configured to bias first rotary drive element (824) and second rotary drive element (826) toward each other. In the present example, resilient feature (828) includes a coil spring. In other examples, resilient feature (828) may include various alternative configurations such as resilient bands, leaf springs, disc springs, and/or etc.

Adjustment assembly (830) is disposed between first rotary drive element (824) and second rotary drive element (826). Adjustment assembly (830) is generally configured to engage first rotary drive element (824) and second rotary drive element (826) to selectively adjust the distance between first rotary drive element (824) and second rotary drive element (826). As will be described in greater detail below, this feature may be used to selectively adjust a mechanical advantage associated with shifting mechanism (810).

Adjustment assembly (830) includes a first plunger (832) and a second plunger (840). First plunger (832) and second plunger (840) may be disposed on opposing sides of first rotary drive element (824) and second rotary drive element (826). Together, first plunger (832) and second plunger (840) may be configured to engage first rotary drive element (824) and second rotary drive element (826) to apply a compressive force to first rotary drive element (824) and second rotary drive element (826), which may force first rotary drive element (824) and second rotary drive element (826) away from each other.

First plunger (832) and second plunger (840) each include a respective adjustment shaft (834, 842) and a respective biasing feature (836, 844). Each adjustment shaft (834, 842) is configured to control the relative position of a respective first plunger (832) or second plunger (840) relative to first rotary drive element (824) and second rotary drive element (826). Meanwhile each biasing feature (836, 844) is configured to provide a resilient bias forcing a respective first plunger (832) or second plunger (840) toward first rotary drive element (824) and second rotary drive element (826). Each biasing feature (836, 844) is optional and may be omitted in some examples. However, in examples having biasing features (836, 844), such features may be desirable to simply manipulation of each adjustment shaft (834, 842). For instance, in the present example, the relative position of each adjustment shaft (834, 842) may be set using only a pulling force due to the presence of biasing features (836, 844) rather than a combination of pulling and pushing forces.

Belt (850) is looped around each of first rotary drive element (824) and second rotary drive element (826). Belt (850) is generally configured to frictionally engage first rotary drive element (824) and second rotary drive element (826) to transfer rotatory motion of first rotary drive element (824) and second rotary drive element (826) to belt (850). Although not shown, it should be understood that an opposite loop of belt (850) may be in communication with a wheel, gear, shaft, or other features. Such features may be used to communicate movement of belt (850) to other components for ultimate use in driving one or more functions of surgical instrument (110).

Figure 21:
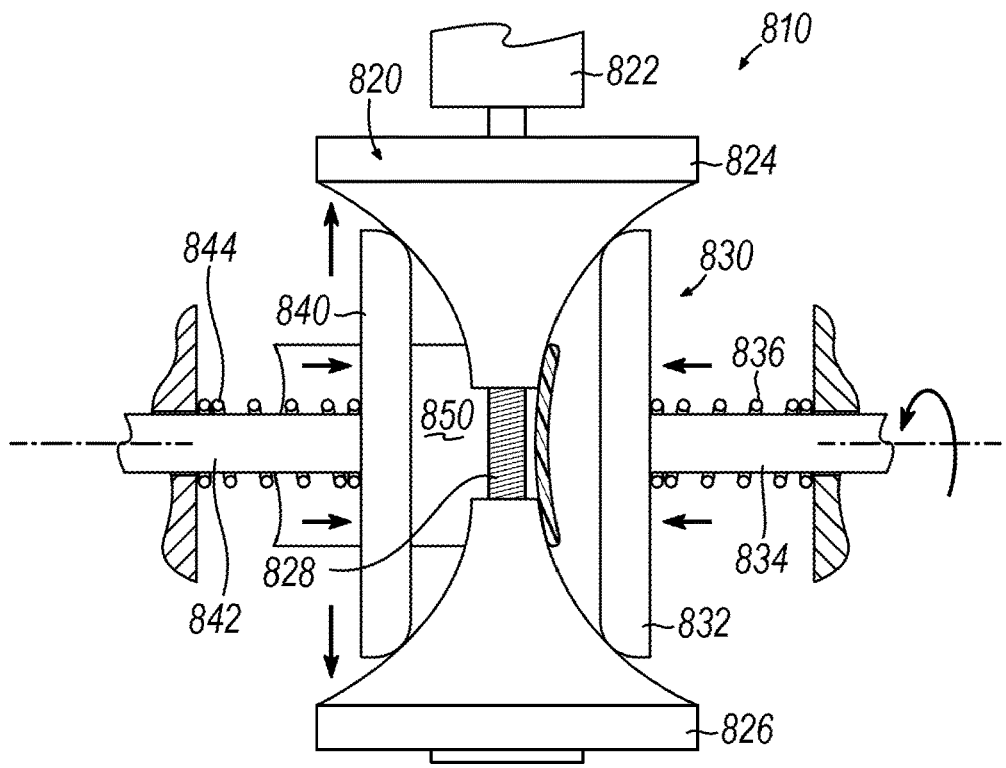
FIG. 21 depicts another top plan view of the shifting mechanism of FIG. 19, the shifting mechanism in a second configuration.

FIGS. 20 and 21 show an exemplary use of shifting mechanism (810). In use, shifting mechanism (810) generally functions as a continuously variable transmission to provide an output via belt (850) having various mechanical advantages. The particular mechanical advantage of the output of belt (850) is generally established by the position of first plunger (832) and second plunger (840) relative to first rotary drive element (824) and second rotary drive element (826).

As can be seen in FIG. 20, first plunger (832) and second plunger (840) may initially be positioned relative to first rotary drive element (824) and second rotary drive element (826) proximate an outer diameter defined by first rotary drive element (824) and second rotary drive element (826). First plunger (832) and second plunger (840) may be positioned as shown by pulling each respective adjustment shaft (834, 842) against the resilient bias of each respective biasing feature (836, 844) to move first plunger (832, 840) away from first rotary drive element (824) and second rotary drive element (826).

With first plunger (832) and second plunger (840) positioned proximate the outer diameter defined by first rotary drive element (824) and second rotary drive element (826), first rotary drive element (824) and second rotary drive element (826) may be driven towards each other via resilient feature (828). As a result, first rotary drive element (824) and second rotary drive element (826) may be separated by a relatively small distance. Belt (850), which may have a fixed width, may thus engage first rotary drive element (824) and second rotary drive element (826) at a relatively large diameter portion of each of first rotary drive element (824) and second rotary drive element (826). Belt (850) may thus be driven by first rotary drive element (824) and second rotary drive element (826) using input shaft (822) with a relatively high mechanical advantage. In other words, belt (850) may have a greater force output when shifting mechanism (810) is in the configuration shown in FIG. 20.

To adjust the mechanical advantage associated with belt (850), first plunger (832) and second plunger (840) may be moved to adjust their position relative to first rotary drive element (824) and second rotary drive element (826). As can be seen in FIG. 21, movement of first plunger (832) and second plunger (840) toward first rotary drive element (824) and second rotary drive element (826) may force first rotary drive element (824) and second rotary drive element (826) away from each other against the resilient bias of resilient feature. As noted above, belt (850) may have a fixed width such that separation of first rotary drive element (824) and second rotary drive element (826) may result in belt (850) engaging first rotary drive element (824) and second rotary drive element (826) at a smaller diameter portion relative to the engagement shown in FIG. 20. Belt (850) may thus be driven by first rotary drive element (824) and second rotary drive element (826) using input shaft (822) with a relatively low mechanical advantage. In other words, belt (850) may have a lower force output when shifting mechanism (810) is in the configuration shown in FIG. 21.

Although the present use shows first plunger (832) and second plunger (840) in only two positions relative to first rotary drive element (824) and second rotary drive element (826), it should be understood that in other uses a plurality of other relative positions may be used. Specifically, first plunger (832) and second plunger (840) may be used at a variety of positions relative to first rotary drive element (824) and second rotary drive element (826). Varying positions may be desirable to provide fine adjustment of the particular mechanical advantage associated with belt (850).

Figure 22:
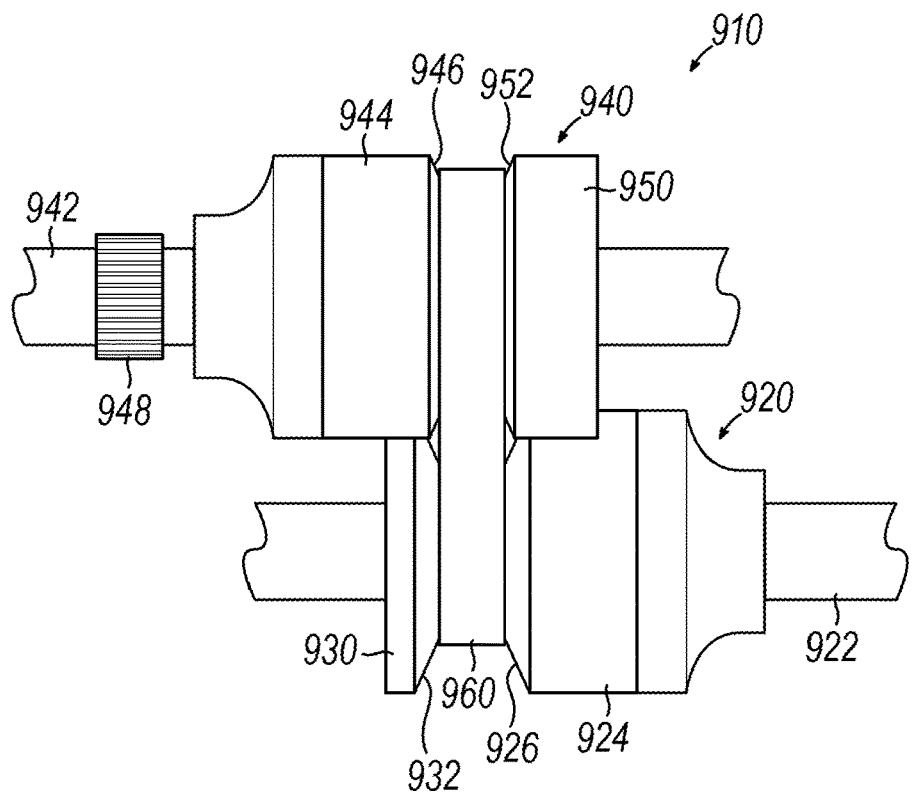
FIG. 22 depicts a side elevational view of yet another exemplary alternative shifting mechanism that may be used with the surgical instrument of FIG. 4.

B. Exemplary Alternative Shifting Mechanism with Continuously Variable Belt Drive FIG. 22 shows an exemplary alternative shifting mechanism (910) similar to shifting mechanism (810) described above. For instance, as with shifting mechanism (810) described above, shifting mechanism (910) of the present example may be readily incorporated into any one or more of drive systems (320, 420, 520) described above. Shifting mechanism (910) is similarly generally configured to provide continuously variable adjustment of a rotary drive. For instance, in the case of incorporation with drive system (320), shifting mechanism (910) may be associated with any one or more of drive inputs (332, 334, 352, 372, 374) to adjust the rotary motion of a given drive input (332, 334, 352, 372, 374) to have a selected mechanical advantage, which may be used to ultimately drive a given function associated with the given drive input (332, 334, 352, 372, 374).

Shifting mechanism (910) includes an input assembly (920), an output assembly (940) and a belt (960) extending between input assembly (920) and output assembly (940). Input assembly (920) includes an input shaft (922), an input sheave (924) and a retainer (930). Input shaft (922) is generally configured to receive rotary input from, for example, any suitable rotary input used drive systems (320, 420, 520) described above to rotate input sheave (924) and retainer (930) to drive movement of belt (960).

Input sheave (924) and retainer (930) are coupled to input shaft (922) such that input sheave (924) and retainer (930) may rotate with input shaft (922). Input sheave (924) and retainer (930) each include a respective angled portion (926, 932) configured to engage belt (960). Specifically, input sheave (924) and retainer (930) are disposed on input shaft (922) with each angled portion (926, 932) facing the other angled portion (932, 926). In this configuration, angled portions (926, 932) together form a V-shaped or U-shaped profile angled outwardly from the axis of input shaft (922). This profile formed by angled portions (926, 932) is generally configured to receive belt (960).

One or more portions of input sheave (924) may be generally configured to move angled portion (926) along the longitudinal axis of input shaft (922) while still permitting input sheave (924) to rotate with input shaft (922). Such movement of angled portion (926) may be relative to angled portion (932) of retainer (930). In other words, retainer (930) is generally configured to remain in a fixed position relative to the longitudinal axis of input shaft (922).

It should be understood that a variety of structures may be used for movement of angled portion (926). For instance, in some examples, movement of angled portion (926) may be driven by oil or other fluids injected into input sheave (934) for telescopic expansion of input sheave (924). In other examples, motor drives, magnetic drives, lead screws, and/ or solenoids may be used to drive movement of angled portion (926) of input sheave (924).

Output assembly (940) includes an output shaft (942), an output sheave (944) and a retainer (950). Output shaft (942) is generally configured to communicate rotary motion transferred via belt (960) from input assembly (920) to other portions of surgical instrument (110) to ultimately drive one or more functions of surgical instrument (110). In the present example, output shaft (942) includes an output gear (948), which may be configured to mesh with other components of surgical instrument (110) such as various gears described above in connection with drive systems (320, 420, 520).

Output sheave (944) and retainer (950) are coupled to output shaft (942) such that output sheave (944) and retainer (950) may rotate with output shaft (942). Output sheave (944) and retainer (950) each include a respective angled portion (946, 952) configured to engage belt (960). Specifically, output sheave (944) and retainer (950) are disposed on output shaft (942) with each angled portion (946, 952) facing the other angled portion (952, 946). In this configuration, angled portions (946, 952) together form a V-shaped or U-shaped profile angled outwardly from the axis of output shaft (942). This profile formed by angled portions (946, 952) is generally configured to receive belt (960).

One or more portions of output sheave (944) may be generally configured to move angled portion (946) along the longitudinal axis of output shaft (942) while still permitting output sheave (944) to rotate with output shaft (942). Such movement of angled portion (946) may be relative to angled portion (952) of retainer (950). In other words, retainer (950) is generally configured to remain in a fixed position relative to the longitudinal axis of output shaft (942).

It should be understood that a variety of structures may be used for movement of angled portion (946). For instance, in some examples, movement of angled portion (946) may be driven by oil or other fluid injected into output sheave (944) for telescopic expansion of output sheave (944). In other examples, motor drives, magnetic drives, lead screws, and/ or solenoids may be used to drive movement of angled portion (946) of output sheave (944).

Figure 23:
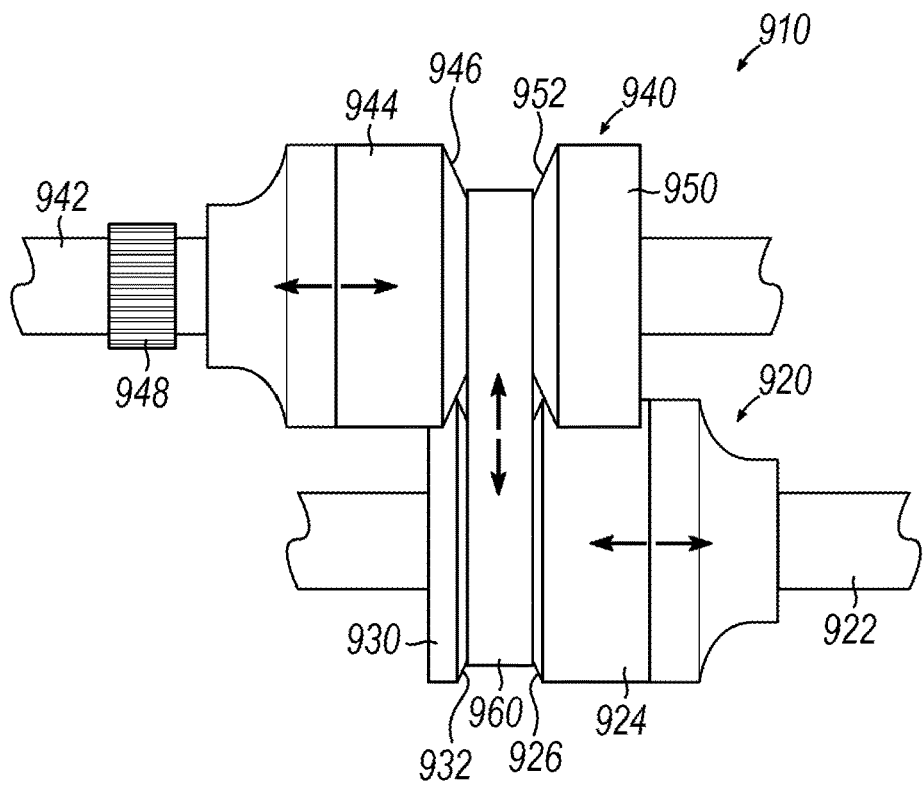
FIG. 23 depicts another side elevational view of the shifting mechanism of FIG. 22, the shifting mechanism being used as a continuously variable transmission.

FIGS. 22 and 23 show an exemplary use of shifting mechanism (910). In use, shifting mechanism (910) generally functions as a continuously variable transmission to provide an output via output gear (948) having various mechanical advantages. The particular mechanical advantage of the output gear (948) is generally established by the position of angled portion (926) of input sheave (924) relative to angled portion (932) of retainer (930) and the position of angled portion (946) of output sheave (944) relative to angled portion (952) of retainer (950).

As can be seen, both angled portion (926) of input sheave (924) and angled portion (946) of output sheave (944) are movable relative to each respective retainer (930, 950). Such movement may change the profile defined between input sheave (924) and retainer (930), and between output sheave (944) and retainer (950). This change in profile, may change engagement of belt (960) with either input sheave (924) and retainer (930), or output sheave (944) and retainer (950). For instance, movement of angled portion (926) of input sheave (924) closer to retainer (930) may result in a narrowing of the profile defined between input sheave (924) and retainer (930). As a result, belt (960) may engage input sheave (924) and retainer (930) at an increasing diameter portion of input sheave (924) and retainer (930). Similarly, movement of angled portion (946) of output sheave (944) closer to retainer (950) may result in a narrowing of the profile defined between output sheave (944) and retainer (950). As a result, belt (960) may engage output sheave (944) and retainer (950) at an increasing diameter portion of output sheave (944) and retainer (950).

Both input sheave (924) and output sheave (944) may be adjusted as described above during use to engage belt (960) at different diameter positions relative to input sheave (924) and/or output sheave (944). As a result, shifting mechanism (910) may be used to provide a variety of drive ratios for belt (960) between input assembly (920) and output assembly (940). This may be desirable in use with surgical instrument (110) to drive one or more functions of surgical instrument (110) with different drive characteristics. For instance, during some procedures, shifting mechanism (910) may be set to provide a relatively high mechanical advantage or relatively high force output at output gear (948) for applications requiring greater actuation forces. In other procedures, shifting mechanism (910) may be set to provide a relatively low mechanical advantage or relatively low force output at output gear (948) for applications requiring less force and greater speed.

C. Exemplary Alternative Shifting Mechanism with Movable Arm

Figure 24:
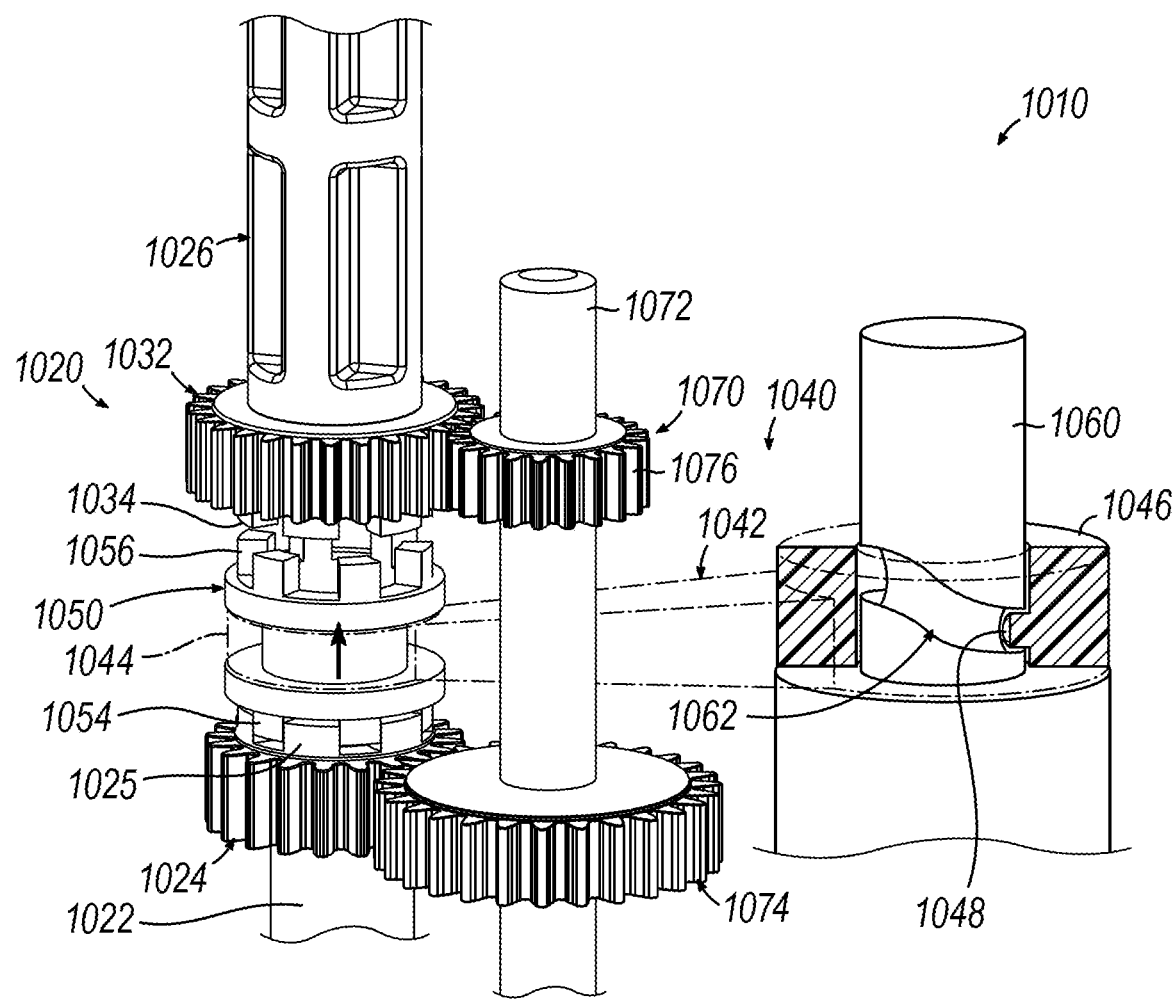
FIG. 24 depicts a perspective view of still another exemplary alternative shifting mechanism that may be used with the surgical instrument of FIG. 4.
Figure 25:
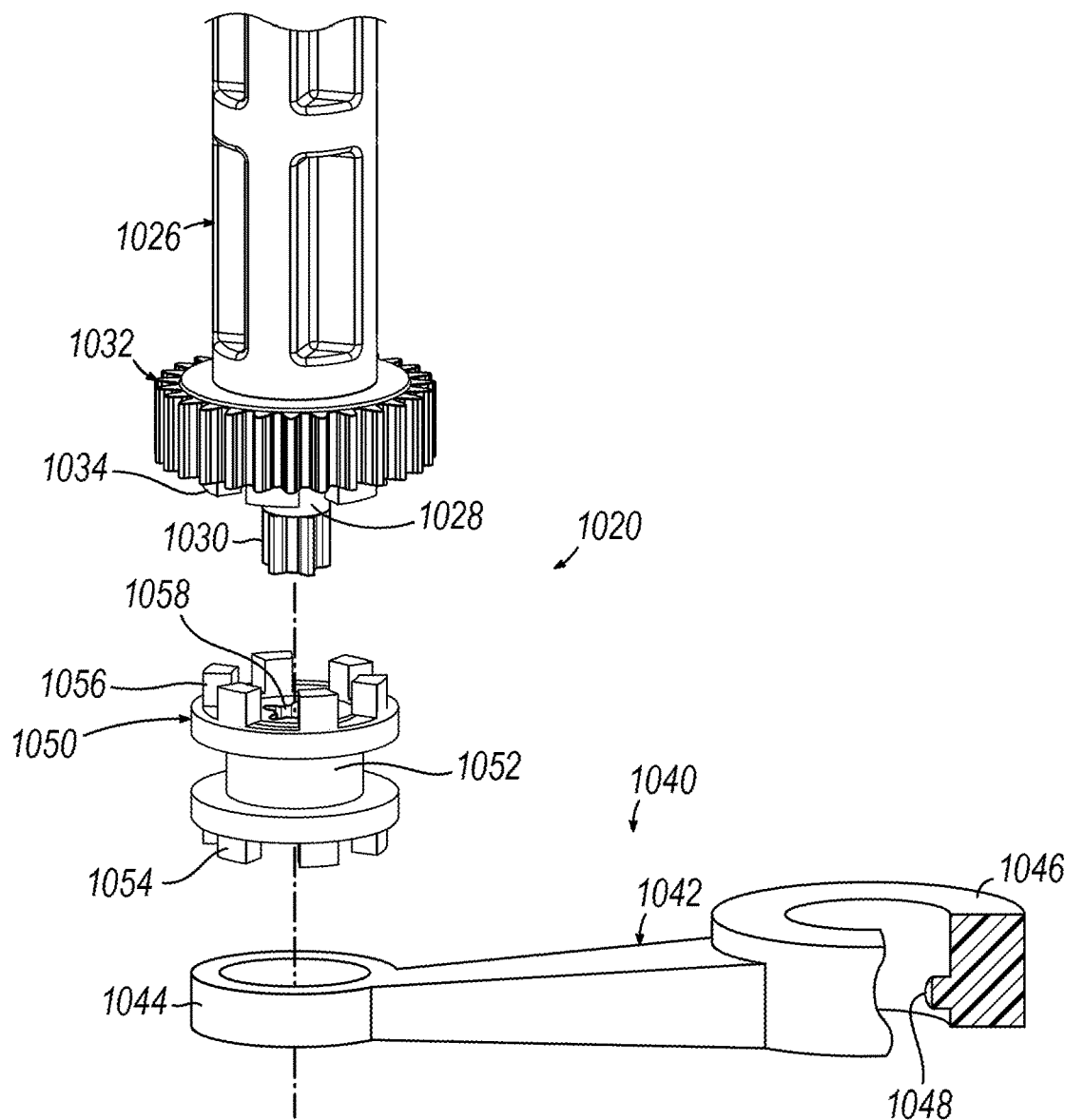
FIG. 25 depicts an exploded perspective view of a portion of the shifting mechanism of FIG. 24.
Figure 26:
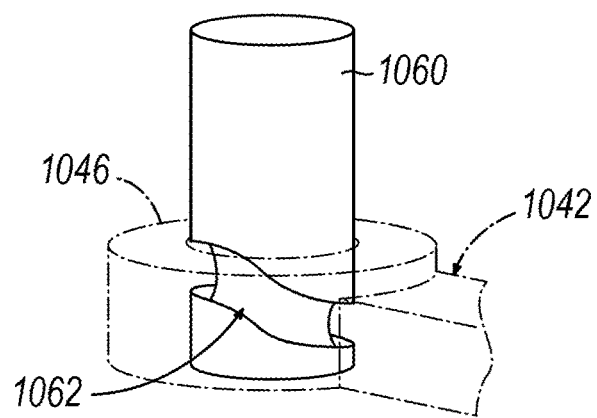
FIG. 26 depicts a detailed perspective view of a shift shaft of the shifting mechanism of FIG. 24.

FIGS. 24 through 26 show an exemplary alternative shifting mechanism (1010) that may be readily incorporated into any one or more of drive systems (320, 420, 520) described above in addition to, or in lieu of, shifting mechanisms (810, 910) described above. For instance, in the case of incorporation with drive system (320), shifting mechanism (1010) may be associated with any one or more of drive inputs (332, 334, 352, 372, 374) to adjust the rotary motion of a given drive input (332, 334, 352, 372, 374) to have a selected mechanical advantage, which may be used to ultimately drive a given function associated with the given drive input (332, 334, 352, 372, 374).

Shifting mechanism (1010) includes a drive assembly (1020), a shift assembly (1040), and a reduction assembly (1070). Shifting mechanism (1010) is generally configured to use shift assembly (1040) to selectively shift between a direct drive configuration via drive assembly (1020) to a reduction drive configuration via reduction assembly (1070). As will be described in greater detail below, the direct drive configuration may be desirable for operation with relatively high speed at a relatively low torque. Meanwhile, the reduction drive configuration may be desirable for operation with relatively low speed at a relatively high torque. In one merely exemplary configuration, shifting mechanism (1010) may be incorporated into drive system (320) for use with actuation drive module (350) to selectively shift between high speed, low torque operation of end effector (116) to low speed, high torque operation of end effector (116).

Drive assembly (1020) includes an input shaft (1022) and an output shaft (1026). Input shaft (1022) is generally configured to couple with one or more motors to provide rotary power to shifting mechanism (1010). In merely one exemplary implementation, input shaft (1022) may be coupled to articulation drive input (352) of actuation drive module (350), or any other suitable drive input. Regardless, input shaft (1022) includes an input gear (1024) coupled thereto and configured to rotate with input shaft (1022). Input gear (1024) includes an engagement portion (1025) oriented towards output shaft (1026). As will be described in greater detail below, engagement portion (1025) is generally configured to engage a portion of shift assembly (1040) to transmit rotary motion from input gear (1024) to output shaft (1026) in some configurations.

Output shaft (1026) is coaxial with input shaft (1022). Although not shown, it should be understood that a portion of output shaft (1026) may be configured to communicate with other components of surgical instrument (110) to drive one or more operational functions thereof. For instance, in an implementation with actuation drive module (350), output shaft (1026) may couple to actuation drive gear (354) or other components associated therewith to drive actuation of end effector (116).

Output shaft (1026) defines a smooth portion (1028) and a keyed portion (1030). Smooth portion (1028) is configured to receive an idler gear (1032) such that idler gear (1032) may be independently rotatable relative to output shaft (1026). Keyed portion (1030) defines a spline, key, key channel or other rotational lock feature. As will be described in greater detail below, keyed portion (1030) is generally configured to engage a portion of shift assembly (1040) to transmit rotary motion from a portion of shift assembly (1040) to output shaft (1026).

Idler gear (1032) includes an engagement portion (1034) extending downwardly from a portion of idler gear (1032) toward input shaft (1022). As will be described in greater detail below, engagement portion (1034) is generally configured to engage a portion of shift assembly (1040) to transmit rotary motion from idler gear (1032) to output shaft (1026) via shift assembly (1040) in some configurations.

As best seen in FIGS. 25 and 26, shift assembly (1040) includes a shift arm (1042), a clutch (1050), and a shift shaft (1060). Shift arm (1042) includes a clutch receiver (1044) and a shift receiver (1046) on opposing ends of shift arm (1042). Clutch receiver (1044) defines a hollow cylindrical member configured to receive clutch (1050). Similarly, shift receiver (1046) defines a hollow cylindrical member configured to receive shift shaft (1060). Furthermore, the interior of shift receiver (1046) includes a cam protrusion (1048) extending into the hollow interior of shift receiver (1046). As will be described in greater detail below, cam protrusion (1048) is generally configured to engage a portion of shift shaft (1060) to drive movement of shift arm (1042) along shift shaft (1060).

Clutch (1050) includes an arm receiver (1052), a lower engagement portion (1054), an upper engagement portion (1056), and a keyed bore (1058). Arm receiver (1052) is configured to be received within clutch receiver (1044) of shift arm (1042). Thus, arm receiver (1052) defines a channel indentation within clutch (1050). This configuration of arm receiver (1052) defines a flange structure on opposing sides of clutch (1050) to hold clutch receiver (1044) of shift arm (1042) within arm receiver (1052). As will be described in greater detail below, this configuration of arm receiver (1052) and clutch receiver (1044) is configured to permit shift arm (1042) to drive movement of clutch (1050) relative to input shaft (1022) and output shaft (1026).

Lower engagement portion (1054) and upper engagement portion (1056) are both configured to engage portions of drive assembly (1020) to rotatably fix clutch (1050) relative to a given portion of drive assembly (1020). Specifically, lower engagement portion (1054) and upper engagement portion (1056) each include blocks, teeth or other engagement features configured to mate with certain counterpart components. As will be described in greater detail below, clutch (1050) may be moved by shift arm (1042) to drive engagement between either lower engagement portion (1054) or upper engagement portion (1056) with a corresponding engagement portion (1025, 1034) of drive assembly (1020).

Keyed bore (1058) extends through the center of clutch (1050). Specifically, keyed bore (1058) is configured to receive a portion of output shaft (1026) such that at least a portion of output shaft (1026) may extend through clutch (1050). Keyed bore (1058) is generally configured to engage keyed portion (1030) of output shaft (1026). As such, it should be understood that keyed bore (1058) may include features corresponding to keyed portion (1030) such as keys, keyways, spline channels, splines, and/or etch. Such engagement may be configured such that clutch (1050) may be rotationally locked relative to output shaft (1026). Thus, clutch (1050) may be configured to drive rotation of output shaft (1026). Meanwhile, clutch (1050) may also be configured to laterally slide relative to output shaft (1026). As will be described in greater detail below, this lateral sliding may be desirable to permit movement of clutch (1050) via shift arm (1042).

As best seen in FIG. 26, shift shaft (1060) is configured to be received within shift receiver (1046) of shift arm (1042). Shift shaft (1060) defines a cam profile (1062) indented into a portion of shift shaft (1060). The particular shape of cam profile (1062) is one that defines a low portion and a high portion with a sloped portion between the low portion and the high portion. As will be described in greater detail below, cam profile (1062) is generally configured to receive cam protrusion (1048) of shift arm (1042) to drive shift arm (1042) axially up or down along the length of shift arm (1042) by rotating shift shaft (1060). In other words, shift shaft (1060) is generally configured to convert rotation thereof into axial translation of shift arm (1042) via cam profile (1062).

Rotation of shift shaft (1060) may be controlled by a variety of mechanisms. For instance, in examples where shifting mechanism (1010) is incorporated into drive system (320), shift shaft (1060) may be coupled to secondary rotation drive input (374) to facilitate rotation of shift shaft (1060). In other examples, shift shaft (1060) may be coupled to any other suitable drive input to receive rotary motion from one or more motors associated with robotic arm (42). In still other examples, shift shaft (1060) may be coupled to a separate actuator for manual rotation via a rotation knob, lever, crank, push button, and/or etc.

Reduction assembly (1070) includes a reduction shaft (1072), a large reduction gear (1074) and a small reduction gear (1076). Large reduction gear (1074) and small reduction gear (1076) are both coupled to reduction shaft (1072) such that reduction shaft (1072), large reduction gear (1074), and small reduction gear (1076) are all configured to rotate together.

Large reduction gear (1074) is configured to mesh with input gear (1024). Meanwhile, small reduction gear (1076) is configured to mesh with idler gear (1032). As will be described in greater detail below, large reduction gear (1074) is configured to be rotated by input gear (1024), which may rotate small reduction gear (1076) via reduction shaft (1072) to ultimately rotate idler gear (1032). As will also be described in greater detail below, idler gear (1032) may idle in some configurations, but drive output shaft (1026) rotation in other configurations. Thus, reduction assembly (1070) may generally continuously rotate during use, but such rotation may be unused in some configurations.

Figure 27A:
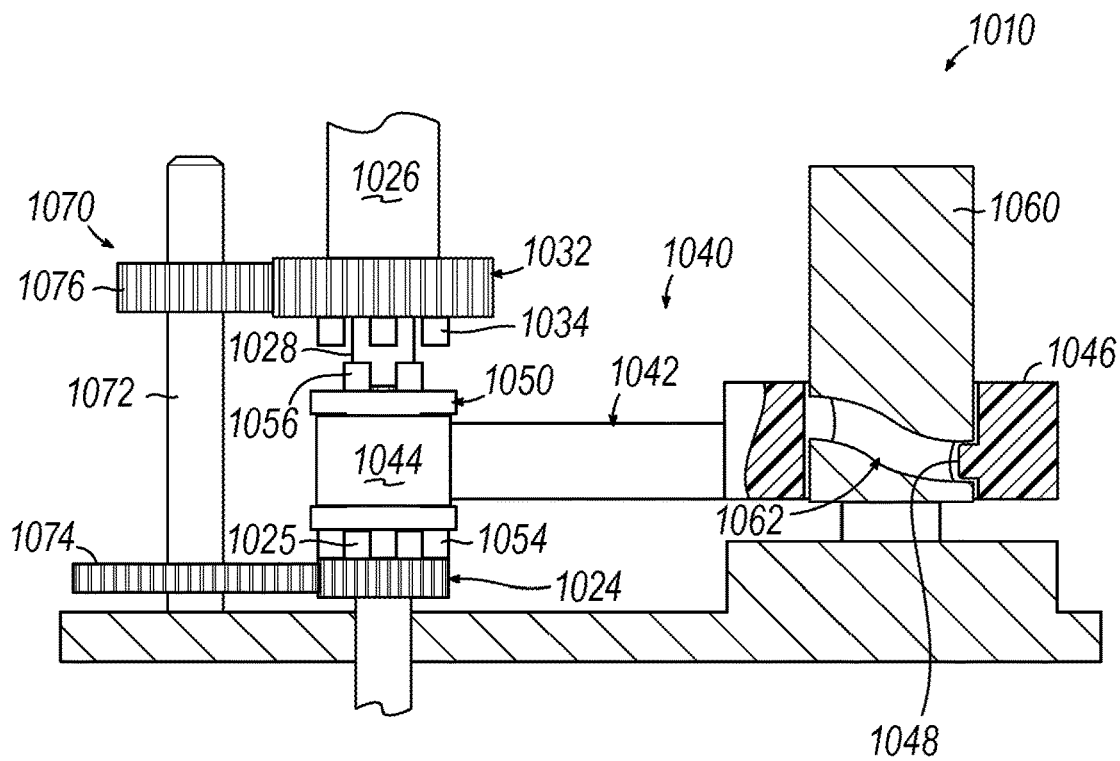
FIG. 27A depicts a side elevational view of the shifting mechanism of FIG. 24, the shifting mechanism in a direct drive configuration.
Figure 27B:
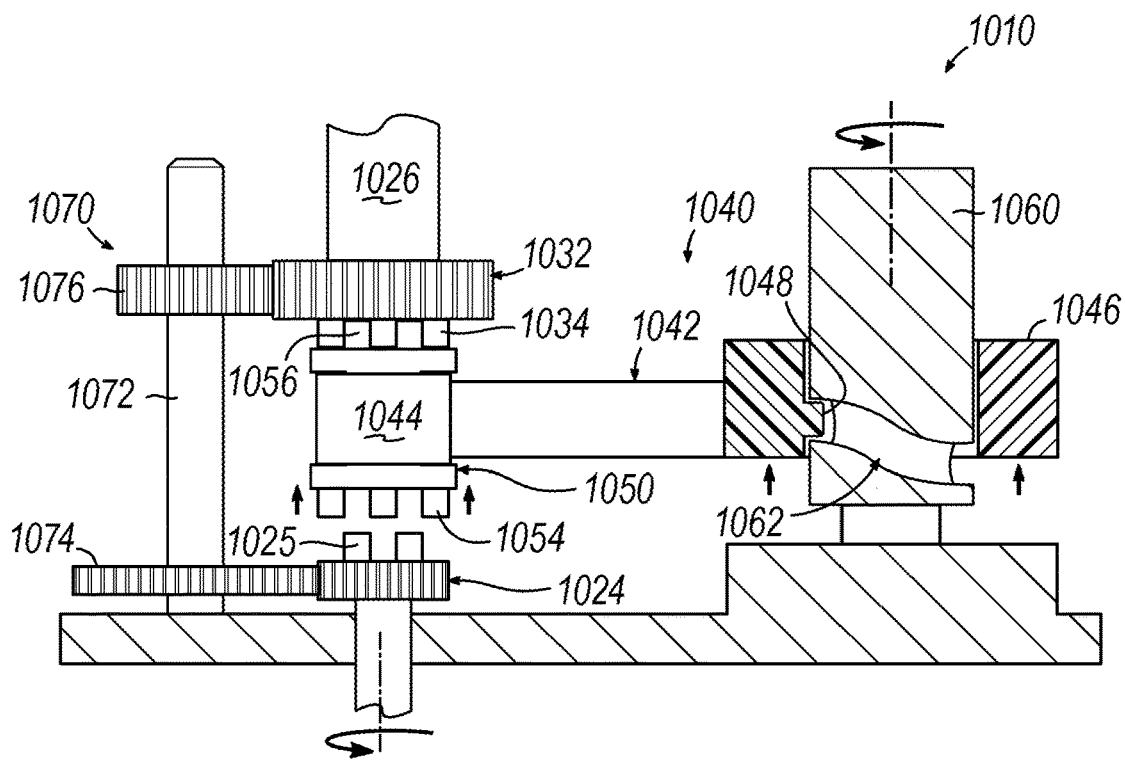
FIG. 27B depicts a side elevational view of the shifting mechanism of FIG. 24, the shifting mechanism in a reduction drive configuration.

FIGS. 27A and 27B show an exemplary use of shifting mechanism (1010). As can be seen, shifting mechanism (1010) may initially be in the direct drive configuration as shown in FIG. 27A. Shifting mechanism (1010) may then shift to the reduction drive configuration shown in FIG. 27B via rotation of shift shaft (1060).

In the direct drive configuration shown in FIG. 27A, shift shaft (1060) is rotated to drive shaft arm (1042) downwardly toward input gear (1024) via engagement between cam profile (1062) and cam protrusion (1048). With shift arm (1042) driven downwardly, lower engagement portion (1054) of clutch (1050) is driven into engagement with engagement portion (1025) of input gear (1024). As a result, input gear (1024) may drive rotation of clutch (1050). Clutch (1050) may then drive rotation of output shaft (1026). Thus, in the direct drive configuration, rotation of input shaft (1022) directly drives rotation of output shaft (1026) via clutch (1050).

In the present use, the direct drive configuration corresponds to a relatively high-speed drive with relatively low torque. In use with surgical instrument (110) this form of drive may be desirable for functions requiring low force. For instance, in use of shifting mechanism (1010) with surgical instrument (110) to drive actuation of end effector (116), it may be desirable to initially actuate end effector (116) with high speed and low torque for procedural steps where end effector (116) is prepared for use or for procedural steps where end effector (116) is being initially closed without manipulating tissue.

To shift shifting mechanism (1010) from the direct drive configuration to the reduction drive configuration, shift shaft (1060) may be rotated to drive movement of shift arm (1042) upwardly toward idler gear (1032). Specifically, engagement between cam profile (1062) and cam protrusion (1048) may convert rotation of shift shaft (1060) into axial translation of shift arm (1042). Movement of shift arm (1042) may then drive upper engagement portion (1056) of clutch (1050) into engagement with engagement portion (1034) of idler gear (1032).

Upon engagement between upper engagement portion (1056) of clutch (1050) and engagement portion (1034) of idler gear (1032), clutch (1050) and idler gear (1032) may be rotationally locked to each other such that rotation of idler gear (1032) may rotate clutch (1050). Input gear (1024) may then drive rotation of large reduction gear (1074), which may drive rotation of reduction shaft (1072) and small reduction gear (1076). Small reduction gear (1076) may then drive rotation of idler gear (1032). Idler gear (1032) may then rotate clutch (1050) due to engagement between upper engagement portion (1056) of clutch (1050) and engagement portion (1034) of idler gear (1032). Clutch (1050) may then rotate output shaft (1026) via keyed bore (1058) of clutch (1050) and keyed portion (1039) of output shaft (1026).

In the present use, the reduction drive configuration corresponds to a relatively low-speed drive with relatively high torque. In use with surgical instrument (110) this form of drive may be desirable for functions requiring high force. For instance, in use of shifting mechanism (1010) with surgical instrument (110) to drive actuation of end effector (116), it may be desirable to actuate end effector (116) with low speed and high torque for procedural steps where end effector (116) is used in connection with manipulating tissue such as clamping, cutting, and/or stapling.

D. Exemplary Alternative Shifting Mechanism with Planetary Gear

Figure 28:
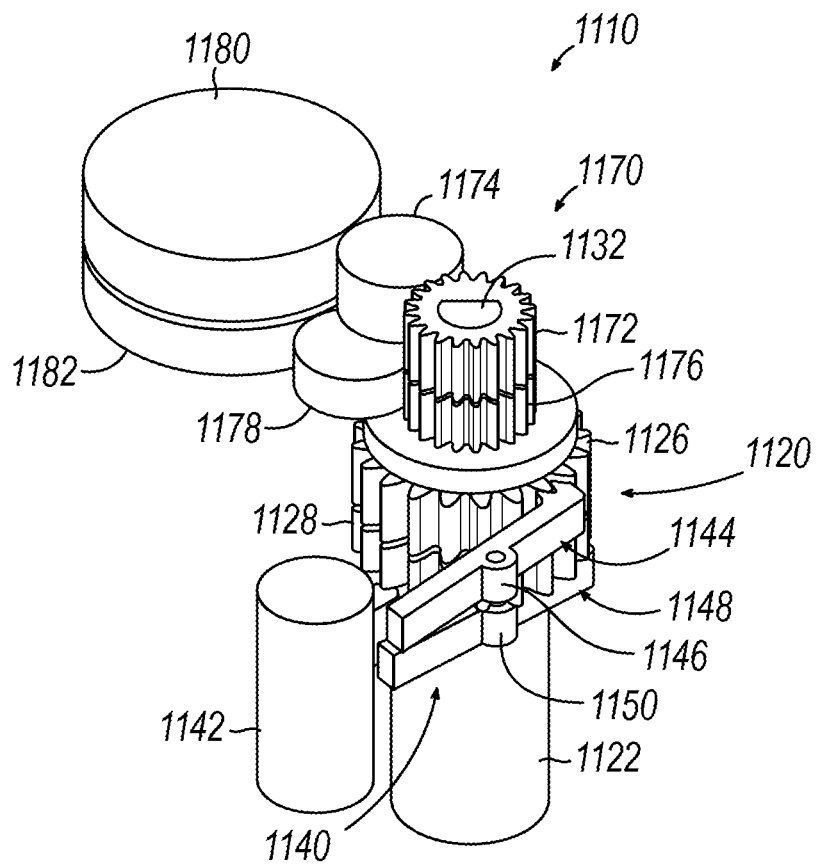
FIG. 28 depicts a perspective view of still another exemplary alternative shifting mechanism that may be used with the surgical instrument of FIG. 4.

FIG. 28 shows an exemplary alternative shifting mechanism (1110) that may be readily incorporated into any one or more of drive systems (320, 420, 520) described above in addition to, or in lieu of, shifting mechanisms (810, 910, 1010) described above. Shifting mechanism (1110) of the present example is generally configured to selectively drive two functions of surgical instrument (110) using a planetary gear driven by a single motor. For instance, in the case of incorporation with drive system (320), shifting mechanism (1110) may be associated with any one of drive inputs (332, 334, 352, 372, 374) to drive multiple functions of surgical instrument (110) with input from only one drive input (332, 334, 352, 372, 374). In one merely exemplary implementation, shifting mechanism (1110) may receive input from first articulation drive input (332), second articulation drive input (334), or primary rotation drive input (372) to selectively drive articulation of end effector (116) and rotation of shaft assembly (114) using only one of first articulation drive input (332), second articulation drive input (334), or primary rotation drive input (372). Of course, in other examples, shifting mechanism (1110) may be used in combination with other drive inputs (332, 334, 352, 372, 374) to drive other combinations of functions as will be apparent to those of ordinary skill in the art in view of the teachings herein.

Shifting mechanism (1110) includes a drive assembly (1120), a shift assembly (1140) and an output assembly (1170). As will be described in greater detail below, drive assembly (1120) is generally configured to provide rotary input to shifting mechanism (1110) that may be diverted to two or more outputs of output assembly (1170) using shift assembly (1140). Shift assembly (1140) includes a motor (1122), an upper control gear (1126), and a lower control gear (1128). Motor (1122) of the present example may correspond to a motor in robotic arm (42). In the context of implementation with drive system (320), motor (1122) may correspond to any of the motors associated with drive inputs (332, 334, 352, 372, 374).

Upper control gear (1126) and lower control gear (1128) are positioned above motor (1122). Upper control gear (1126) and lower control gear (1128) are further in communication with motor (1122) such that motor (1122) may communicate rotary motion to upper control gear (1126) or lower control gear (1128), depending on the configuration of shifting mechanism (1110). As will be described in greater detail below, upper control gear (1126) and lower control gear (1128) are generally configured to be rotationally locked and unlocked by one or more portions of shift assembly (1140) to control communication of rotary motion to output assembly (1170).

Figure 29:
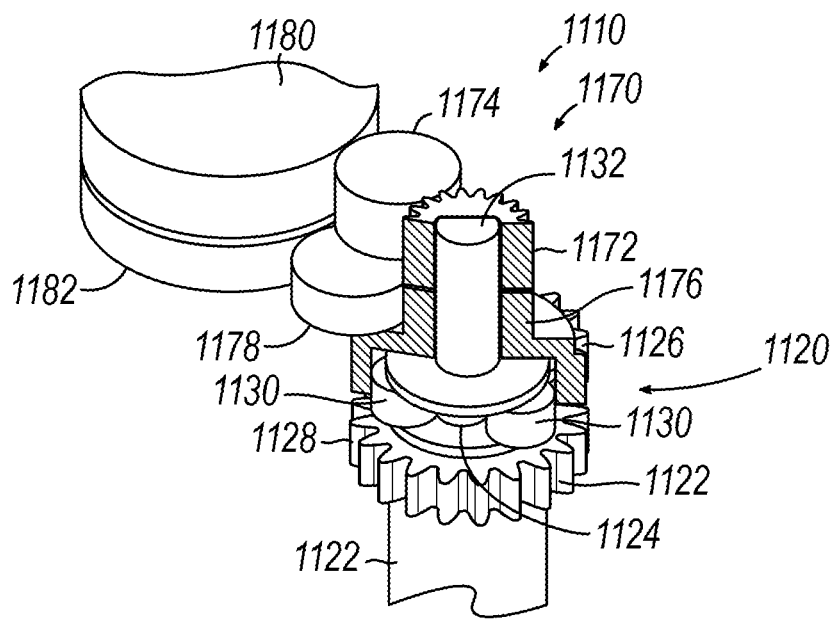
FIG. 29 depicts a perspective cutaway view of the shifting mechanism of FIG. 28.

As best seen in FIG. 29, the interior of upper control gear (1126) houses a planetary gear mechanism. Specifically, motor (1122) is in direct communication with a sun gear (1124) disposed at the central rotational axis of upper control gear (1126). Around sun gear (1124), a plurality of planet gears (1130) are arranged in a ring-shaped formation. Planet gears (1130) are rotatably fixed to lower control gear (1128). It should be understood that upper control gear (1126) and lower control gear (1128) are positioned coaxially relative to each other such that planet gears (1130) are configured to rotate about sun gear (1124) within the interior of upper control gear (1126).

A planet drive shaft (1132) is positioned above planet gears (1130). Specifically, planet gears (1130) are also rotatably fixed to planet drive shaft (1132). Thus, lower control gear (1128) and planet drive shaft (1132) are together configured to operate as a planet gear carrier, while upper control gear (1126) is configured to act as a planetary ring gear. It should be understood that reference to planet gears (1130) herein as being "rotatably fixed" refers planet gears (1130) being fixed in a given position relative to lower control gear (1128) and planet drive shaft (1132), yet also being free to rotate relative to lower control gear (1128) and planet drive shaft (1132) about a rotation axis defined by each respective planet gear (1130).

Shift assembly (1140) includes a cam shifter (1142), an upper lock arm (1144), and a lower lock arm (1148). Cam shifter (1142) is generally configured to rotate to selectively manipulate the position of lock arms (1144, 1148) relative to control gears (1126, 1128). Specifically, cam shifter (1142) includes a pair of cams (1143) extending outwardly from a cylindrical surface of cam shifter (1142). Each cam (1143) defines a protrusion that is positioned at a different position along the circumference of cam shifter (1142). Because of this different positioning of each cam (1143), cams (1143) may manipulate each lock arm (1144, 1148) at a different rotational position of cam shifter (1142).

Lock arms (1144, 1148) are generally configured to selectively lock rotation of a respective control gear (1126, 1128). Specifically, upper lock arm (1144) is associated with upper control gear (1128). Meanwhile, lower lock arm (1148) is associated with lower control gear (1128). Each lock arm (1144, 1148) includes a respective pivot (1146, 1150) such that each lock arm (1144, 1148) may be pivoted to engage one or more teeth disposed on an end of each lock arm (1144, 1148) with a respective control gear (1126, 1128).

Output assembly (1170) is disposed above drive assembly (1120) and is generally configured to receive rotary input from drive assembly (1120) and to communicate such rotary input to other portions of surgical instrument (110). Output assembly (1170) includes an upper output gear (1172), a lower output gear (1176), an upper drive gear (1180), and a lower drive gear (1182). Upper output gear (1172) is in communication with planet drive shaft (1132) such that planet drive shaft (1132) is configured to rotate upper output gear (1172). Meanwhile, lower output gear (1176) is integral, or otherwise in communication, with upper control gear (1126) such that upper control gear (1126) is configured to rotate lower output gear (1176).

Upper drive gear (1180) and lower drive gear (1182) are each configured to communicate with other portions of surgical instrument (110) to drive functions of surgical instrument (110). For instance, in some examples upper drive gear (1180) may be in communication with a function such as end effector (116) articulation, end effector (116) actuation, or shaft assembly (114) rotation. Meanwhile, lower drive gear (1182) may be in communication with another function such as shaft assembly (114) rotation, end effector (116) actuation, or end effector (116) articulation. Thus, it should be understood that upper drive gear (1180) and lower drive gear (1182) may be configured to drive different functions of surgical instrument (110) (or different aspects of a function such as pitch and yaw articulation of end effector (116)).

Upper drive gear (1180) is configured to communicate with upper output gear (1172) via an upper idler gear (1174) configured to mesh with both upper drive gear (1180) and upper output gear (1172). Similarly, lower drive gear (1182) is configured to communicate with lower output gear (1176) via a lower idler gear (1178) configured to mesh with both lower drive gear (1182) and lower output gear (1176). It should be understood that idler gears (1174, 1178) in the present example are merely optional and may be omitted in some examples. In other words, in some examples, drive gears (1180, 1182) may be configured to mesh directly with a respective output gear (1172, 1176).

In an exemplary use of shifting mechanism (1110) cam shifter (1142) may be rotated to alternate between unlocking rotation of upper control gear (1126) and lower control gear (1128). Depending on which of upper control gear (1126) and lower control gear (1128) is unlocked for rotation, either lower drive gear (1182) or upper drive gear (1180) may be driven by motor (1122).

In a first use with lower drive gear (1182) driven by motor (1122), cam shifter (1142) may be rotated to pivot lower lock arm (1148) about pivot (1150) to drive one or more teeth of lower lock arm (1148) into engagement with lower control gear (1128). In this configuration, rotation of lower control gear (1128) is locked, while rotation of upper control gear (1126) is unlocked.

With rotation of lower control gear (1128) locked, planet gears (1130) are also in a fixed position within upper control gear (1126), but still remain rotatable relative to the rotation axis of each planet gear (1130). Planet gears (1130) may then be rotated via motor (1122) by sun gear (1124). Rotation of planet gears (1130) may then rotate upper control gear (1126), which may include internal gearing to facilitate engagement between the interior of upper control gear (1126) and planet gears (1130).

Upon rotation of upper control gear (1126) output assembly (1170) may be driven using rotation of upper control gear (1126), which may rotate lower output gear (1176). Lower output gear (1176) may then rotate lower idler gear (1178), which may ultimately rotate lower drive gear (1182). As noted above, lower drive gear (1182) may then be used to drive various functions of surgical instrument such as rotation of shaft assembly (114), actuation of end effector (116), or articulation of end effector (116).

In a second use with upper drive gear (1180) driven by motor (1122), cam shifter (1142) may be rotated to pivot upper lock arm (1144) about pivot (1146) to drive one or more teeth of upper lock arm (1144) into engagement with upper control gear (1126). Cam shifter (1142) may also be rotated to pivot lower lock arm (1148) about pivot (1150) to drive one or more teeth of lower lock arm (1148) out of engagement with lower control gear (1128). In this configuration, rotation of upper control gear (1126) is locked, while rotation of lower control gear (1128) is unlocked.

With rotation of upper control gear (1126) locked, planet gears (1130) may be used to drive rotation of lower control gear (1128). Specifically, lower control gear (1128) is freely rotatable, so planet gears (1130) may rotate lower control gear (1128). Meanwhile, with upper control gear (1126), rotation of planet gears (1130) via sun gear (1124) drives planet gears (1130) around the interior of upper control gear (1126) with gearing of upper control gear (1126) acting similarly to a track or cylindrical rack for planet gears (1130) to travel along. Thus, motor (1122) may drive rotation of lower control gear (1128) via sun gear (1124) and planet gears (1130).

As noted above, planet drive shaft (1132) is also coupled to planet gears (1130). As such, planet gears (1130) may likewise drive rotation of planet drive shaft (1132). Upon rotation of planet drive shaft (1132), output assembly (1170) may be driven using rotation of planet drive shaft (1132). Specifically, planet drive shaft (1132) is coupled to upper output gear (1172) such that planet drive shaft (1132) may rotate upper output gear (1172). Upper output gear (1172) may then rotate upper idler gear (1174), which may ultimately rotate upper drive gear (1180). As noted above, upper drive gear (1180) may then be used to drive various functions of surgical instrument (110) such as articulation of end effector (116), actuation of end effector (116), or rotation of shaft assembly (114).

IV. Exemplary Surgical Instrument with Positive Jaw Opening Mechanism

In some examples, structures similar to end effector (116) described above may counter compressive forces or stick loads during procedures. Such forces result in challenges associated with opening structures similar to end effector (116) under some circumstances. Such challenges may be more apparent in end effectors including a spring or other resilient feature for opening. Thus, it may be desirable to incorporate various features into surgical instruments similar to surgical instrument (110) described above suitable for opening an end effector using a manually applied positive force rather than relying on a passive spring force. Although certain specific features are described below, it should be understood that such features may be combined in other examples. Additionally, certain features described below may be readily combined with other features described herein as will be apparent to those of ordinary skill in the art in view of the teachings herein.

Figure 30:
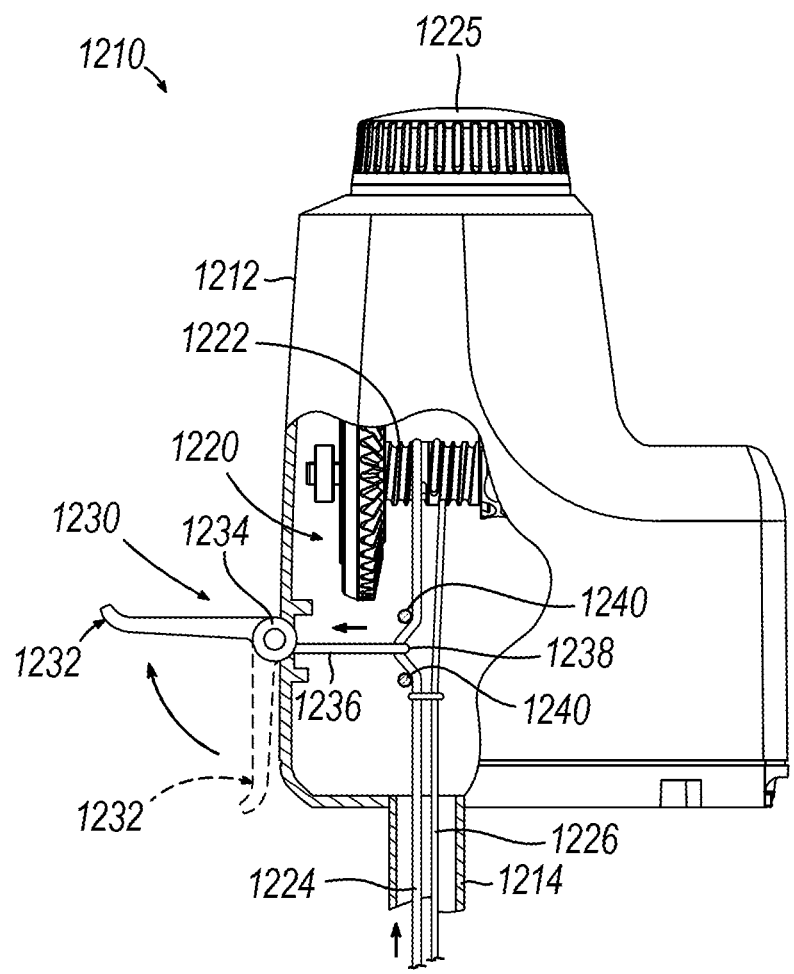
FIG. 30 depicts a cutaway side elevational view of a proximal base portion of an exemplary alternative surgical instrument that may be used with the robotic surgical system of FIG. 1.
Figure 31A:
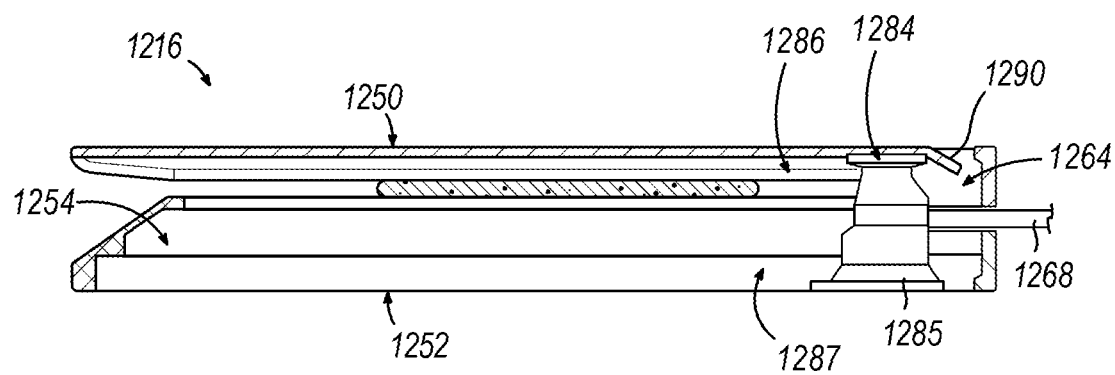
FIG. 31A depicts a side elevational view of an end effector of the surgical instrument of FIG. 30, the end effector in a closed configuration.

FIGS. 30 and 31A show an exemplary alternative surgical instrument (1210) that may be readily used in connection with robotic surgical system (10) described above in lieu of surgical instrument (110). Surgical instrument (1210) of the present example is substantially similar to surgical instrument (110) described above. For instance, as with surgical instrument (110) described above, surgical instrument (1210) of the present example includes an instrument base (1212), a shaft assembly (1214) extending distally from instrument base (1212), and an end effector (1216) at a distal end of shaft assembly (1214). Instrument base (1212) of the present example is similar to instrument base (112) described above in that instrument base (1212) may include an attachment interface (not shown) configured to interface with and be driven by corresponding output couplers (not shown) of robotic arm (42). Instrument base (1212) also includes a drive system (1220) similar to drive system (120) described above.

Drive system (1220) may include a manual actuator (1225), which is shown in the form of a knob configured to be manually rotated. Manual actuator (1225) may engage other components of surgical instrument (1210) to serve as a "bailout" mechanism to obtain a desired movement in end effector (1216) without powered actuation of drive system (1220).

End effector (1216) of the present example is also similar to end effector (116) described above. For instance, like with end effector (116) described above, end effector (1216) of the present example is configured as a surgical stapler, which may also be referred to herein as an "endocutter," configured to clamp, cut, and staple tissue. As best seen in FIG. 31A, end effector (1216) includes opposing upper and lower jaws (1250, 1252) configured to move relative to one another between open and closed positions for clamping and releasing tissue.

One or both of upper and lower jaws (1250, 1522) may be configured to pivot and thereby actuate end effector (1216) between open and closed positions. Lower jaw (1252) includes a removable staple cartridge (1254), which may be substantially similar to staple cartridge (154) described above. In the illustrated example, lower jaw (1252) is pivotable relative to upper jaw (1250) to move between an open, unclamped position and a closed, clamped position.

End effector (1216) similarly includes a driving assembly (1264) that includes a pusher member (1266) that is operatively coupled with an actuation mechanism via a push rod (1268). Firing assembly (1258) may also include a wedge sled (not shown), and a knife member (not shown) to facilitate cutting and/or stapling of tissue.

Pusher member (1266) as including first and second flanges (1284, 1285). First flange (1284) is configured to be received in a longitudinal slot (1286) of upper jaw (1250) and second flange (1285) is configured to be received in a longitudinal slot (1287) of staple cartridge (1254) of lower jaw (1252). Similar to first and second flanges (184, 185) described above, first and second flanges (1284, 1285) are configured to move along longitudinal slots (1286, 1287) during actuation of pusher member (1266).

Drive system (1220) of the present example further includes an actuation capstan (1222) with a pair of actuation drive cables (1224, 1226) extending distally from actuation capstan (1222). Actuation capstan (1222) is generally configured for rotation by other components of drive system (1220). During rotation, actuation capstan (1222) is generally configured to lengthen or release one actuation drive cable (1224, 1226), while tensioning or pulling another actuation drive cable (1224, 1226), depending on the direction of rotation of actuation capstan (1222).

Actuation drive cables (1224, 1226) are generally configured to manipulate pusher member (1266) of end effector (1216) to actuate end effector (1216). Specifically, actuation drive cables (1224, 1226) include a retraction actuation drive cable (1224) and an advancement actuation drive cable (1226). Retraction actuation drive cable (1224) is configured to manipulate pusher member (1266) proximally, while advancement actuation drive cable (1226) is configured to manipulate pusher member (1266) distally. In some examples, retraction actuation drive cable (1224) may have a greater thickness or diameter relative to advancement actuation drive cable (1226) to promote proximal movement of pusher member (1266) during a bailout condition.

Although not shown, it should be understood that in some examples actuation drive cables (1224, 1226) may be in communication with other components such as pulleys, blocks, tackles, frames, shuttles and/or etc. disposed within shaft assembly (1214) to facilitate manipulation of pusher member (1266) via actuation drive cables (1224, 1226). Such other components may be in communication with push rod (1268) to transmit motion of actuation drive cables (1224, 1226) to pusher member (1266). In some examples, such other components associated with actuation drive cables (1224, 1226) may be configured in accordance with at least some of the teachings of U.S. patent application Ser. No. 17/402,749, entitled "Firing Bailout System for Powered Surgical Stapler," filed on Aug. 16, 2021, published as U.S. Pub. No. 2023/0045998 on Feb. 16, 2023, the disclosure of which is incorporated by reference herein in its entirety.

Unlike surgical instrument (110) described above, surgical instrument (1210) of the present example includes a manual jaw release mechanism (1230) associated with drive system (1220). Manual jaw release mechanism (1230) is generally configured to directly manipulate one or more of actuation drive cables (1224, 1226) to manipulate actuation of end effector (1216) without reliance on other components of drive system (1220).

Manual Jaw Release Mechanism (1230) includes an actuator (1232), an actuation rod (1236), and tension posts (1240). Actuator (1232) is disposed on the exterior of instrument base (1212) such that actuator (1232) is accessible to an operator for manual actuation. Actuator (1232) of the present example is configured as a pivot arm to be manually pivoted, pulled, or rotated by an operator. As such, actuator (1232) includes a pivot (1234) defining an axis about which actuator (1232) may pivot.

Actuation rod (1236) extends laterally from actuator (1232) toward retraction actuation drive cable (1224). Actuation rod (1236) includes a cable manipulator (1238) configured to engage retraction actuation drive cable (1224). Cable manipulator (1238) in the present example is in the form of a hook configured to bend around a portion of retraction actuation drive cable (1224). Although cable manipulator (1238) uses a hook form in the present example, it should be understood that in other examples, cable manipulator (1238) may take on a variety of forms such as a loop, a movable cam feature, a plate and rod configuration, and/or etc.

Actuator (1232) is coupled to actuation rod (1236) and is configured to drive lateral movement of actuation rod (1236) upon movement of actuator (1232). Specifically, tension posts (1240) are positioned proximate retraction actuation drive cable (1224). In this configuration, movement of actuation rod (1236) may be relative to tension posts (1240) to pull retraction actuation drive cable (1224) between tension posts (1240), thereby adding tension to retraction actuation drive cable (1224). As will be described in greater detail below, actuator (1232), actuation rod (1236), and tension posts (1240) may operate together to manipulate one or more of actuation drive cables (1224, 1226) independently of drive system (1220).

Unlike end effector (116) described above, end effector (1216) of the present example includes a positive jaw opening feature (1290) configured to receive input from pusher member (1266) to drive movement of upper jaw (1250) relative to lower jaw (1252). As best seen in FIG. 31A, positive jaw opening feature (1290) is formed by a proximal portion of upper jaw (1250) extending at an angle downwardly from an upper portion of upper jaw (1250) and into longitudinal slot (1286). Although positive jaw opening feature (1290) of the present example is shown as having a specific configuration, it should be understood that in other examples the configuration of positive jaw opening feature (1290) may vary. For instance, in some examples, the angle of extension of positive jaw opening feature (1290) may be smaller or lager. In other examples, positive jaw opening feature (1290) may have a convex or concave curved configuration. In still other examples, positive jaw opening feature (1290) may be in the form of a detent mechanism.

Regardless of the particular configuration of positive jaw opening feature (1290), positive jaw opening feature (1290) is generally configured to engage a portion of pusher member (1266) such as first flange (1284) during proximal translation of pusher member (1266). The position of positive jaw opening feature (1290) is proximate the proximal end of upper jaw (1250), which may also correspond to a hinge or pivot used for movement of upper jaw (1250) relative to low jaw (1252). Thus, engagement between positive jaw opening feature (1290) and pusher member (1266) may exert a force on upper jaw (1250), which may pivot upper jaw (1250) open relative to lower jaw (1252).

Figure 31B:
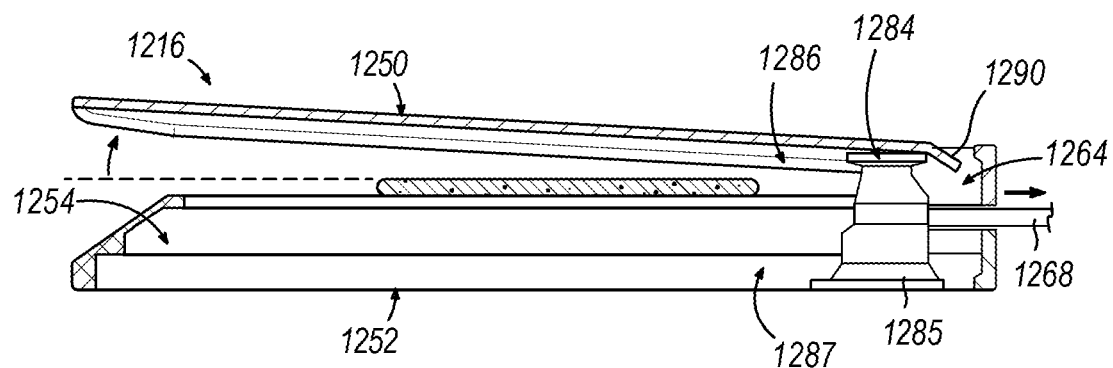
FIG. 31B depicts another side elevational view of the end effector of FIG. 31A, the end effector in a partially open configuration.

FIGS. 30, 31A and 31B show an exemplary use of manual jaw release mechanism (1230) and positive jaw opening feature (1290) to move upper jaw (1250) relative to lower jaw (1252). As can be seen, in FIG. 30, manual jaw release mechanism (1230) may be actuated by moving actuator (1232) from an initial disengaged position (phantom) to an engaged position (solid lines). This may include pivoting of actuator (1232), which may pull actuation rod (1236) laterally. Lateral movement of actuation rod (1236) may then pull retraction actuation drive cable (1224) laterally between tension posts (1240). This lateral pulling of retraction actuation drive cable (1224) may increase the tension on retraction actuation drive cable (1224). As will be described in greater detail below, this tension may be communicated through shaft assembly (1214) to pusher member (1266) of end effector (1216).

FIG. 31A shows the position of pusher member (1266) with actuator (1232) in the initial disengaged position. In this position, pusher member (1266) may be retracted within longitudinal slots (1286, 1287) and be proximate positive jaw opening feature (1290).

Upon movement of actuator (1232) to the engaged position, tension applied to retraction actuation drive cable (1224) may pull pusher member (1266) proximally as shown in FIG. 31B. Proximal movement of pusher member (1266) may then engage positive jaw opening feature (1290). As pusher member (1266) continues moving proximally, additional force may be exerted on positive jaw opening feature (1290), which may force upper jaw (1250) into the position shown in FIG. 31B.

Figure 32A:
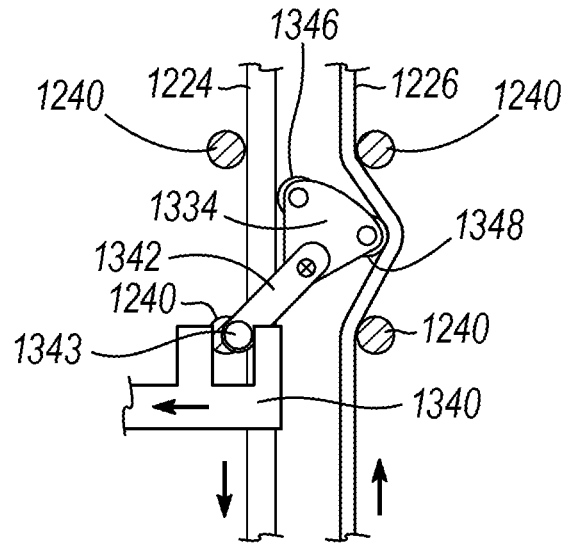
FIG. 32A depicts a side elevational view of an exemplary alterative cable manipulator for use with the surgical instrument of FIG. 30, the cable manipulator in a first configuration.
Figure 32B:
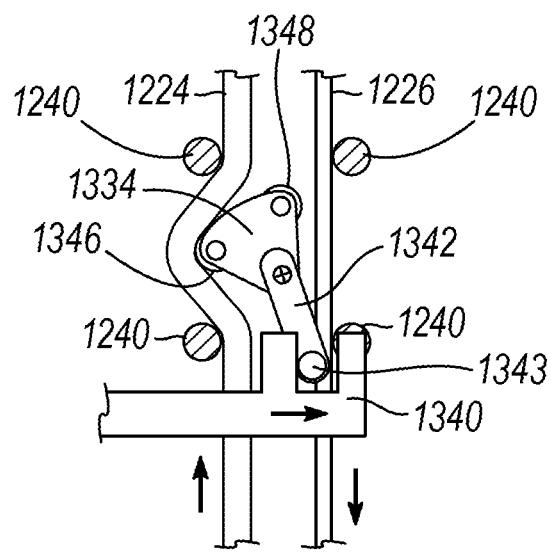
FIG. 32B depicts another side elevational view of the cable manipulator of FIG. 32A, the cable manipulator in a second configuration.

FIGS. 32A and 32B show an exemplary alternative cable manipulator (1338) that may be used with manual jaw release mechanism (1230) described above in lieu of cable manipulator (1238). Cable manipulator (1338) is similar to cable manipulator (1238) described above in that cable manipulator (1338) is configured to manipulate one or more of actuation drive cables (1224, 1226) to increase tension in one or more of actuation drive cables (1224, 1226) by moving one or more of actuation drive cables (1224, 1226) out of plane.

Unlike cable manipulator (1238) described above, cable manipulator (1338) of the present example is generally configured as a cam mechanism rather than a hook. Moreover, cable manipulator (1338) of the present example is generally configured to manipulate both of retraction actuation drive cable (1224) and advancement actuation drive cable (1226) rather than only retraction actuation drive cable (1224).

Cable manipulator (1238) includes a drive member (1340), a drive arm (1342), and a cam block (1344). Drive member (1340) is configured to couple to actuation rod (1236) such that drive member (1340) is configured to be driven relative to actuation drive cables (1224, 1226). Drive member (1340) of the present example is in the form of a double L-pattern or a patter having block and cutout. Alternatively, drive member (1340) may be formed of a loop, cylinder, or other similar feature.

Drive arm (1342) extends from drive member (1340) to cam block (1344). Drive member (1340) includes a drive post (1343) configured to engage drive member (1340). Specifically, drive post (1343) is configured for receipt within a portion of drive member (1340) such that drive post (1343) may be moved laterally in both directions by drive member (1340), but still pivot or rotate within drive member (1340). Opposite drive post (1343), drive arm (1342) is rotatably coupled to cam block (1344).

Cam block (1344) defines a generally triangular body with drive arm (1342) coupled at one vertex, a first cam (1346) coupled at another vertex and a second cam (1348) coupled at another vertex. Cam block (1344) is generally configured to rotate between actuation drive cables (1224, 1226) to selectively engage first cam (1346) or second cam (1348) with a given actuation drive cable (1224, 1226). Specifically, first cam (1346) is configured to engage retraction actuation drive cable (1224), while second cam (1348) is configured to engage advancement actuation drive cable (1226). Although not shown, it should be understood that cam block (1344) may be rotatably secured to a grounding structure such as a post or rod configured to maintain the position of cam block (1344) within surgical instrument (1210), while permitting rotation of cam block (1344) relative to actuation drive cables (1224, 1226).

FIGS. 32A and 32B show an exemplary use of cable manipulator (1338). As best seen in FIG. 32A, drive member (1340) may initially be pulled laterally toward retraction actuation drive cable (1224). In use with manual jaw release mechanism (1230), this may correspond to actuator (1232) being moved to the engaged position. Alternatively, in some uses with manual jaw release mechanism (1230), actuator (1232) this may correspond to actuator (1232) being moved to the disengaged position.

As drive member (1340) moves, drive member (1340) may pull drive post (1343) of drive arm (1342) laterally in the same direction. This pulling motion of drive arm (1342) may pull one side of cam block (1344), thereby rotating cam block (1344) in the direction of drive arm (1342). Upon rotation of cam block (1344), second cam (1348) may be driven into contact with advancement actuation drive cable (1226) as first cam (1346) may be driven away from retraction actuation drive cable (1224). Thus, actuation drive cable (1226) may be driven out of plane, thereby increasing the tension applied to actuation drive cable (1226).

Next, drive member (1340) may be driven laterally in the opposite direction as shown in FIG. 32B. As drive member (1340) moves, drive member (1340) may push drive post (1342) of drive arm (1342) laterally towards actuation drive cable (1226). This pushing motion of drive arm (1342) may pull one side of cam block (1344), thereby rotating cam block (1344) in the direction of drive arm (1342). Upon rotation of cam block (1344), second cam (1348) may be driven way from advancement action drive cable (1226) as first cam (1346) may be driven into contact with retraction actuation cable (1224). Thus, retraction drive cable (1224) may be driven out of plane, thereby increasing the tension applied to retraction drive cable (1224).

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: a body; a shaft assembly extending distally from the body; an end effector disposed on a distal end of the shaft assembly, wherein the end effector includes a first jaw and a second jaw; a stapling assembly supported by one of the first jaw or the second jaw of the end effector; and a drive system including a shifting mechanism configured to selectively modify a mechanical advantage of a drive input driven by a motor and used to power one or more functions associated with operation of the end effector.

Example 2

The surgical instrument of Example 1, wherein the drive system is configured to rotate the shaft assembly relative to the body, articulate the end effector relative to a longitudinal axis of the shaft assembly, and actuate a pusher member of the end effector relative to the first jaw and the second jaw, wherein the shifting mechanism is configured to selectively modify the mechanical advantage for rotation of the shaft assembly, articulation of the end effector, or actuation of the pusher member.

Example 3

The surgical instrument of Example 2, wherein the drive system includes a first drive input configured to drive rotation of the shaft assembly, a second drive input configured to drive articulation of the end effector, and a third drive input configured to drive actuation of the pusher member, wherein the shifting mechanism is in communication with one or more of the first drive input, the second drive input, or the third drive input.

Example 4

The surgical instrument of Example 2, wherein the drive system includes a first drive input configured to drive rotation of the shaft assembly, a second drive input configured to drive articulation of the end effector, and a third drive input configured to drive actuation of the pusher member, wherein the shifting mechanism is in communication with only one of the first drive input, the second drive input, or the third drive input.

Example 5

The surgical instrument of Example 3, wherein the drive system includes a first drive input configured to drive rotation of the shaft assembly, a second drive input configured to drive articulation of the end effector, and a third drive input configured to drive actuation of the pusher member, wherein the shifting mechanism is configured to selectively control communication of power from the first drive input to the second drive input, or the third drive input.

Example 6

The surgical instrument of Example 2, wherein the drive system includes a first drive input configured to drive rotation of the shaft assembly, a second drive input configured to drive articulation of the end effector about a yaw axis, a third drive input configured to drive articulation of the end effector about a pitch axis, and a fourth drive input configured to drive actuation of the pusher member, wherein the shifting mechanism is configured to selectively control communication of power from the first drive input to the second drive input, the third drive input, or the fourth drive input.

Example 7

The surgical instrument of any one or more of Examples 1 through 6, wherein the drive system further includes a function lock, wherein the shifting mechanism is configured to communicate with the function lock to lockout one or more functions associated with operation of the end effector.

Example 8

The surgical instrument of any one or more Examples 1 through 7, wherein the drive system further includes a transfer gear, wherein the shifting mechanism is configured to move the transfer gear to transfer power from the drive input from one function associated with operation of the end effector to another function associated with operation of the end effector.

Example 9

The surgical instrument of any one or more of Examples 1 through 8, wherein the shifting mechanism includes an input shaft, an output shaft and a reduction assembly, wherein a portion of the shifting mechanism is configured to selectively drive the output shaft via the reduction assembly.

Example 10

The surgical instrument of Example 9, wherein the shifting mechanism further includes a clutch, wherein the clutch is keyed to the output shaft, wherein the shifting mechanism is configured to move the clutch into communication with the input shaft or a portion of the reduction assembly.

Example 11

The surgical instrument of Example 10, wherein the shifting mechanism further includes a shift arm configured to move the clutch.

Example 12

The surgical instrument of Example 10, wherein the shifting mechanism further includes a shift arm and a shift shaft, wherein rotation of the shift shaft is configured to move the shift arm to thereby move the clutch.

Example 13

The surgical instrument of Example 10, wherein the shifting mechanism further includes a shift arm and a shift shaft, wherein the shift shaft includes a cam profile, wherein the cam profile is configured to drive movement the shift arm to thereby move the clutch.

Example 14

The surgical instrument of any one or more of Examples 1 through 13, wherein the shifting mechanism includes one or more planetary gear mechanisms.

Example 15

The surgical instrument of any one or more of Examples 1 through 14, wherein the shifting mechanism includes one or more sheaves.

Example 16

The surgical instrument of any one or more of Examples 1 through 15, wherein the body includes a coupler configured to communicate with a robotic arm.

Example 17

A surgical instrument, comprising: a body including a coupler configured to communicate with a robotic arm; a shaft assembly extending distally from the body; an end effector disposed on a distal end of the shaft assembly, wherein the end effector includes a first jaw and a second jaw; a staple cartridge configured to be received within the first jaw or the second jaw of the end effector; and a drive system configured to interface with the robotic arm, wherein the drive system includes a shifting mechanism and a plurality of drive inputs, wherein the shifting mechanism is configured to couple at least two of the drive inputs together to power one more functions associated with operation of the end effector.

Example 18

The surgical instrument of Example 17, wherein the drive system includes a first drive input configured to actuate the end effector, and a second drive input configured to articulate the end effector relative to the shaft assembly, wherein the shifting mechanism is configured to couple the first drive input to the second drive input.

Example 19

The surgical instrument of Example 17, wherein the drive system includes a first drive input configured to actuate the end effector, and a second drive input configured to articulate the end effector relative to the shaft assembly, wherein the first drive input and the second drive input are configured to operate independently of each other.

Example 20

The surgical instrument of any one or more Examples 17 through 19, wherein the drive system includes one or more bands extending between at least two drive inputs, wherein at least a portion of the shifting mechanism is configured to control a tension applied to each band of the one or more bands.

Example 21

A method for use of a surgical instrument, the method comprising: driving a first function of the surgical instrument using a first rotary drive from a first drive input; shifting a shifting mechanism of the surgical instrument to communicate the first rotary drive of the first drive input to a second drive input, thereby generating a second rotary drive powered by both the first drive input and the second drive input; and driving a second function of the surgical instrument using the second rotary drive.

Example 22

The method of Example 21, further comprising shifting the shifting mechanism of the surgical instrument to communicate the first rotary drive of the first drive input to a third drive input, thereby generating a second rotary drive; and driving a third function of the surgical instrument using the third rotary drive.

Example 23

The method of Examples 21 or 22, wherein the act of shifting the shifting mechanism includes tensioning one or more bands associated with the first drive input.

Example 24

The method of any one or more of Examples 21 through 23, wherein the act of shifting the shifting mechanism includes moving a gear from one drive input to another drive input.

Example 25

The method of any one or more of Examples 21 through 24, further comprising shifting the shifting mechanism of the surgical instrument to lock the first function of the surgical instrument.

Example 26

The method of any one or more of Examples 21 through 25, wherein the first function of the surgical instrument corresponds to rotation of a shaft assembly extending from a body of the surgical instrument to an end effector of the surgical instrument.

Example 27

The method of Example 26, wherein the second function of the surgical instrument corresponds to actuation of the end effector of the surgical instrument.

IV. Miscellaneous

Any one or more of the teachings, expressions, embodiments, examples, etc. described herein may be combined with any one or more of the teachings, expressions, embodiments, examples, etc. described in U.S. patent application Ser. No. 17/402,674, entitled "Methods of Operating a Robotic Surgical Stapler," filed on Aug. 16, 2021, published as U.S. Pub. No. 2023/0051361 on Feb. 16, 2023; U.S. patent application Ser. No. 17/402,675, entitled "Multi-Threshold Motor Control Algorithm for Powered Surgical Stapler," filed on Aug. 16, 2021, published as U.S. Pub. No. 2023/0051271 on Feb. 16, 2023; U.S. patent application Ser. No. 17/402,677, entitled "Variable Response Motor Control Algorithm for Powered Surgical Stapler," filed on Aug. 16, 2021, issued as U.S. Pat. No. 11,944,297 on Apr. 2, 2024; U.S. patent application Ser. No. 17/402,679, entitled "Powered Surgical Stapler Having Independently Operable Closure and Firing Systems," filed on Aug. 16, 2021, issued as U.S. Pat. No. 11,779,332 on Oct. 10, 2023; U.S. patent application Ser. No. 17/402,695, entitled "Firing System Features for Surgical Stapler," filed on Aug. 16, 2021, published as U.S. Pub. No. 2023/0050707 on Feb. 16, 2023; U.S. patent application Ser. No. 17/402,701, entitled "Multiple-Sensor Firing Lockout Mechanism for Powered Surgical Stapler," filed on Aug. 16, 2021, published as U.S. Pub. No. 2023/0050358 on Feb. 16, 2023; U.S. patent application Ser. No. 17/402,703, entitled "Proximally Located Firing Lockout Mechanism for Surgical Stapler," filed on Aug. 16, 2021, issued as U.S. Pat. No. 11,957,336 on Apr. 16, 2024; U.S. patent application Ser. No. 17/402,720, entitled "Cartridge-Based Firing Lockout Mechanism for Surgical Stapler," filed on Aug. 16, 2021, published as U.S. Pub. No. 2023/0051222 on Feb. 16, 2023; U.S. patent application Ser. No. 17/402,732, entitled "Sled Restraining Member for Surgical Stapler," filed on Aug. 16, 2021, published as U.S. Pub. No. 2023/0045893 on Feb. 16, 2023; U.S. patent application Ser. No. 17/402,738, entitled "Firing Member Tracking Feature for Surgical Stapler," filed on Aug. 16, 2021 published as U.S. Pub. No. 2023/0049736 on Feb. 16, 2023; U.S. patent application Ser. No. 17/402,749, entitled "Firing Bailout System for Powered Surgical Stapler," filed on Aug. 16, 2021, published as U.S. Pub. No. 2023/0045998 on Feb. 16, 2023; and/or U.S. patent application Ser. No. 17/402,759, entitled "Deflectable Firing Member for Surgical Stapler," filed on Aug. 16, 2021, published as U.S. Pub. No. 2023/0052307 on Feb. 16, 2023. The disclosure of each of these applications is incorporated by reference herein in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the systems, instruments, and/or portions thereof, followed by cleaning or replacement of particular pieces, and subsequent reassembly. In particular, some versions of the systems, instruments, and/or portions thereof may be disassembled, and any number of the particular pieces or parts of the systems, instruments, and/or portions thereof may be selectively replaced or removed in any combination. Upon cleaning and/or replacement of particular parts, some versions of the systems, instruments, and/or portions thereof may be reassembled for subsequent use either at a reconditioning facility, or by an operator immediately prior to a procedure. Those skilled in the art will appreciate that reconditioning of systems, instruments, and/or portions thereof may utilize a variety of techniques for disassembly, cleaning/replacement, and reassembly. Use of such techniques, and the resulting reconditioned systems, instruments, and/or portions thereof, are all within the scope of the present application.

By way of example only, versions described herein may be sterilized before and/or after a procedure. In one sterilization technique, the systems, instruments, and/or portions thereof is placed in a closed and sealed container, such as a plastic or TYVEK bag. The container and system, instrument, and/or portion thereof may then be placed in a field of radiation that can penetrate the container, such as gamma radiation, x-rays, or high-energy electrons. The radiation may kill bacteria on the system, instrument, and/or portion thereof and in the container. The sterilized systems, instruments, and/or portions thereof may then be stored in the sterile container for later use. Systems, instruments, and/or portions thereof may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   (a) a body;
   (b) a shaft assembly extending distally from the body;
   (c) an end effector disposed on a distal end of the shaft assembly, wherein the end effector includes a first jaw and a second jaw;
   (d) a stapling assembly supported by one of the first jaw or the second jaw of the end effector; and
   (e) a drive system including a shifting mechanism, an articulation drive module, an actuation drive module, and a rotation drive module, the shifting mechanism being configured to selectively modify a mechanical advantage of a drive input driven by a motor and used to power one or more functions associated with operation of the end effector, the shifting mechanism being further configured to selectively place the articulation drive module into mechanical communication with the actuation drive module, the rotation drive module, or both.

2. The surgical instrument of claim 1, wherein the drive system is configured to rotate the shaft assembly relative to the body via the rotation drive module, articulate the end effector relative to a longitudinal axis of the shaft assembly via the articulation drive module, and actuate a pusher member of the end effector relative to the first jaw and the second jaw via the actuation drive module, wherein the shifting mechanism is configured to selectively modify the mechanical advantage for rotation of the shaft assembly, articulation of the end effector, or actuation of the pusher member.

3. The surgical instrument of claim 2, wherein the drive system includes a first drive input configured to drive rotation of the shaft assembly, a second drive input configured to drive articulation of the end effector, and a third drive input configured to drive actuation of the pusher member, wherein the shifting mechanism is in communication with one or more of the first drive input, the second drive input, or the third drive input.

4. The surgical instrument of claim 3, wherein the drive system includes a first drive input configured to drive rotation of the shaft assembly, a second drive input configured to drive articulation of the end effector, and a third drive input configured to drive actuation of the pusher member, wherein the shifting mechanism is configured to selectively control communication of power from the first drive input to the second drive input, or the third drive input.

5. The surgical instrument of claim 2, wherein the drive system includes a first drive input configured to drive rotation of the shaft assembly, a second drive input configured to drive articulation of the end effector about a yaw axis, a third drive input configured to drive articulation of the end effector about a pitch axis, and a fourth drive input configured to drive actuation of the pusher member, wherein the shifting mechanism is configured to selectively control communication of power from the first drive input to the second drive input, the third drive input, or the fourth drive input.

6. The surgical instrument of claim 1, wherein the drive system further includes a function lock, wherein the shifting mechanism is configured to communicate with the function lock to lockout one or more functions associated with operation of the end effector.

7. The surgical instrument of claim 1, wherein the drive system further includes a transfer gear, wherein the shifting mechanism is configured to move the transfer gear to transfer power from the drive input from one function associated with operation of the end effector to another function associated with operation of the end effector.

8. The surgical instrument of claim 1, wherein the shifting mechanism includes an input shaft, an output shaft and a reduction assembly, wherein a portion of the shifting mechanism is configured to selectively drive the output shaft via the reduction assembly.

9. The surgical instrument of claim 8, wherein the shifting mechanism further includes a clutch, wherein the clutch is keyed to the output shaft, wherein the shifting mechanism is configured to move the clutch into communication with the input shaft or a portion of the reduction assembly.

10. The surgical instrument of claim 9, wherein the shifting mechanism further includes a shift arm configured to move the clutch.

11. The surgical instrument of claim 9, wherein the shifting mechanism further includes a shift arm and a shift shaft, wherein rotation of the shift shaft is configured to move the shift arm to thereby move the clutch.

12. The surgical instrument of claim 9, wherein the shifting mechanism further includes a shift arm and a shift shaft, wherein the shift shaft includes a cam profile, wherein the cam profile is configured to drive movement the shift arm to thereby move the clutch.

13. The surgical instrument of claim 1, wherein the shifting mechanism includes one or more planetary gear mechanisms.

14. The surgical instrument of claim 1, wherein the body includes a coupler configured to communicate with a robotic arm, wherein the shifting mechanism includes one or more sheaves.

15. A surgical instrument, comprising:
(a) a body including a coupler configured to communicate with a robotic arm;
(b) a shaft assembly extending distally from the body;
(c) an end effector disposed on a distal end of the shaft assembly, wherein the end effector includes a first jaw and a second jaw;
(d) a stapling assembly supported by one of the first jaw or the second jaw of the end effector; and
(e) a drive system configured to interface with the robotic arm, wherein the drive system includes a shifting mechanism and a plurality of drive inputs, wherein the shifting mechanism is configured to couple at least two of the drive inputs together to power one or more functions associated with operation of the end effector, wherein the drive system includes a first drive input configured to actuate the end effector between an open and closed position, and a second drive input configured to articulate the end effector relative to the shaft assembly, wherein the shifting mechanism is configured to couple the first drive input to the second drive input.

16. The surgical instrument of claim 15, wherein the first drive input and the second drive input are configured to operate independently of each other.

17. The surgical instrument of claim 15, wherein the drive system includes one or more bands extending between at least two drive inputs, wherein at least a portion of the shifting mechanism is configured to control a tension applied to each band of the one or more bands.

18. A surgical instrument, comprising:
(a) a body including a coupler configured to communicate with a robotic arm;
(b) a shaft extending distally from the body;
(c) an end effector disposed on a distal end of the shaft, wherein the end effector includes a first jaw and a second jaw;
(d) a stapling assembly supported by one of the first jaw or the second jaw of the end effector; and
(e) a drive system configured to interface with the robotic arm, wherein the drive system includes a shifter, an articulation driver, an actuation driver, and a rotation driver, wherein the articulation driver is configured to drive articulation of the end effector relative to the shaft, wherein the actuation driver is configured to drive closure of the end effector, wherein the rotation driver is configured to drive rotation of the end effector relative to the shaft, wherein the shifter is configured to selectively mechanically couple the articulation driver to the actuation driver or the rotation driver.

19. The surgical instrument of claim 18, wherein the articulation driver includes a pitch drive input and a yaw drive input, wherein the actuation driver includes a actuation drive input, wherein the rotation driver includes a rotation drive input, wherein the shifter is configured to selectively place the pitch drive input or the yaw drive input into mechanical communication with the actuation drive input or the rotation drive input.

20. The surgical instrument of claim 19, wherein the shifter is configured to selectively place the pitch drive input or the yaw drive input into mechanical communication with the actuation drive input or the rotation drive input to communicate power from the actuation drive input or the rotation drive input to the pitch drive input or the yaw drive input.

* * * * *